(12) United States Patent
Reiffenrath et al.

(10) Patent No.: US 6,203,724 B1
(45) Date of Patent: Mar. 20, 2001

(54) CROSSLINKED CYCLOHEXANE DERIVATIVES, AND LIQUID-CRYSTALLINE MEDIUM

(75) Inventors: Volker Reiffenrath, Rossdorf; Michael Heckmeier, Bensheim; Matthias Bremer, Darmstadt, all of (DE)

(73) Assignee: Merck Patent Gesellschaft mit beschrankter Haftung (DE)

( * ) Notice: Subject to any disclaimer, the term of this patent is extended or adjusted under 35 U.S.C. 154(b) by 0 days.

(21) Appl. No.: 09/453,538

(22) Filed: Dec. 3, 1999

(30) Foreign Application Priority Data

Dec. 3, 1998 (DE) ................................. 198 55 757

(51) Int. Cl.[7] ........................ C09K 19/34; C09K 19/02; C07F 15/00; C07C 2/00
(52) U.S. Cl. ................. 252/299.61; 252/299.63; 349/182; 349/193; 556/9; 585/534
(58) Field of Search ................ 585/534; 556/9; 252/299.61, 299.63; 349/182, 193

(56) References Cited

U.S. PATENT DOCUMENTS 5,344,587 * 9/1994 Coates et al. .................. 252/299.66
5,665,271 * 9/1997 Ogihara et al. ................. 252/299.61

OTHER PUBLICATIONS

Wei et al, CA 129:97536.*
Tomi et al, CA 128:251017.*
Gillies et al, CA 118:106039.*
Kanehara et al, CA 113:234442.*
Maillard et al, CA 107:175419.*
Kakabehov et al, CA 77:61277.*

* cited by examiner

Primary Examiner—Deborah C. Lambkin
(74) Attorney, Agent, or Firm—Millen, White, Zelano & Branigan, P.C.

(57) ABSTRACT

The invention relates to cyclohexane derivatives of the formula I

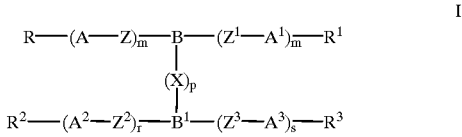

in which R, $R^1$, $R^2$, $R^3$, A, $A^1$, $A^2$, $A^3$, Z, $Z^1$, $Z^2$, $Z^3$, B, $B^1$, X, p, m, n, r and s are as defined above.

16 Claims, No Drawings

CROSSLINKED CYCLOHEXANE DERIVATIVES, AND LIQUID-CRYSTALLINE MEDIUM

SUMMARY OF THE INVENTION

The invention relates to novel cyclohexane derivatives of the formula I

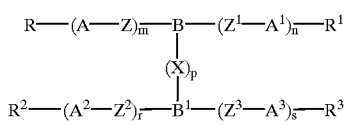

in which

B and B$^1$, independently of one another, are

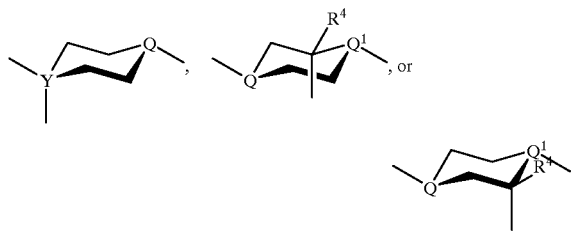

where the rings B and B$^1$ are each bonded to the group $(X)_p$ via the axial bond, and, in addition, one or two non-adjacent CH$_2$ groups in these rings may be replaced by O, Y, independently of one another if it occurs more than once, is C or Si, Q and Q$^1$, independently of one another, are CH or SiH, X, independently of one another if it occurs more than once, is —C≡C—, —CH=CH—, —CF=CF—, —CF=CH—, —CH$_2$—, —COO— or 1,4-phenylene, in which, in addition, one or more CH groups may, independently of one another, be replaced by N or CF, p is 1, 2, 3 or 4, R, R$^1$, R$^2$, R$^3$ and R$^4$, independently of one another, are H, an alkyl radical having 1–12 carbon atoms which is unsubstituted or at least monosubstituted by halogen and in which, in addition, one or more CH$_2$ groups may each, independently of one another, be replaced by —O—, —S—, —CO—,

—CO—O—, —O—CO—, —O—CO—O— or —CH=CH— in such a way that heteroatoms are not connected directly, or are —CN, —F, —CF$_3$, —OCHF$_2$, —OCF$_3$, —OCHFCF$_3$, —OCH$_2$CF$_3$, —OCF$_2$—CF$_3$ or —CH=CF$_2$, A, A$^1$, A$^2$ and A$^3$, independently of one another, are

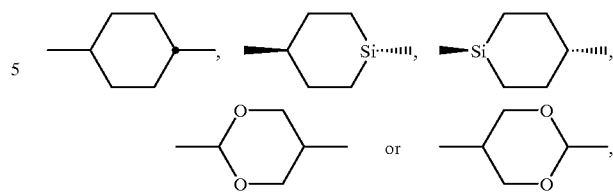

or 1,4-phenylene in which one or more CH groups are replaced by N, where the rings A, A$^1$, A$^2$ and A$^3$, independently of one another, may be substituted by one or more F atoms or —NCS, —CN, —CF$_3$ or —OCF$_3$, Z, Z$^1$, Z$^2$, and Z$^3$ are each, independently of one another, —CO—O—, —O—CO—, —CH$_2$O—, —CH=CH—, —O—, —O—CH$_2$—, —CH$_2$CH$_2$—, —(CH$_2$)$_3$—, —(CH$_2$)$_4$—, —CF$_2$—CF$_2$—, —OCF$_2$— or a single bond, and n, m, r and s, independently of one another, are 0, 1 or 2.

The invention also relates to the use of the compounds of the formula I as components of liquid-crystalline media, and to liquid-crystal and electro-optical display elements which contain the liquid-crystalline media according to the invention.

The compounds of the formula I frequently have a small positive or negative value of the dielectric anisotropy and can be used as components of liquid-crystalline media, in particular for displays based on the principle of the twisted cell, the guest-host effect, the effect of deformation of aligned phases (DAP) or electrically controlled birefringence (ECB) or the effect of dynamic scattering.

The substances employed hitherto for this purpose all have certain disadvantages, for example inadequate stability to the action of heat, light or electric fields, or unfavorable elastic and/or dielectric properties.

The invention this provides novel, stable, liquid-crystalline or mesogenic compounds of particularly low optical anisotropy Δn and negative or positive dielectric anisotropy which are suitable as components of liquid-crystalline media, in particular for TFT and STN displays.

It has now been found that the compounds of the formula I are eminently suitable as components of liquid-crystalline media. They can be used to obtain stable liquid-crystalline media, in particular suitable for TFT or STN displays. The novel compounds are distinguished, in particular, by high thermal stability, which is advantageous for a high "holding ratio", and exhibit favorable clearing point values. The compounds of the formula I preferably have an optical anisotropy value Δn of <0.05, particularly preferably <0.03, which is attributable to a particularly high value of n$_{195}$, at a reduced temperature of 0.9 and a wavelength of 589 nm. The reduced temperature here is defined as follows:

$$\frac{\text{measurement temperature in K}}{\text{clearing point temperature in K}} = \text{reduced temperature}$$

Small values of Δn are achieved in accordance with the invention by the group $(X)_p$ being perpendicular to the longitudinal axis of the molecule through its axial position. The resultant increased polarizability transverse to this axis results in an increased n$_\perp$. With Δn=n$_\|$−n$_\perp$ (for example L. Pohl, U. Finkenzeller, in Liquid Crystals, Vol. 1, 152, Ed. B. Bahadur, World Scientific, 1990), small values of the optical anisotropy thus arise.

Liquid-crystalline media having very small optical anisotropy values are of particular importance for reflective and transflective applications, i.e. applications in which the particular LCD experiences no or only supportive background illumination.

The provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

Addition of compounds of the formula I to liquid-crystalline dielectrics allows the Δn values of such media to be considerably reduced.

The meaning of the formula I covers all isotopes of the chemical elements bound in the compounds of the formula I.

In enantiomerically pure or enriched form, the compounds of the formula I are also suitable as chiral dopants and in general for producing chiral mesophases.

In the pure state, the compounds of the formula I are colorless and form liquid-crystalline mesophases in a temperature range which is favorably located for electro-optical use. They are stable chemically, thermally and to light.

At a decreasing wavelength of light, the values of $n_\parallel$ of conventional calamitic liquid crystals increase more strongly than the values of $n_\perp$ and, since $\Delta n = n_\parallel - n_\perp$, an increase of Δn results.

In contrast to these conventional lc-materials, the $n_\parallel$ and $n_\perp$ values of compounds of the present invention exhibit an unusual frequency dependence:

At decreasing wavelength, the values of $n_\perp$ of the compounds of formula I increase more strongly than the values of $n_\parallel$. Thus, a decrease of Δn results.

Preferred compounds of the formula I display very low values of Δn measured under usual conditions (20° C., 598 nm). At certain wavelengths $n_\parallel$ and $n_\perp$ of these compounds adopt the same value (Δn=0, see example 266). At even shorter wavelengths $n_\perp$ is larger than $n_\parallel$ and Δn is negative. Thus, dependent on the wavelength of the light used, the inventive compounds exhibit an inversion of Δn.

The inventive compounds are therefore preferably suitable for the compensation of the frequency dependence of Δn in conventional liquid crystalline mixtures.

Furthermore, these compounds can be used for the production of optical switches or filters, which remove only certain wavelengths of light reaching them.

The compounds of the formula I can be converted into liquid-crystalline polymers through elevated temperature or use of UV light.

The invention thus relates to the compounds of the formula I and to the use of these compounds as components of liquid-crystalline media. The invention furthermore relates to liquid-crystalline media comprising at least one compound of the formula I, and to liquid-crystal display elements, optical switches or filters, in particular electro-optical display elements, which contain media of this type.

Above and below, B, $B^1$, R, $R^1$, $R^2$, $R^3$, $R^4$, A, $A^1$, $A^2$, $A^3$, X, p, Z, $Z^1$, $Z^2$, $Z^3$, Q, $Q^1$, Y, n, m, r and s are as defined above, unless expressly stated otherwise. If the radical X occurs more than once, it can have the same or different meanings. The same applies to all other groups which occur more than once.

For reasons of simplicity, Cyc below denotes a cyclohexane-1,4-diyl radical or a 1- or 4-silacyclohexane-1,4-diyl radical, and Dio denotes a 1,3-dioxane-2,5-diyl radical, where Cyc may be unsubstituted or mono- or polysubstituted by F or CN.

In the formula I, the groups R—(A—Z)$_m$—B—($Z^1$—$A^1$)$_n$—$R^1$ and $R^2$—($A^2$—$Z^2$)$_r$—$B^1$—($Z^3$—$A^3$)$_s$—$R^3$ preferably have one of the meanings of the sub-formulae Ia1 to Ia12, which, besides the group W, which is as defined for B or $B^1$, contain a six-membered ring:

| | |
|---|---|
| $R^5$—W—Cyc—$R^6$ | Ia1 |
| $R^5$—W—CH$_2$CH$_2$—Cyc—$R^6$ | Ia2 |
| $R^5$—W—COO—Cyc—$R^6$ | Ia3 |
| $R^5$—W—Dio—$R^6$ | Ia4 |
| $R^5$—W—CH$_2$CH$_2$—Dio—$R^6$ | Ia5 |
| $R^5$—W—COO—Dio—$R^6$ | Ia6 |
| $R^5$—Cyc—W—$R^6$ | Ia7 |
| $R^5$—Dio—W—$R^6$ | Ia8 |
| $R^5$—Cyc—CH$_2$CH$_2$—W—$R^6$ | Ia9 |
| $R^5$—Dio—CH$_2$CH$_2$—W—$R^6$ | Ia10 |
| $R^5$—Cyc—COO—W—$R^6$ | Ia11 |
| $R^5$—Dio—COO—W—$R^6$ | Ia12 | furthermore the likewise preferred compounds of the sub-formulae Ib1 to Ib72, which, in addition to the group W, contain two six-membered rings:

| | |
|---|---|
| $R^5$—Cyc—Cyc—W—$R^6$ | Ib1 |
| $R^5$—Dio—Cyc—W—$R^6$ | Ib2 |
| $R^5$—Cyc—CH=CH—Cyc—W—$R^6$ | Ib3 |
| $R^5$—Dio—CH$_2$CH$_2$—Cyc—W—$R^6$ | Ib4 |
| $R^5$—Cyc—COO—Cyc—W—$R^6$ | Ib5 |
| $R^5$—Dio—COO—Cyc—W—$R^6$ | Ib6 |
| $R^5$—Cyc—Dio—W—$R^6$ | Ib7 |
| $R^5$—Dio—Dio—W—$R^6$ | Ib8 |
| $R^5$—Cyc—CH$_2$CH$_2$—Dio—W—$R^6$ | Ib9 |
| $R^5$—Dio—CH$_2$CH$_2$—Dio—W—$R^6$ | Ib10 |
| $R^5$—Cyc—COO—Dio—W—$R^6$ | Ib11 |
| $R^5$—Dio—COO—Dio—W—$R^6$ | Ib12 |
| $R^5$—Cyc—Cyc—CH$_2$CH$_2$—W—$R^6$ | Ib13 |
| $R^5$—Dio—Cyc—CH$_2$CH$_2$—W—$R^6$ | Ib14 |
| $R^5$—Cyc—Dio—CH$_2$CH$_2$—W—$R^6$ | Ib15 |
| $R^5$—Dio—Dio—CH$_2$CH$_2$—W—$R^6$ | Ib16 |
| $R^5$—Cyc—Cyc—COO—W—$R^6$ | Ib17 |
| $R^5$—Dio—Cyc—COO—W—$R^6$ | Ib18 |
| $R^5$—Cyc—Dio—COO—W—$R^6$ | Ib19 |
| $R^5$—Dio—Dio—COO—W—$R^6$ | Ib20 |
| $R^5$—Cyc—W—Cyc—$R^6$ | Ib21 |
| $R^5$—Dio—W—Cyc—$R^6$ | Ib22 |
| $R^5$—Cyc—CH$_2$CH$_2$—W—Cyc—$R^6$ | Ib23 |
| $R^5$—Dio—CH$_2$CH$_2$—W—Cyc—$R^6$ | Ib24 |
| $R^5$—Cyc—CH=CH—W—Cyc—$R^6$ | Ib25 |
| $R^5$—Dio—COO—W—Cyc—$R^6$ | Ib26 |
| $R^5$—Cyc—W—CH$_2$CH$_2$—Cyc—$R^6$ | Ib27 |
| $R^5$—Dio—W—CH$_2$CH$_2$—Cyc—$R^6$ | Ib28 |
| $R^5$—Cyc—W—COO—Cyc—$R^6$ | Ib29 |
| $R^5$—Dio—W—COO—Cyc—$R^6$ | Ib30 |
| $R^5$—Cyc—W—Dio—$R^6$ | Ib31 |
| $R^5$—Dio—W—Dio—$R^6$ | Ib32 |
| $R^5$—Cyc—CH$_2$CH$_2$—W—Dio—$R^6$ | Ib33 |
| $R^5$—Dio—CH$_2$CH$_2$—W—Dio—$R^6$ | Ib34 |
| $R^5$—Cyc—COO—W—Dio—$R^6$ | Ib35 |
| $R^5$—Dio—COO—W—Dio—$R^6$ | Ib36 |
| $R^5$—Cyc—W—CH$_2$CH$_2$—Dio—$R^6$ | Ib37 |
| $R^5$—Dio—W—CH$_2$CH$_2$—Dio—$R^6$ | Ib38 |
| $R^5$—Cyc—W—COO—Dio—$R^6$ | Ib39 |
| $R^5$—DiO—W—COO—Dio—$R^6$ | Ib40 |

-continued

| | |
|---|---|
| R⁵—W—Cyc—Cyc—R⁶ | Ib41 |
| R⁵—W—CH₂CH₂—Cyc—Cyc—R⁶ | Ib42 |
| R⁵—W—COO—Cyc—Cyc—R⁶ | Ib43 |
| R⁵—W—Dio—Cyc—R⁶ | Ib44 |
| R⁵—W—CH₂CH₂—Dio—Cyc—R⁶ | Ib45 |
| R⁵—W—COO—Dio—Cyc—R⁶ | Ib46 |
| R⁵—W—Cyc—CH₂CH₂—Cyc—R⁶ | Ib47 |
| R⁵—W—Dio—CH₂CH₂—Cyc—R⁶ | Ib48 |
| R⁵—W—Cyc—COO—Cyc—R⁶ | Ib49 |
| R⁵—W—Dio—COO—Cyc—R⁶ | Ib50 |
| R⁵—W—Cyc—Dio—R⁶ | Ib51 |
| R⁵—W—CH₂CH2—Cyc—Dio—R⁶ | Ib52 |
| R⁵—W—COO—Cyc—Dio—R⁶ | Ib53 |
| R⁵—W—Dio—Dio—R⁶ | Ib54 |
| R⁵—W—CH₂CH₂—Dio—Dio—R⁶ | Ib55 |
| R⁵—W—CH₂CH₂—Dio—Dio—R⁶ | Ib56 |
| R⁵—W—Cyc—CH₂CH₂—Dio—R⁶ | Ib57 |
| R⁵—W—Dio—CH₂CH₂—Dio—R⁶ | Ib58 |
| R⁵—W—Cyc—COO—Dio—R⁶ | Ib59 |
| R⁵—W—Dio—COO—Dio—R⁶ | Ib60 |
| R⁵—Cyc—CH₂CH₂—W—CH₂CH₂—Cyc—R⁶ | Ib61 |
| R⁵—Dio—CH₂CH₂—W—CH₂CH₂—Cyc—R⁶ | Ib62 |
| R⁵—Cyc—CH₂CH₂—W—CH₂CH₂—Dio—R⁶ | Ib63 |
| R⁵—Dio—CH₂CH₂—W—CH₂CH₂—Dio—R⁶ | Ib64 |
| R⁵—Cyc—CH₂CH₂—Cyc—CH₂CH₂—W—R⁶ | Ib65 |
| R⁵—Dio—CH₂CH₂—Cyc—CH₂CH₂—W—R⁶ | Ib66 |
| R⁵—Cyc—CH₂CH₂—Dio—CH₂CH₂—W—R⁶ | Ib67 |
| R⁵—Dio—CH₂CH₂—Dio—CH₂CH₂—W—R⁶ | Ib68 |
| R⁵—W—CH₂CH₂—Cyc—CH₂CH₂—Cyc—R⁶ | Ib69 |
| R⁵—W—CH₂CH₂—Dio—CH₂CH₂—Cyc—R⁶ | Ib70 |
| R⁵—W—CH₂CH₂—Cyc—CH₂CH₂—Dio—R⁶ | Ib71 |
| R⁵—W—CH₂CH₂—Dio—CH₂CH₂—Dio—R⁶ | Ib72 | and the preferred compounds of the sub-formulae Ic1 to Ic55, which, in addition to the group W, contain three six-membered rings:

| | |
|---|---|
| R⁵—W—Cyc—Cyc—Cyc—R⁶ | Ic1 |
| R⁵—W—CH₂CH₂—Cyc—Cyc—Cyc—R⁶ | Ic2 |
| R⁵—W—Dio—Cyc—Cyc—R⁶ | Ic3 |
| R⁵—W—CH₂CH₂—Dio—Cyc—Cyc—R⁶ | Ic4 |
| R⁵—W—Cyc—CH₂CH₂—Cyc—Cyc—R⁶ | Ic5 |
| R⁵—W—Dio—CH₂CH₂—Cyc—Cyc—R⁶ | Ic6 |
| R⁵—W—Cyc—Cyc—CH₂CH₂—Cyc—R⁶ | Ic7 |
| R⁵—W—Dio—Cyc—CH₂CH₂—Cyc—R⁶ | Ic8 |
| R⁵—W—Cyc—Dio—Cyc—R⁶ | Ic9 |
| R⁵—W—CH₂CH₂—Cyc—Dio—Cyc—R⁶ | Ic10 |
| R⁵—W—Dio—Dio—Cyc—R⁶ | Ic11 |
| R⁵—W—CH₂CH₂—Dio—Dio—Cyc—R⁶ | Ic12 |
| R⁵—W—Cyc—CH₂CH₂—Dio—Cyc—R⁶ | Ic13 |
| R⁵—W—Dio—CH₂CH₂—Dio—Cyc—R⁶ | Ic14 |
| R⁵—W—Cyc—Dio—CH₂CH₂—Cyc—R⁶ | Ic15 |
| R⁵—Cyc—Dio—CH₂CH₂—Cyc—W—R⁶ | Ic16 |
| R⁵—Dio—Dio—CH₂CH₂—Cyc—W—R⁶ | Ic17 |
| R⁵—Cyc—Cyc—Cyc—CH₂CH₂—W—R⁶ | Ic18 |
| R⁵—Dio—Cyc—Cyc—CH₂CH₂—W—R⁶ | Ic19 |
| R⁵—Cyc—Dio—Cyc—CH₂CH₂—W—R⁶ | Ic20 |
| R⁵—Dio—Dio—Cyc—CH₂CH₂—W—R⁶ | Ic21 |
| R⁵—Cyc—Cyc—Dio—W—R⁶ | Ic22 |
| R⁵—Dio—Cyc—Dio—W—R⁶ | Ic23 |
| R⁵—Cyc—CH₂CH₂—Cyc—Dio—W—R⁶ | Ic24 |
| R⁵—Dio—CH₂CH₂—Cyc—Dio—W—R⁶ | Ic25 |
| R⁵—Cyc—Dio—Dio—W—R⁶ | Ic26 |
| R⁵—Dio—Dio—Dio—W—R⁶ | Ic27 |
| R⁵—Cyc—CH₂CH₂—Dio—Dio—W—R⁶ | Ic28 |
| R⁵—Dio—CH₂CH₂—Dio—Dio—W—R⁶ | Ic29 |
| R⁵—Cyc—Cyc—CH₂CH₂—Dio—W—R⁶ | Ic30 |
| R⁵—Dio—Cyc—CH₂CH₂—Dio—W—R⁶ | Ic31 |
| R⁵—Cyc—CH₂CH₂—Dio—W—Dio—R⁶ | Ic32 |
| R⁵—Dio—CH₂CH₂—Dio—W—Dio—R⁶ | Ic33 |
| R⁵—Cyc—CH₂CH₂—CH₂CH₂—W—Dio—R⁶ | Ic34 |
| R⁵—Dio—Cyc—CH₂CH₂—W—Dio—R⁶ | Ic35 |
| R⁵—Cyc—Dio—CH₂CH₂—W—Dio—R⁶ | Ic36 |
| R⁵—Dio—Dio—CH₂CH₂—W—Dio—R⁶ | Ic37 |
| R⁵—Cyc—Cyc—W—CH₂CH₂—Dio—R⁶ | Ic38 |
| R⁵—Dio—Cyc—W—CH₂CH₂—Dio—R⁶ | Ic39 |
| R⁵—Cyc—Dio—W—CH₂CH₂—Dio—R⁶ | Ic40 |
| R⁵—Dio—Dio—W—CH═CH—Dio—R⁶ | Ic41 |
| R⁵—Cyc—W—Dio—CH₂CH₂—Cyc—R⁶ | Ic42 |
| R⁵—Dio—W—Dio—CH₂CH₂—Cyc—R⁶ | Ic43 |
| R⁵—Cyc—W—Cyc—Dio—R⁶ | Ic44 |
| R⁵—Dio—W—Cyc—Dio—R⁶ | Ic45 |
| R⁵—Cyc—CH₂CH₂—W—Cyc—Dio—R⁶ | Ic46 |
| R⁵—Dio—CH₂CH₂—W—Cyc—Dio—R⁶ | Ic47 |
| R⁵—Cyc—W—CH₂CH₂—Cyc—Dio—R⁶ | Ic48 |
| R⁵—Dio—W—CH₂CH₂—Cyc—Dio—R⁶ | Ic49 |
| R⁵—Cyc—W—Cyc—CH₂CH₂—Dio—R⁶ | Ic50 |
| R⁵—Dio—W—Cyc—CH₂CH₂—Dio—R⁶ | Ic51 |
| R⁵—Cyc—W—Dio—Dio—R⁶ | Ic52 |
| R⁵—Dio—W—Dio—Dio—R⁶ | Ic53 |
| R⁵—Cyc—CH₂CH₂—W—Dio—Dio—R⁶ | Ic54 |
| R⁵—Dio—CH₂CH₂—W—Dio—Dio—R⁶ | Ic55 | in which Cyc and Dio are as defined above, R⁵ and R⁶, independently of one another, are as defined for R, R¹, R² and R³, and W is B or B¹.

B and B¹, independently of one another, are preferably

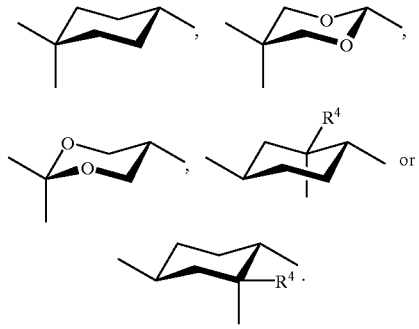

Y is preferably C.

Q and Q¹ are preferably CH.

$(X)_p$ preferably has one of the following meanings:

—C≡C—, —C≡C—C≡C—, —C≡C—C≡C—C≡C—, —C≡C—C≡C—C≡C—C≡C—, —CH═CH—, —CH═CH—CH═CH—, —C≡C—CH═CH—, —C≡C—CH═CH—C≡C—, —CH═CH—C≡C—CH═CH—, —C≡C—COO—, —CH═CH—COO—, —CH₂—CH₂—C≡C—, —CH₂—CH₂—C≡C—C≡C—, —CH₂—CH₂—C≡C—CH═CH—,

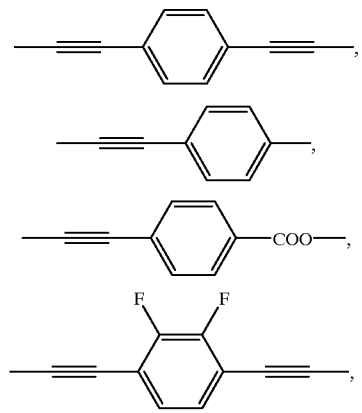

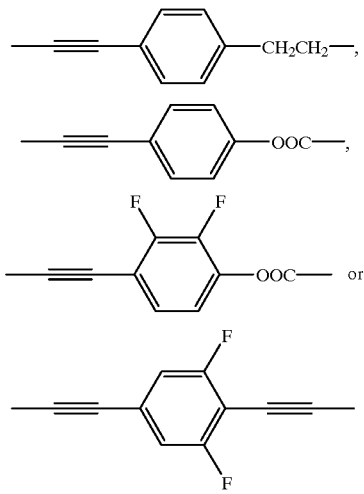

The group $(X)_p$ particularly preferably has one of the following meanings:

—C≡C—C≡C—,   —C≡C—C≡C—C≡C—,
—C≡C—C≡C—C≡C—C≡C—,   —C≡C—CH=CH—,   —CH=CH—C≡C—CH=CH—,
—C≡C—COO—,   —CH₂—CH₂—C≡C—C≡C—,
—C≡C—CH=CH—C≡C—,

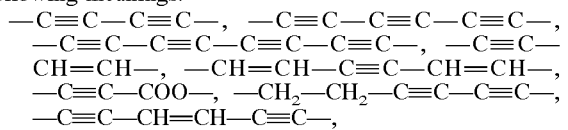

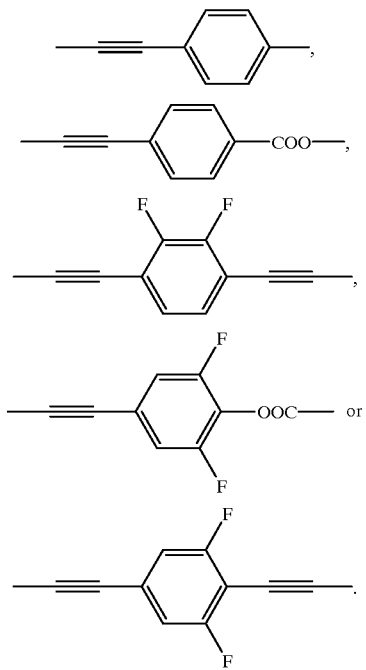

R, R¹, R², R³ and R⁴ are preferably CN, F, OCF₃, CF₃, OCF₂CF₃, CH=CF₂, alkyl or alkoxy having 1 to 10 carbon atoms, or alkenyl or alkenyloxy having 2 to 10 carbon atoms, in particular F, CF₃, OCF₃, CH=CF₂, or alkyl or alkoxy having 1 to 7 carbon atoms.

Preference is given to compounds of the formula I and of all sub-formulae in which A, A¹, A² and/or A³ are cyclohexane-1,4-diyl which is monosubstituted or disubstituted by F or CN.

R⁴ is preferably H, CH₃, F or CF₃, in particular H.

A, A¹, A² and/or A³, independently of one another, are particularly preferably

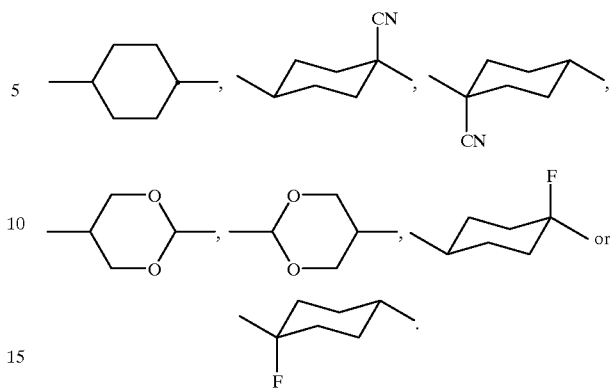

Z, Z¹, Z² and Z³, independently of one another, are preferably —CH₂CH₂—, —COO—, —OOC— or a single bond, particularly preferably a single bond or —CH₂—CH₂—.

Preference is given to compounds of the formula I in which R, R¹, R² and R³ are simultaneously alkyl or alkoxy having 1 to 10 carbon atoms.

Compounds of the formula I which contain not more than one dioxane ring likewise represent a preferred embodiment of the invention.

m, n, r and s, independently of one another, are preferably 0 or 1.

The compounds of the formula I include the preferred compounds of the sub-formulae I1 to I22:

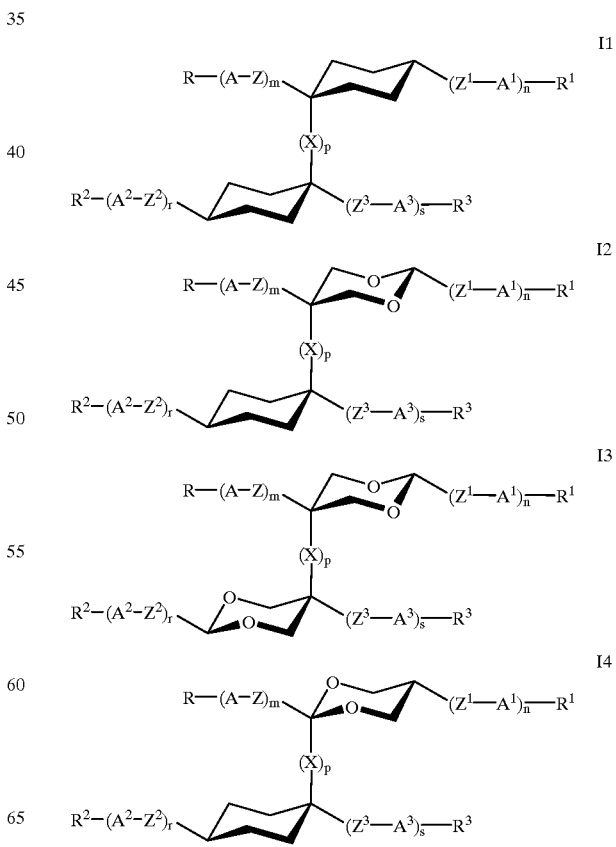

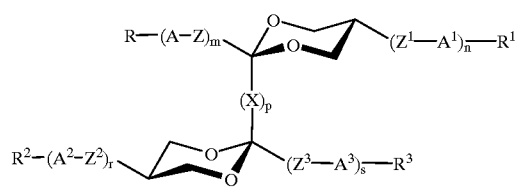
I5
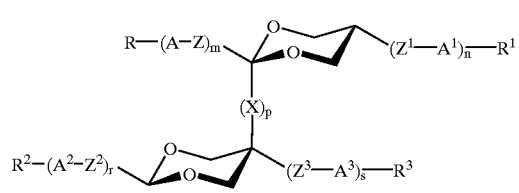
I6
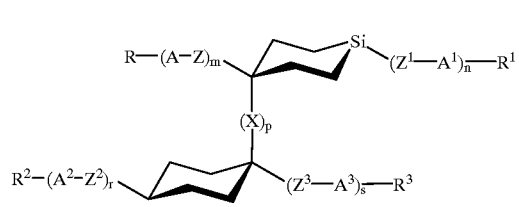
I7
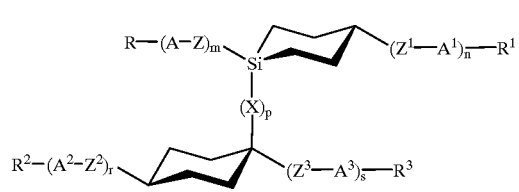
I8
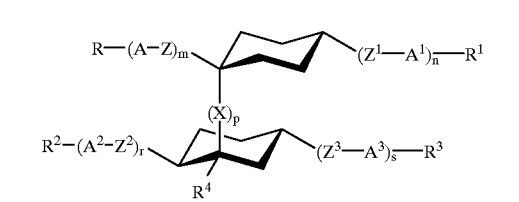
I9
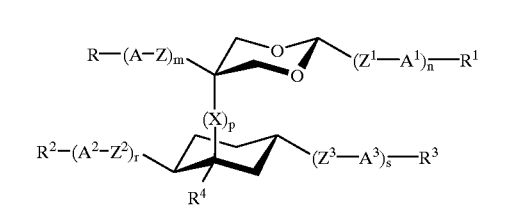
I10
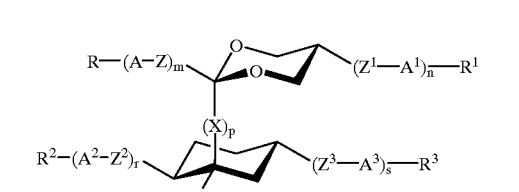
I11
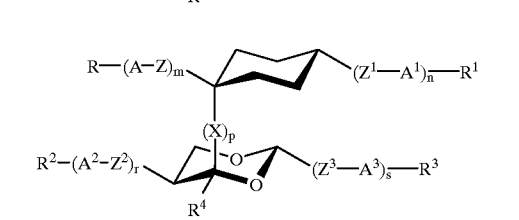
I12
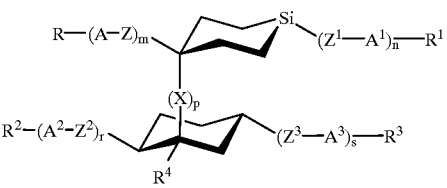
I13
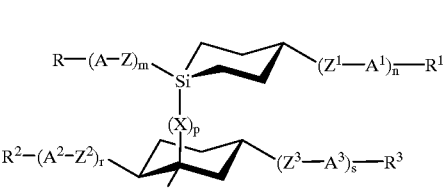
I14
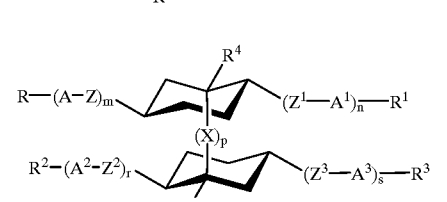
I15
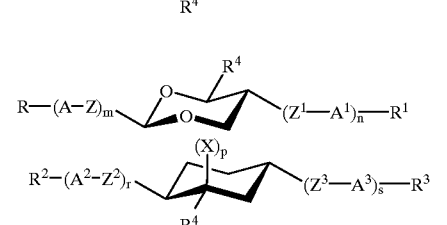
I16
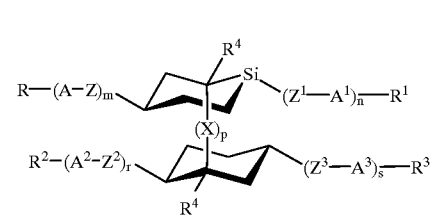
I17
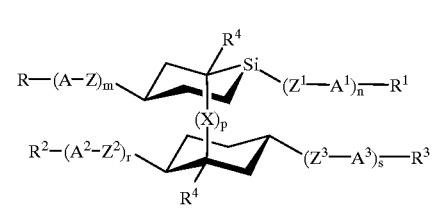
I18
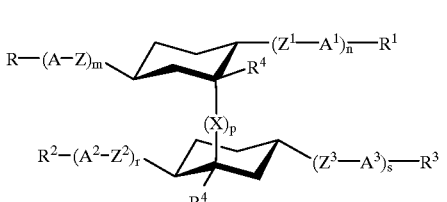
I19
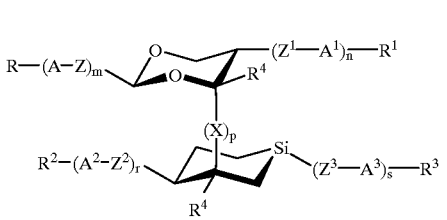
I20

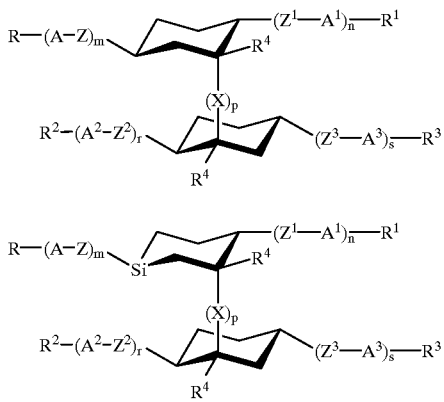

in which R, $R^1$, $R^2$, $R^3$, $R^4$, A, $A^1$, $A^2$, $A^3$, Z, $Z^1$, $Z^2$, $Z^3$, X, p, m, n, r and s are as defined above.

The compounds of the formulae I1 to I6 in particular are distinguished by having a wavelength-dependent inversion of the optical anisotropy and are therefore suitable for the production of optical switches or filters.

If R, $R^1$, $R^2$, $R^3$ and/or $R^4$ in the formulae above and below is an alkyl radical and/or an alkoxy radical, this can be straight-chain or branched. It is preferably straight-chain, has 2, 3, 4, 5, 6, or 7 carbon atoms and accordingly is preferably ethyl, propyl, butyl, pentyl, hexyl, heptyl, ethoxy, propoxy, butoxy, pentyloxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Where a $CH_2$ group in R, $R^1$, $R^2$, $R^3$ or $R^4$ is replaced by oxygen, i.e., oxaalkyl, oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R, $R^1$, $R^2$, $R^3$ and/or $R^4$ is an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R, $R^1$, $R^2$, $R^3$ and/or $R^4$ is an alkyl radical which is at least monosubstituted by halogen, this radical is preferably straight-chain and halogen is preferably F or Cl. In the case of polysubstitution, halogen is preferably F. The resultant radicals also include perfluorinated radicals. In the case of monosubstitution, the fluorine or chlorine substituent can be in any desired position, but is preferably in the ω-position.

Compounds of the formula I containing a branched wing group R, $R^1$, $R^2$, $R^3$ and/or $R^4$ may occasionally be of importance owing to better solubility in the customary liquid-crystalline base materials, but in particular as chiral dopants if they are optically active. Smectic compounds of this type are suitable as components of ferroelectric materials.

Branched groups of this type generally contain not more than one chain branch. Preferred branched radicals R, $R^1$, $R^2$, $R^3$ and/or $R^4$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy or 1-methylheptyloxy.

If R, $R^1$, $R^2$, $R^3$ and/or $R^4$ is an alkenyl radical this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- -7-enyl, non-1-, -2-, -3-, -4-, -5-, -6-, -7- or -8-enyl, or dec-1-, -2-, -3-, -4-, -5-, -6-, -7-, -8- or -9-enyl.

R, $R^1$, $R^2$, $R^3$ and/or $R^4$ are particularly preferably an alkenyl radical from the following group:

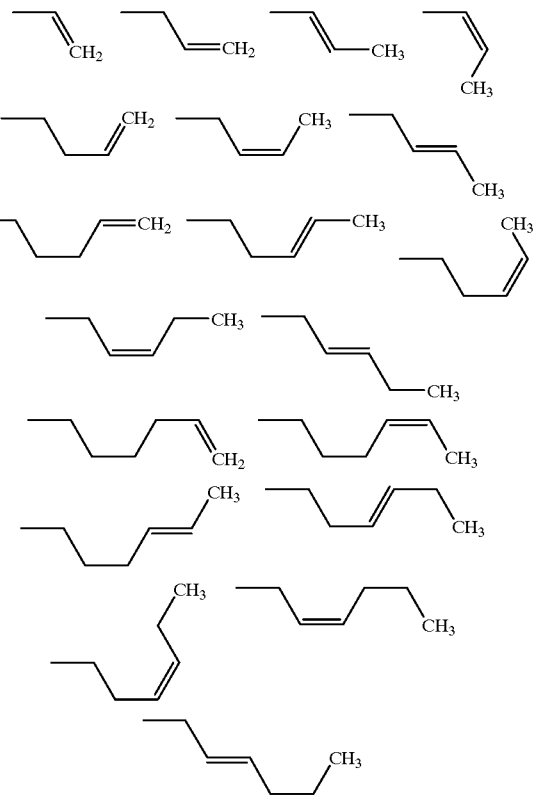

If R, $R^1$, $R^2$, $R^3$ and/or $R^4$ are an alkenyloxy radical, this can be straight-chain or branched. It is preferably straight-chain and has 2 to 10 carbon atoms. It is particularly preferably a radical from the following group:

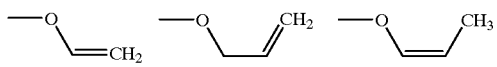

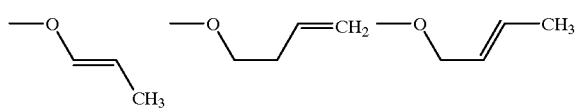
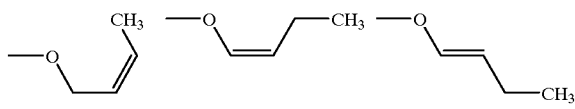
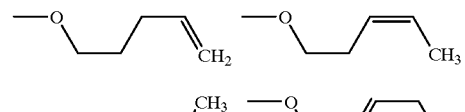
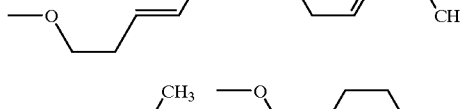
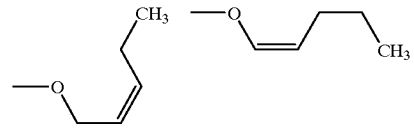
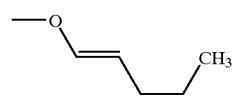

Formula I covers the racemates of these compounds and the optical antipodes, and mixtures thereof.

Of these compounds of the formula I and the sub-formulae, preference is given to those in which at least one of the radicals present therein has one of the preferred meanings indicated.

Some very particularly preferred smaller groups of compounds of the formula I are those of the sub-formulae I23 to I88:

I23
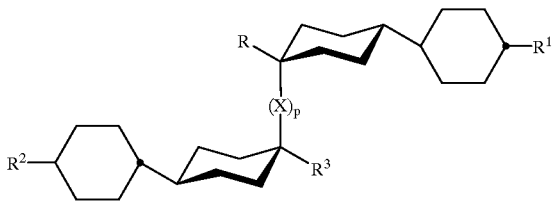

I24
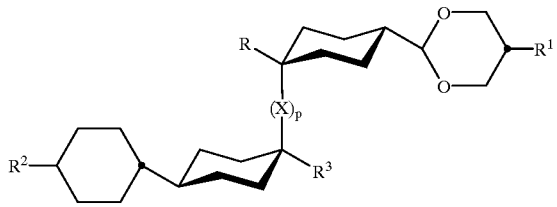

I25
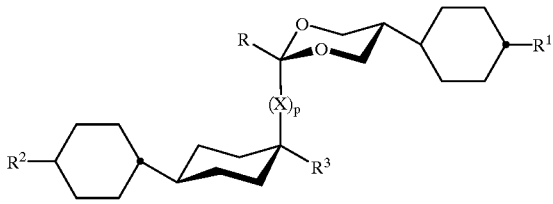

I26
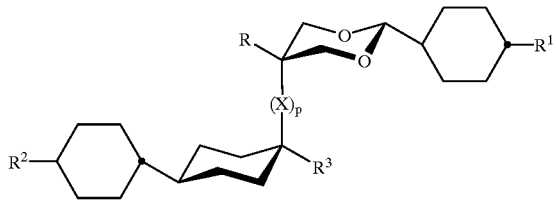

I27
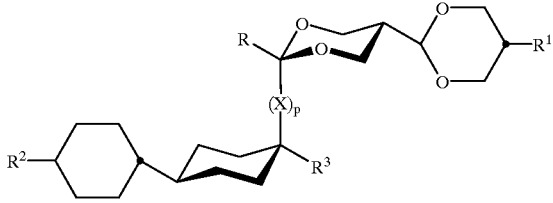

I28
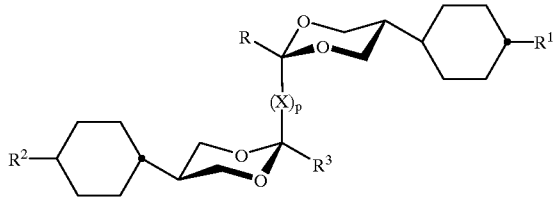

I29
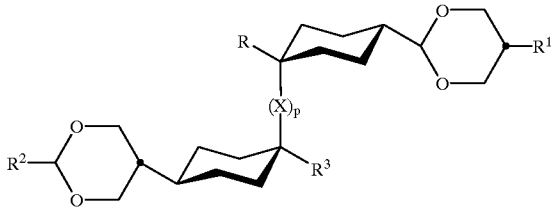

I30
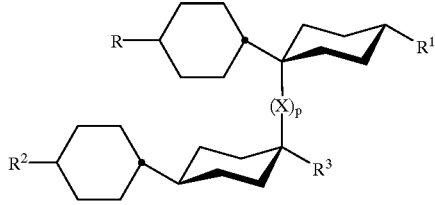

-continued
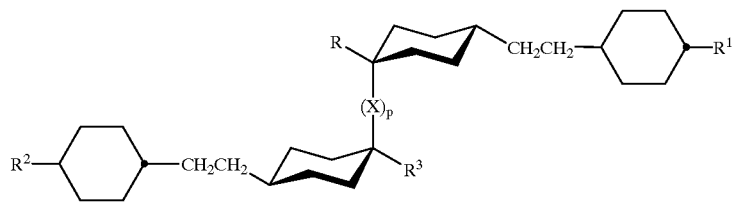
I31
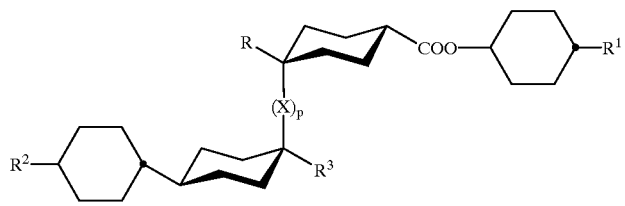
I32
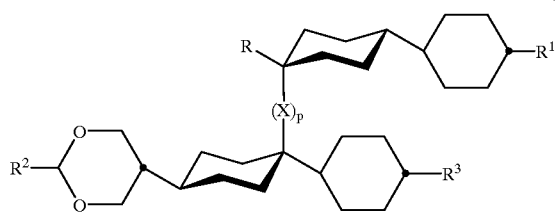
I33
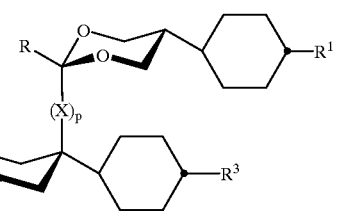
I34
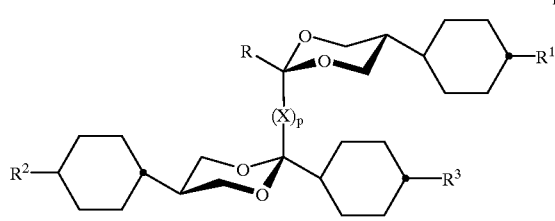
I35
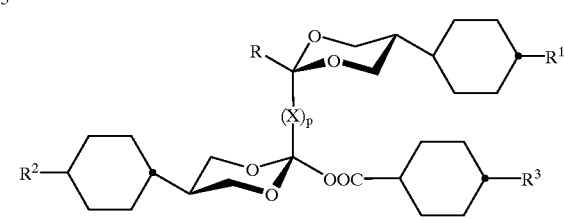
I36
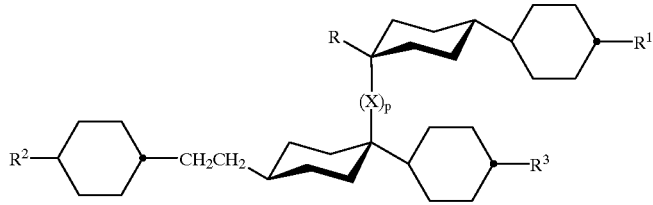
I37
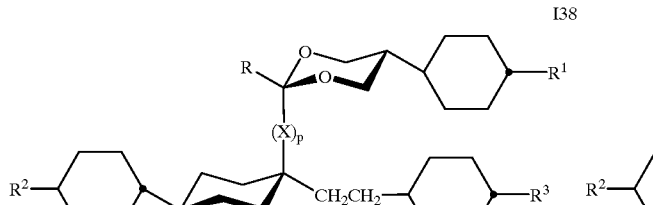
I38
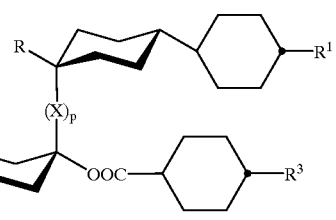
I39
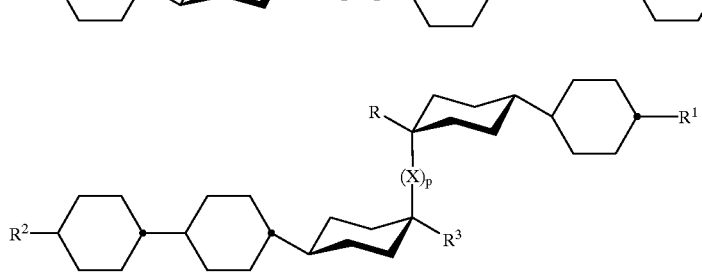
I40

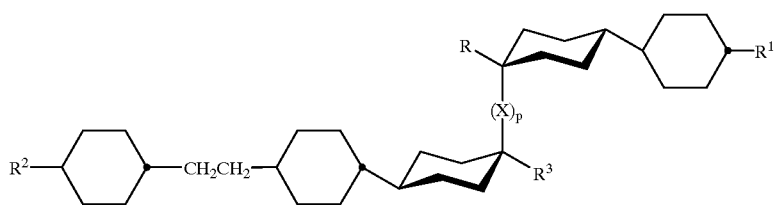
I41
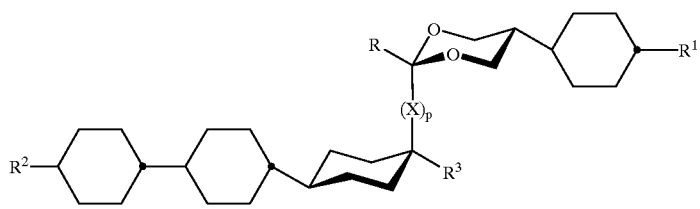
I42
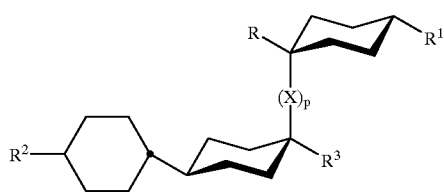
I43
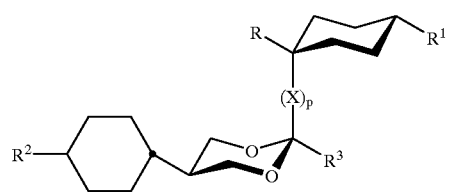
I44
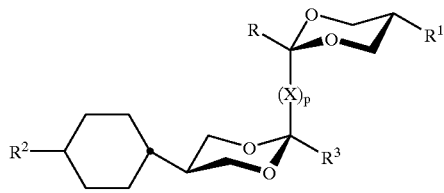
I45
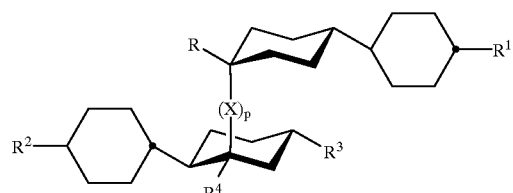
I46
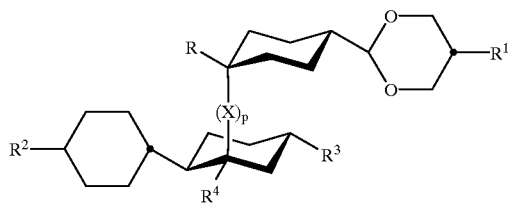
I47
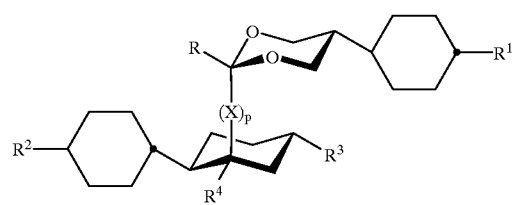
I48
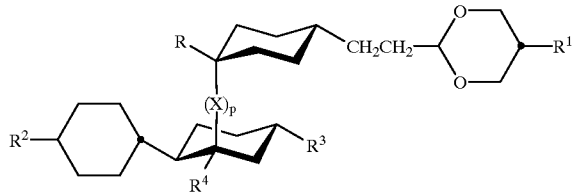
I49
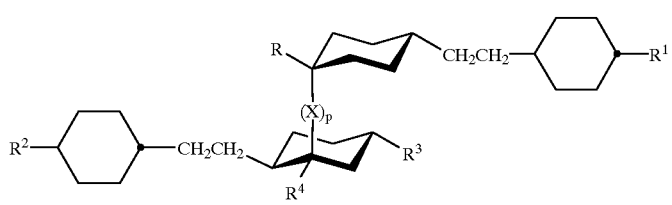
I50

I51
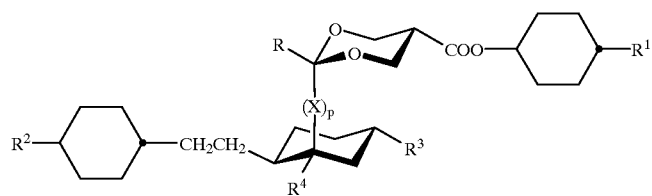
I52
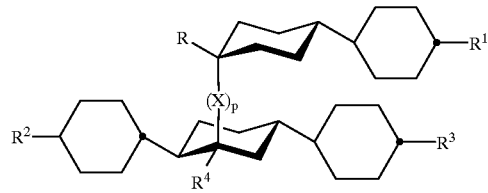
I53
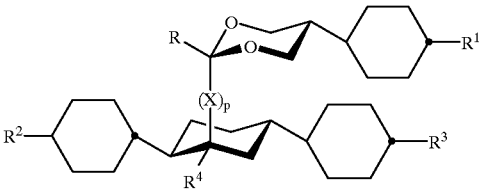
I54
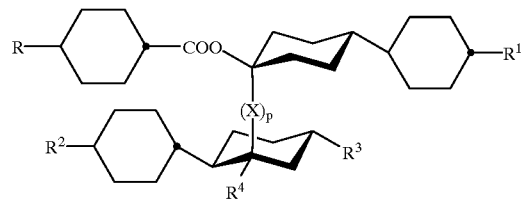
I55
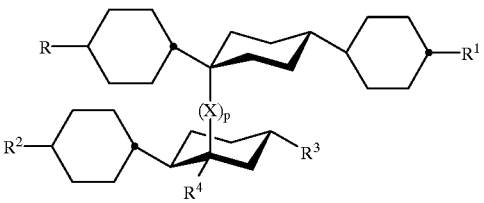
I56
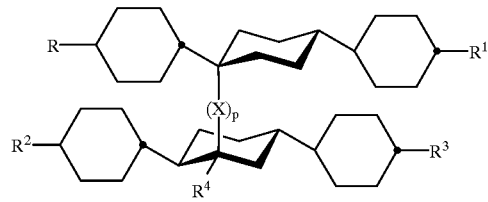
I57
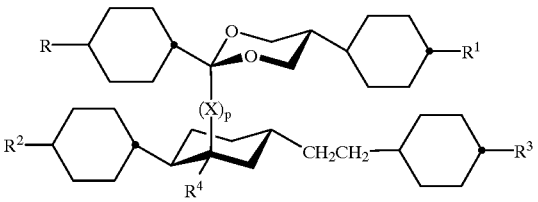
I58
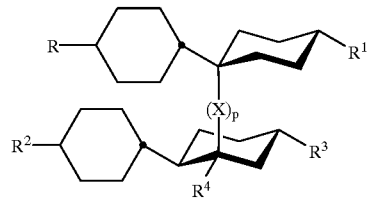
I59
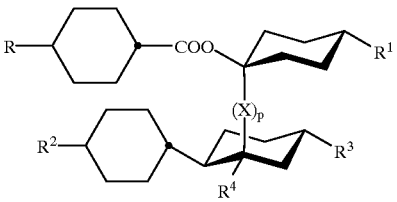
I60
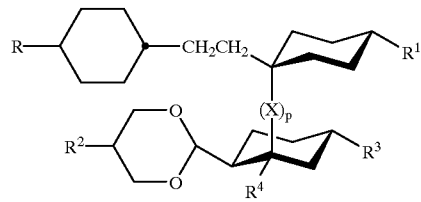
I61
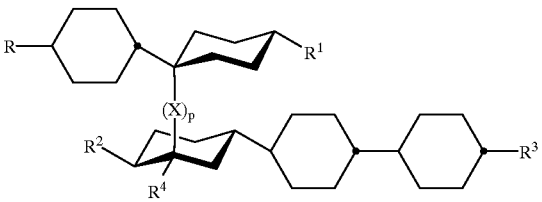
I62
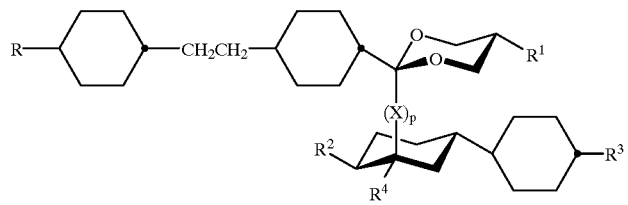

-continued
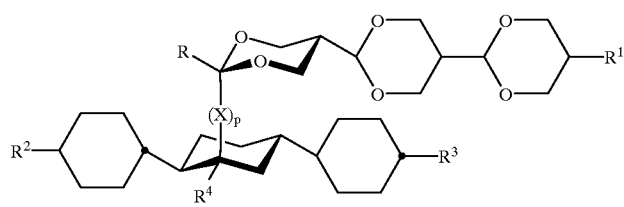
I63
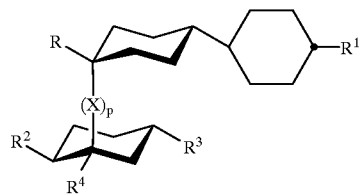
I64
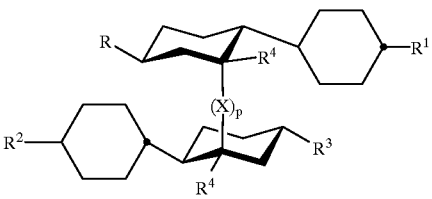
I65
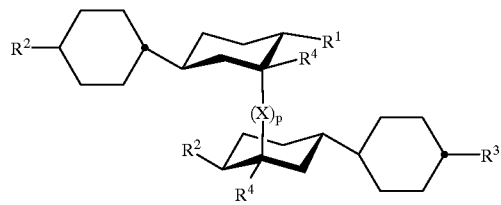
I66
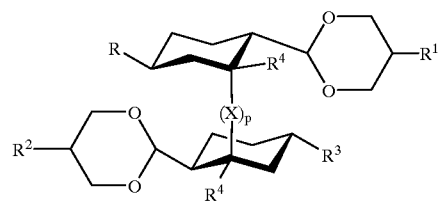
I67
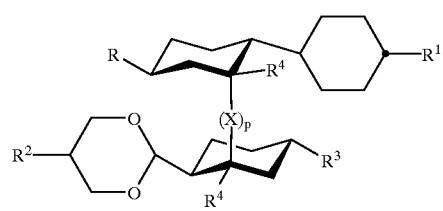
I68
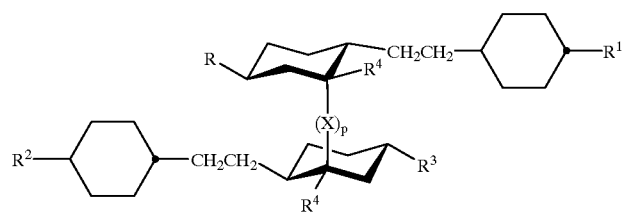
I69
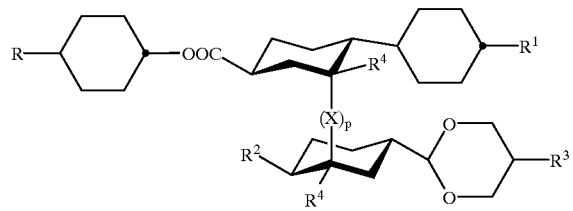
I70
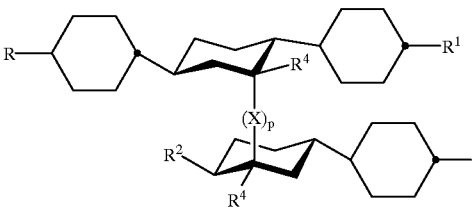
I71
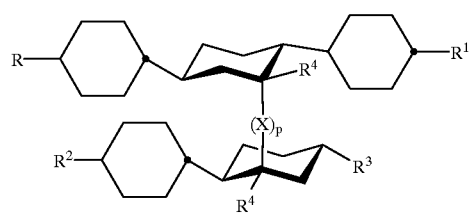
I72
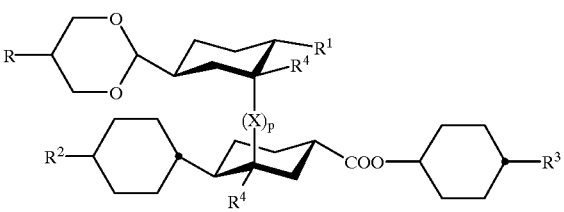
I73

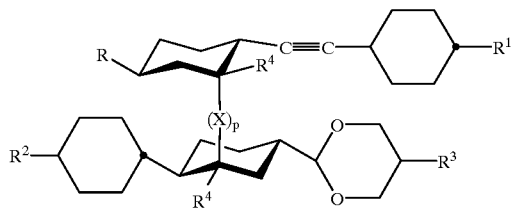
I74
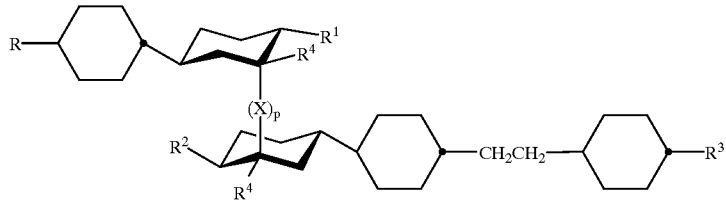
I75
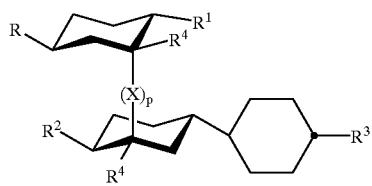
I76
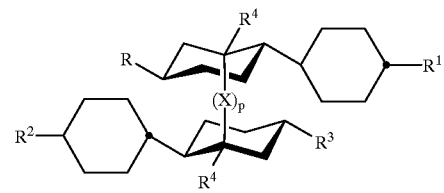
I77
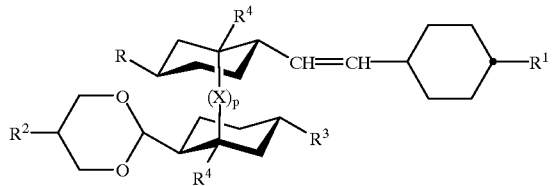
I78
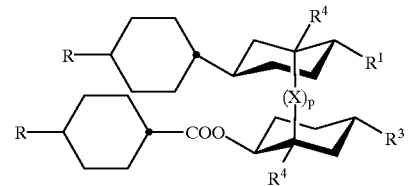
I79
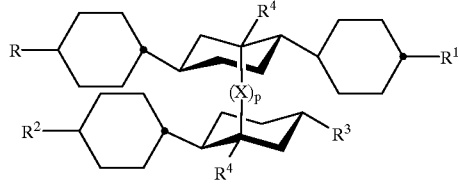
I80
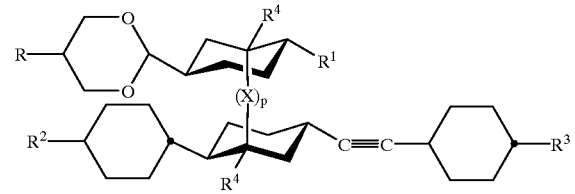
I81

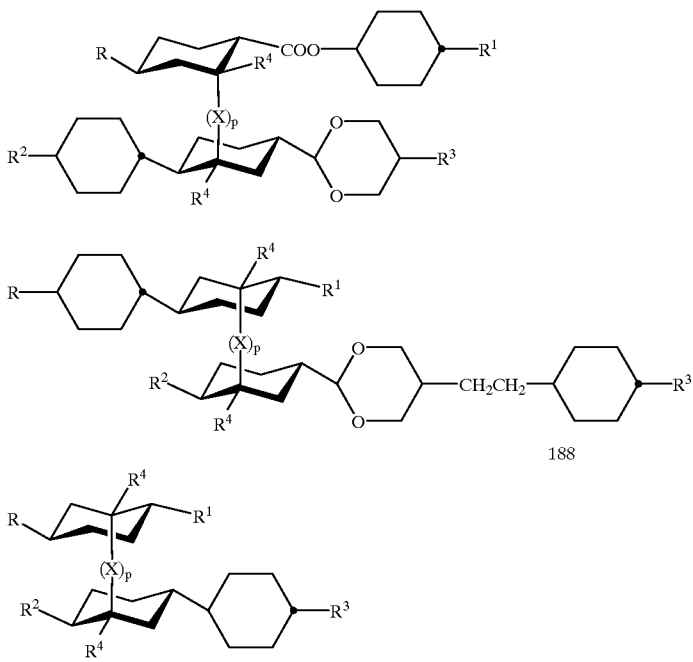

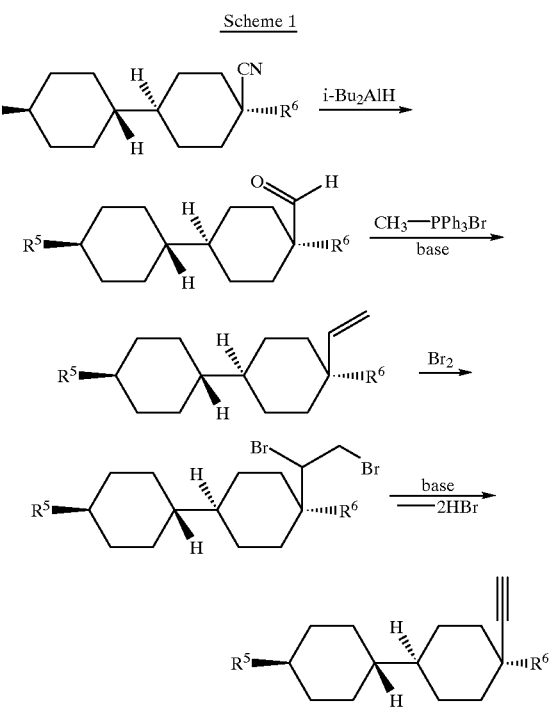

in which R, $R^1$, $R^2$, $R^3$, $R^4$, X and p are as defined above.

Very particularly preferred compounds from this group are those of the formulae I23, I25, I28, I31, I33 and I45, I47, I64, I65, I66, I76, I77 and I85.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions.

Use can be made here of variants which are known per se, but are not mentioned here in greater detail.

The starting materials can, if desired, also be formed in situ by not isolating them from the reaction mixture, but instead immediately converting them further into the compounds of the formula I.

The compounds of the formula I in which A, $A^1$, $A^2$ and/or $A^3$ is axially fluorinated cyclohexane can be synthesized using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis (1973) 779); G. A. Olah, X-Y. Li, Q. Wang, G. K. S. Prakash, Synthesis (1993) 693).

The compounds of the formula I in which B, $B^1$, A, $A^1$, $A^2$ or $A^3$ is a silacyclohexane radical can be synthesized, for example, analogously to B. T. Nguyen, F. K. Cartledge, J. Org. Chem. 51, 12, 1986, 2206–2210, and R. H. Peters, D. F. Crowe, M. Tanabe, M. A. Avery, W. K. M. Chong, J. Med. Chem. 30, 4, 1987, 646–652.

The compounds according to the invention can be prepared, for example, as shown in the following reaction schemes:

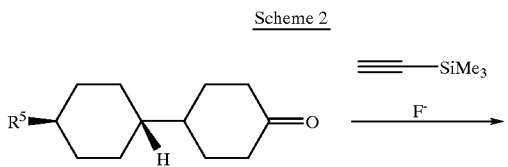

-continued
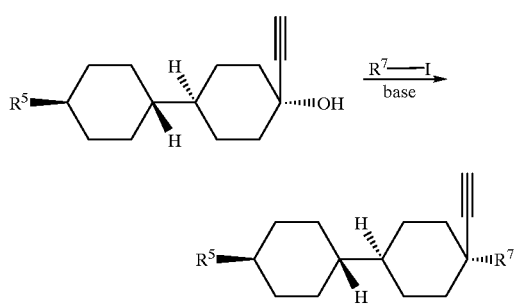
R[7]=alkyl or fluoroalkyl
Scheme 3
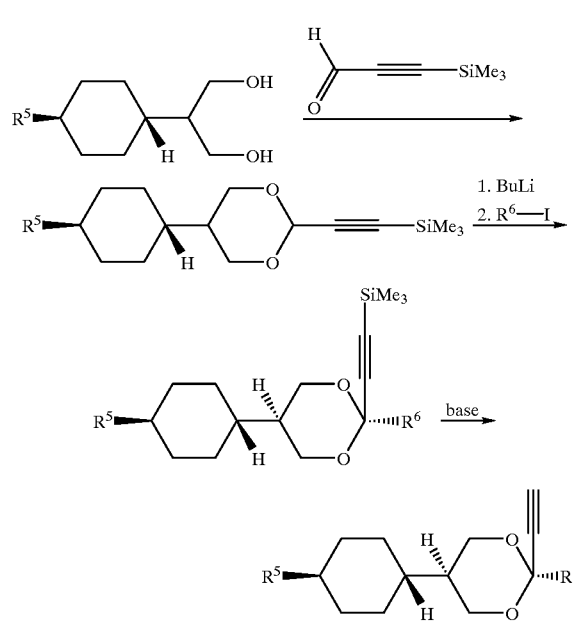
Scheme 4
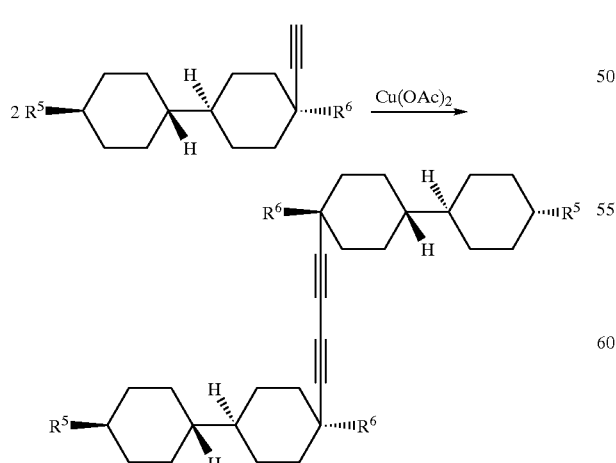
Scheme 5
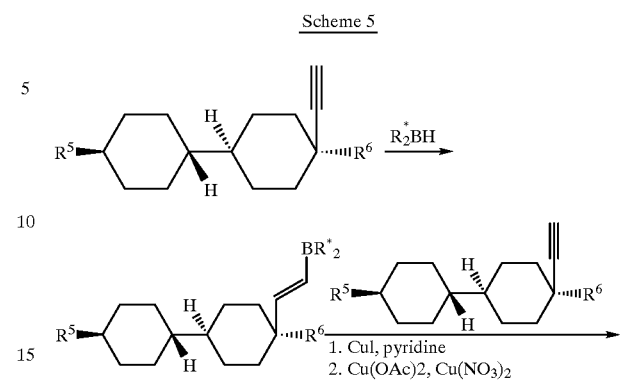
R* = alkyl
Scheme 6
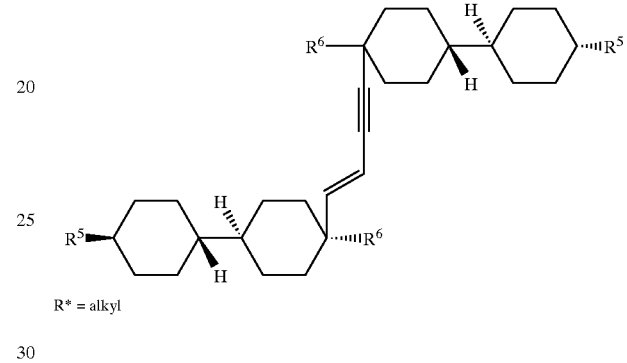
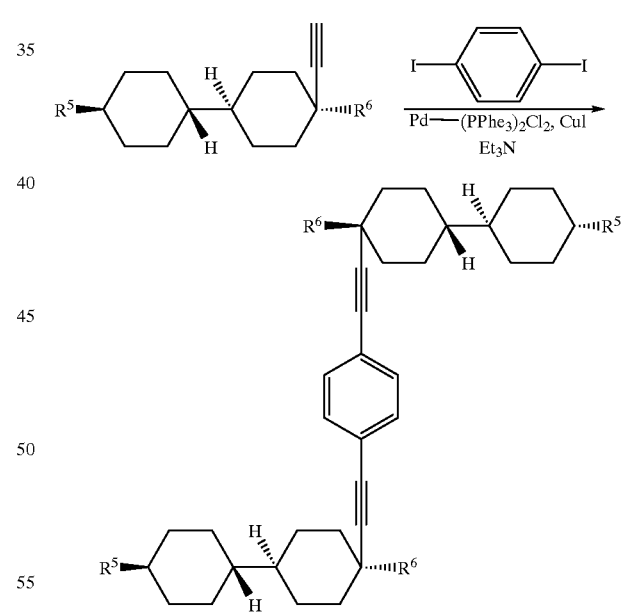
Scheme 7
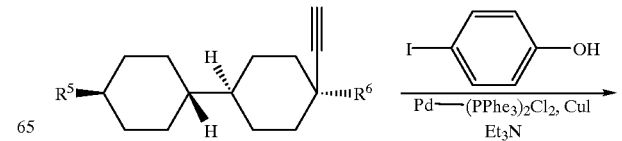

-continued
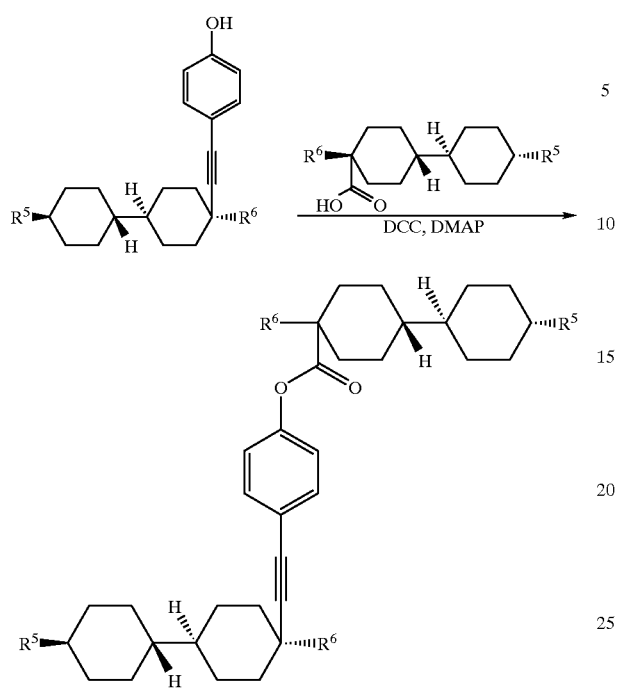
Scheme 8
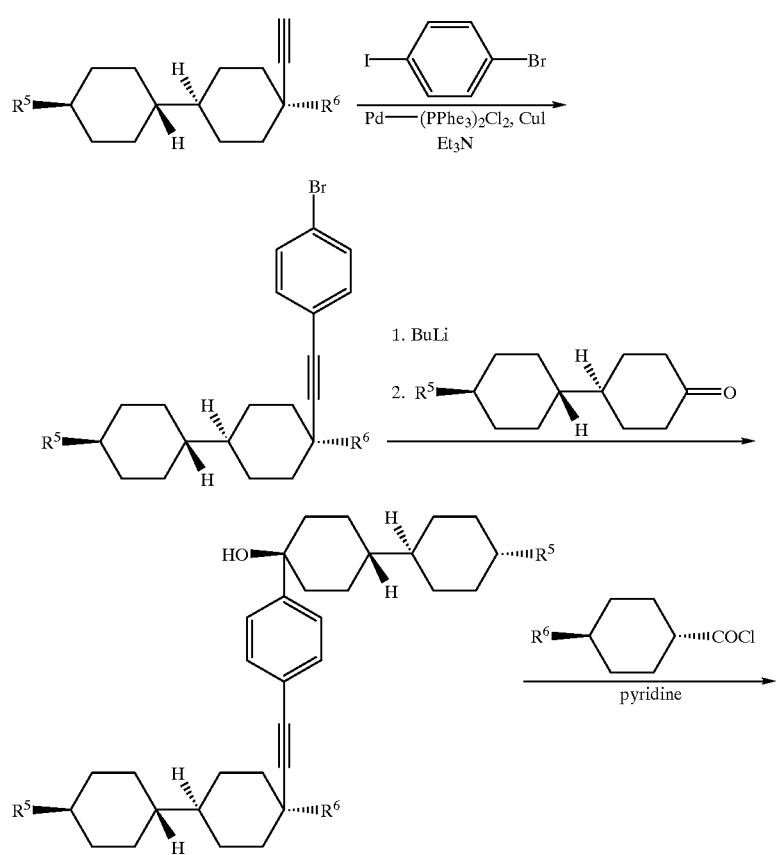

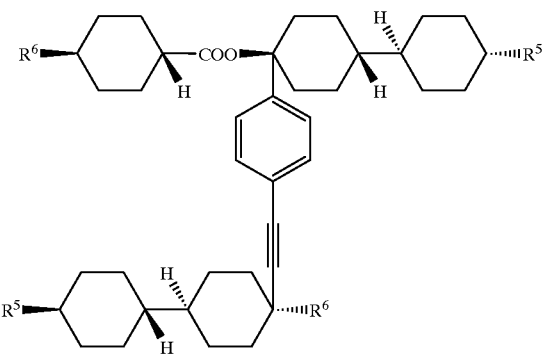
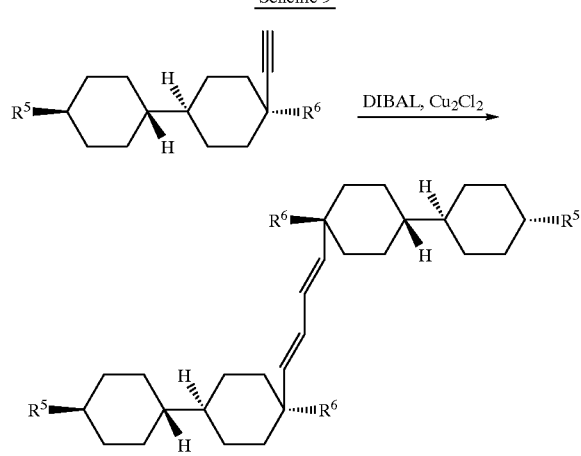
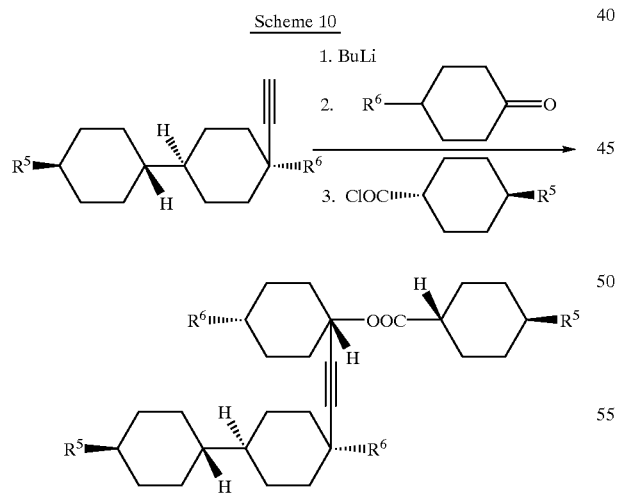
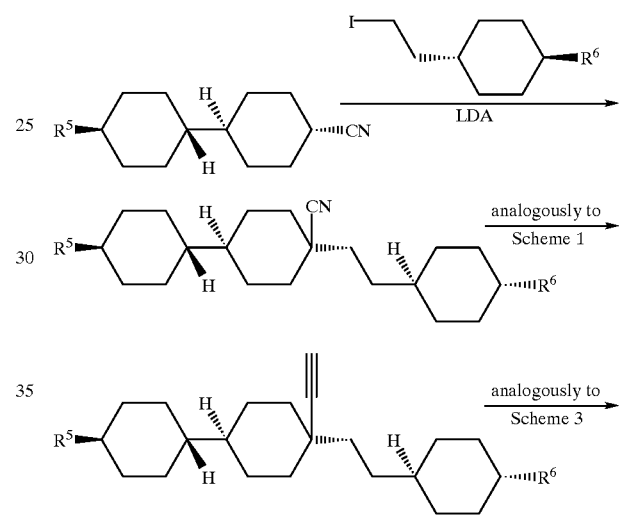
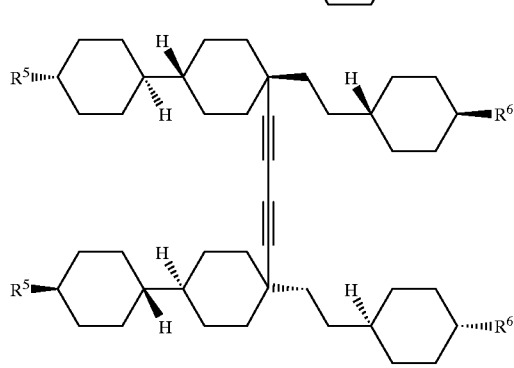

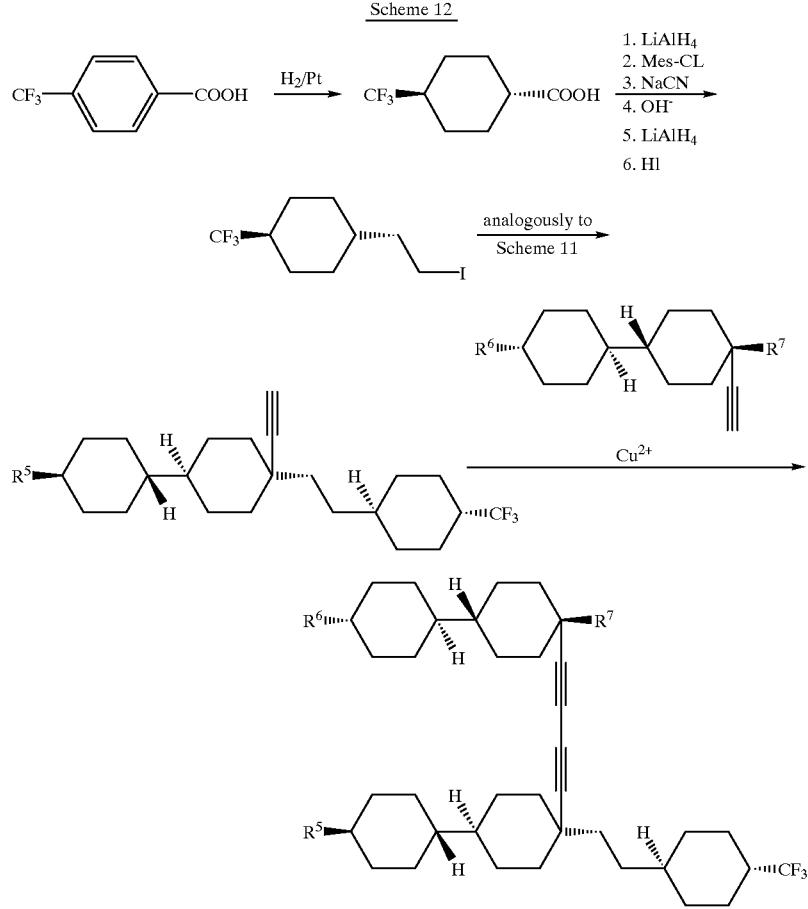
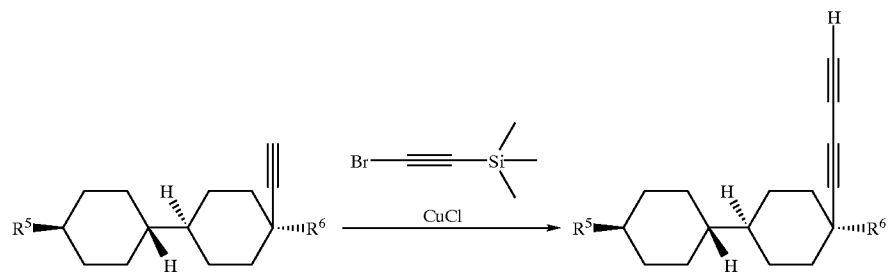

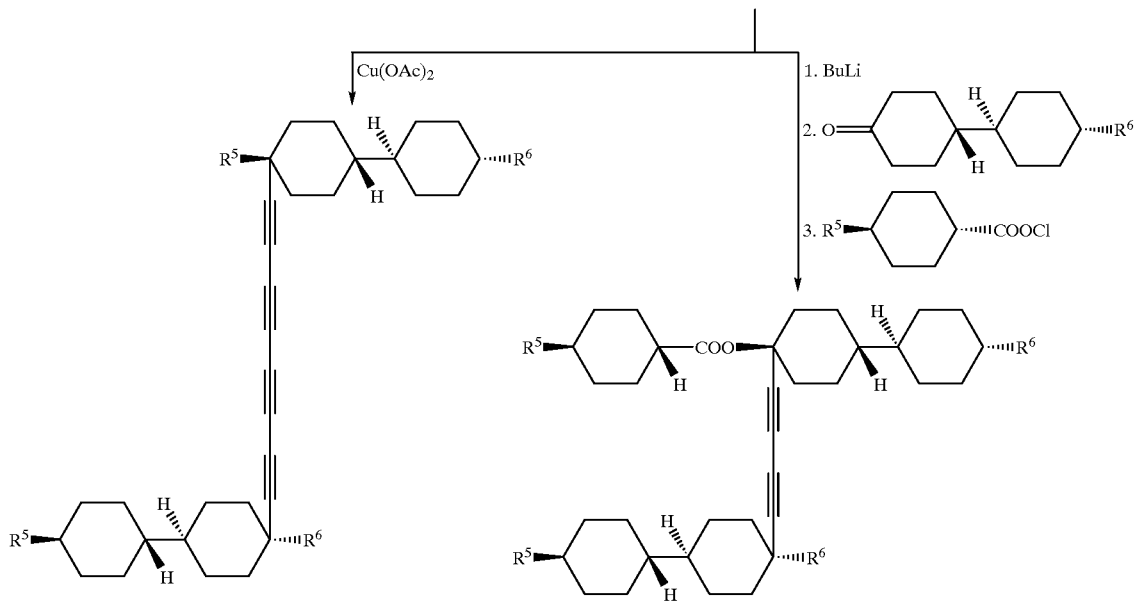
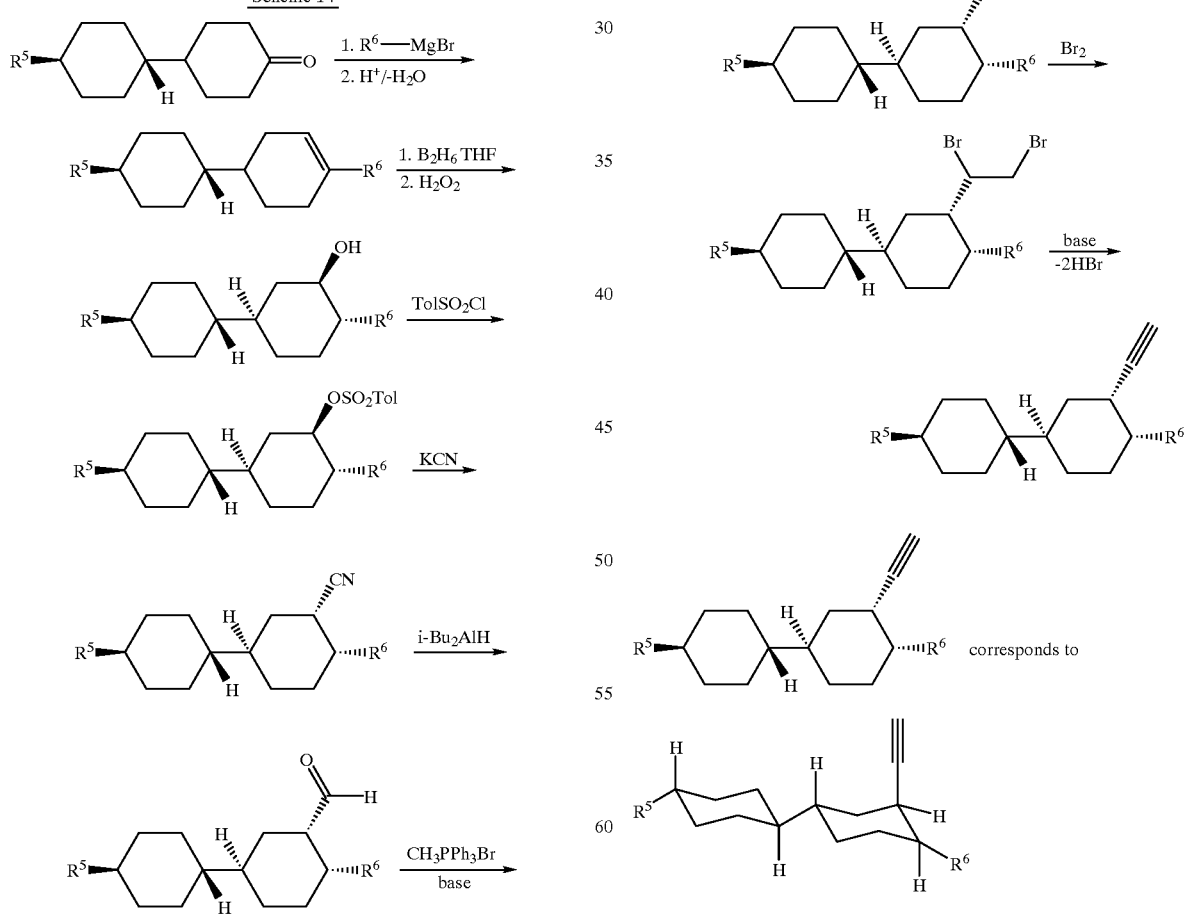

TolSO$_2$Cl=toluenesulfonyl chloride
Scheme 15
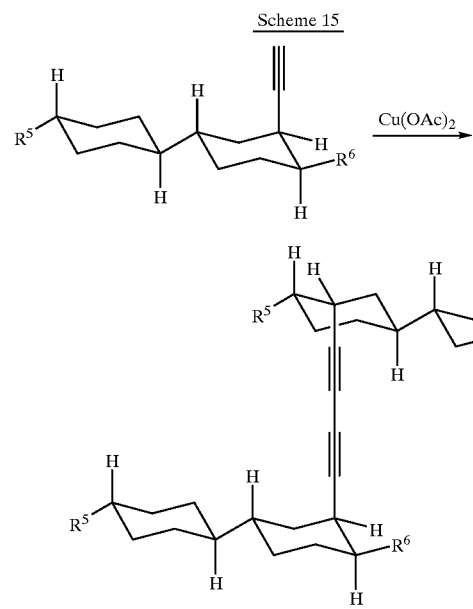
Scheme 16
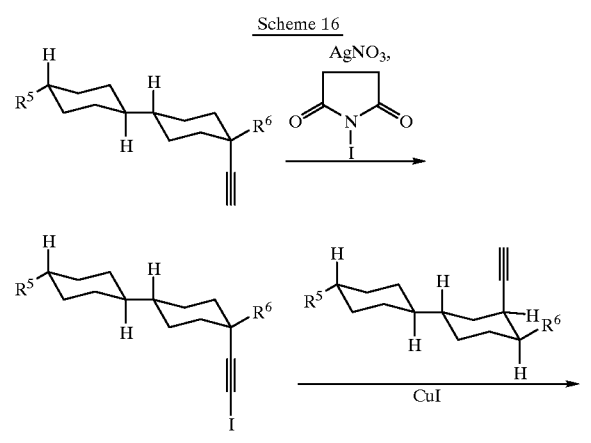
Scheme 17
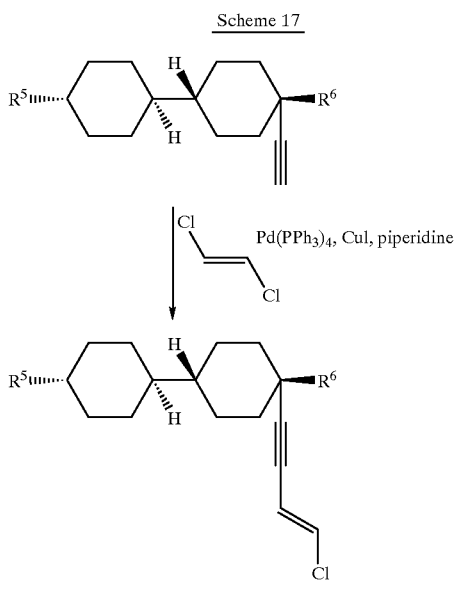
The reactions in accordance with Scheme 17 can be carried out, for example, analogously to Alami et al., Tetrahedron Letters, Vol. 35, 3543–3544, 1994.
Scheme 18
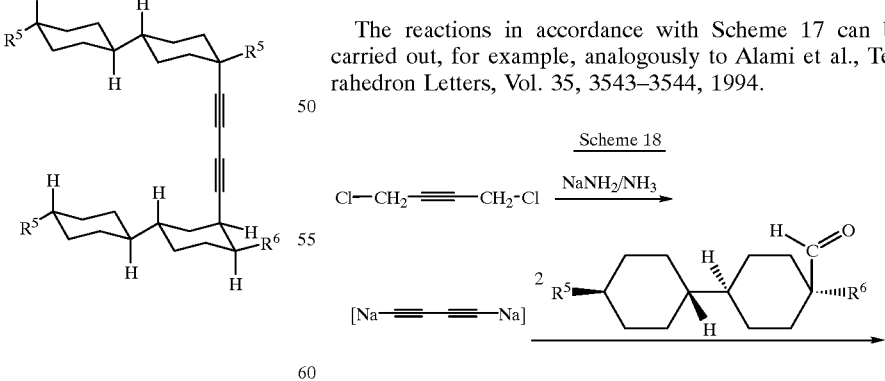

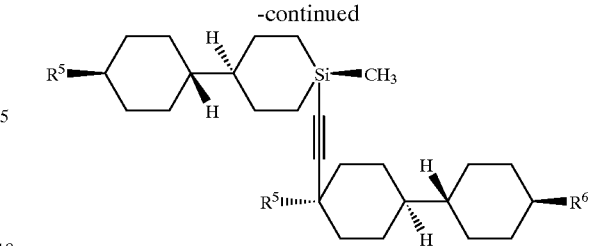

in which $R^5$ and $R^6$ are as defined above.

Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known processes.

Suitable reactive derivatives of said carboxylic acids are in particular the acid halides, especially the chlorides and bromides, furthermore the anhydrides, azides or esters, in particular alkyl esters having 1–4 carbon atoms in the alkyl group.

Suitable reactive derivatives of said alcohols or phenols are in particular the corresponding metal alkoxides or phenoxides respectively, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulfoxides, such as dimethyl sulfoxide or sulfolane. Water-immiscible solvents can at the same time advantageously be used for removal by azeotropic distillation of the water formed during the esterification. It may in some cases also be possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are generally complete after from 15 minutes to 48 hours.

In detail, the reaction conditions for the esterification depend substantially on the nature of the starting materials used. Thus, the reaction of a free carboxylic acid with a free alcohol or phenol is generally carried out in the presence of a strong acid, for example a mineral acid, such as hydrochloric acid or sulfuric acid. A preferred reaction procedure is to react an acid anhydride or, in particular, an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline-earth metal hydroxides, such as calcium hydroxide, or organic bases, such as triethylamine, pyridine, lutidine, collidine or quino-

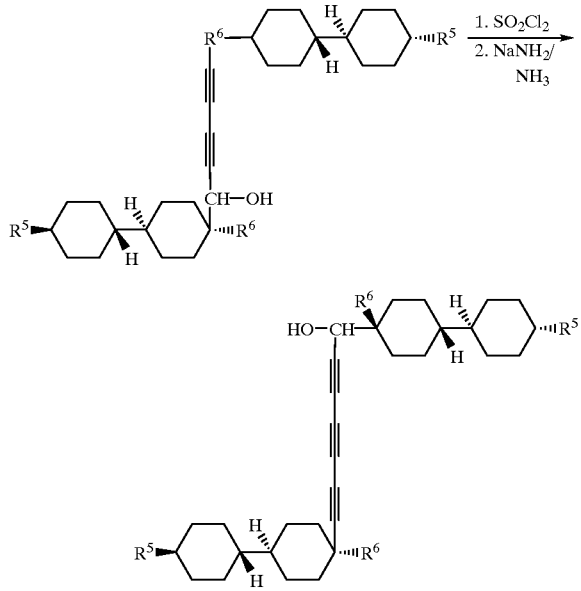

The corresponding tetrayne is obtained in an analogous manner using

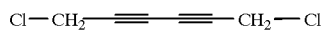

(Bohlmann, Chem. Berichte, Vol. 86, No. 5, 1953, 663–664).

Scheme 19

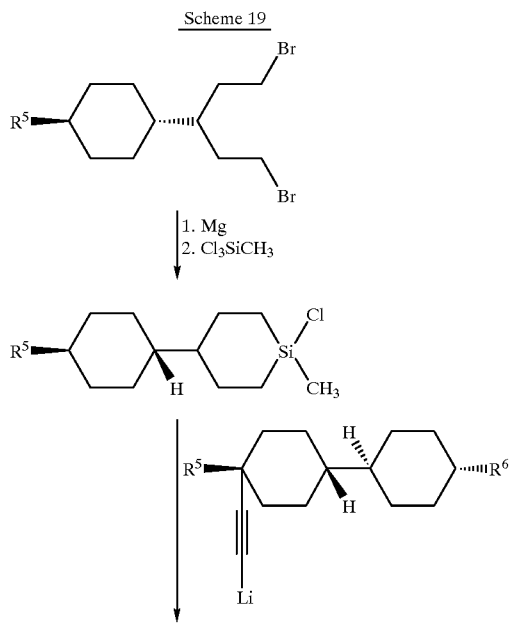

line. A further preferred embodiment of the esterification comprises first converting the alcohol or phenol into the sodium or potassium alkoxide or phenoxide, for example by treatment with ethanolic sodium hydroxide or potassium hydroxide solution, and isolating the product and reacting it with an acid anhydride or, in particular, acid chloride.

Nitriles can be obtained by replacement of halogens using copper cyanide or alkali metal cyanide.

In a further process for the preparation of compounds of the formula I which contain a group of the formula

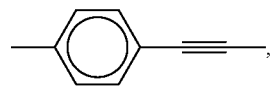

an aryl halide is reacted with an alkyne in the presence of a base and in the presence of a palladium catalyst. Examples of suitable aryl halides are chlorides, bromides and iodides, in particular bromides and iodides. The base necessary for the success of the coupling reaction, such as, for example, triethylamine, is also suitable as solvent. Examples of suitable palladium catalysts are its salts, in particular Pd(II) acetate, wirh organophosphorus(III) compounds, such as, for example, triarylphosphines.

This process can be carried out in the presence or absence of an inert solvent at temperatures between about 0° C. and 150° C., preferably between 20° C. and 100° C.; suitable solvents are, for example, nitriles, such as acetonitrile, or hydrocarbons, such as benzene or toluene. The aryl halides and alkynes employed as starting materials are frequently commercially available or can be prepared by processes known from the literature, for example by halogenation of corresponding parent compounds or by elimination reactions on corresponding alcohols or halides.

Coupling reactions of alkynyl compounds with aryl halides can be carried out analogously to the process described by A. O. King, E. Negishi, F. J. Villani and A. Silveira in J. Org. Chem. 43, 358 (1978).

Ethers of the formula I are obtainable by etherification of corresponding hydroxyl compounds, preferably corresponding phenols, the hydroxyl compound advantageously first being converted into a corresponding metal derivative, for example into the corresponding alkali metal alkoxide or alkali metal phenoxide, by treatment with NaH, $NaNH_2$, NaOH, KOH, $Na_2CO_3$ or $K_2CO_3$. This metal derivative can then be reacted with the appropriate alkyl halide, alkyl sulfonate or dialkyl sulfate, advantageously in an inert solvent, such as, for example, acetone, 1,2-dimethoxyethane, DMF or dimethyl sulfoxide, or alternatively with an excess of aqueous or aqueous-alcoholic NaOH or KOH, at temperatures between about 20° C. and 100° C.

The linking of an aromatic ring to a non-aromatic ring or of two non-aromatic rings is preferably carried out by condensation of an organolithium or organomagnesium compound with a ketone if an aliphatic group Z, $Z^1$, $Z^2$ and/or $Z^3$ is to be between the rings.

The organometallic compounds are prepared, for example, by metal-halogen exchange (for example in accordance with Org. React. 6, 339–366 (1951)) between the corresponding halogen compound and an organolithium compound, such as, preferably, tert-butyl lithium or lithium naphthalenide, or by reaction with magnesium turnings.

In addition, the compounds of the formula I can be prepared by reducing a compound which contains one or more reducible groups and/or C—C bonds in place of H atoms, but otherwise conforms to the formula I.

Suitable reducible groups are preferably carbonyl groups, in particular keto groups, furthermore, for example, free or esterified hydroxyl groups or aromatically bonded halogen atoms. Preferred starting materials for the reduction are compounds which conform to the formula I, but contain a cyclohexene ring or cyclohexanone ring in place of a cyclohexane ring and/or contain a —CH=CH— group in place of a —$CH_2CH_2$— group and/or contain a —CO— group in place of a —$CH_2$— group and/or contain a free or functionally derived (for example in the form of its p-toluenesulfonate) OH group in place of an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which may be employed in the form of oxides (for example $PtO_2$ or PdO), on a support (for example Pd on carbon, calcium carbonate or strontium carbonate) or in finely divided form.

Ketones can also be reduced by the methods of Clemmensen (using zinc, zinc amalgam or tin and hydrochloric acid, advantageously in aqueous-alcoholic solution or in the heterogeneous phase with water/toluene at temperatures between about 80 and 120°) or Wolff-Kishner (using hydrazine, advantageously in the presence of alkali, such as KOH or NaOH, in a high-boiling solvent, such as diethylene glycol or triethylene glycol, at temperatures between about 100 and 200°) to give the corresponding compounds of the formula I which contain alkyl groups and/or —$CH_2CH_2$— bridges.

Furthermore, reductions using complex hydrides are possible. For example, arylsulfonyloxy groups can be removed reductively using $LiAlH_4$, in particular p-toluenesulfonyloxymethyl groups can be reduced to methyl groups, advantageously in an inert solvent, such as diethyl ether or THF, at temperatures between about 0 and 100°. Double bonds can be hydrogenated using $NaBH_4$ or tributyltin hydride in methanol.

The starting materials are either known or can be prepared analogously to known compounds.

The liquid-crystalline media according to the invention preferably comprise from 2 to 40 components, in particular from 4 to 30 components, as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexanecarboxylates and cyclohexylcyclohexanecarboxylates, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are denoted by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is called group B, R" is —F, —Cl, —NCS or —(O)$_i$CH$_{3-(k+l)}$F$_k$Cl$_l$, where i is 0 or 1, and k and l are 1, 2 or 3; the compounds in which R" has this meaning are denoted by the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is called group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably:

Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5%–90% and in particular from 10% to 90%.

The media according to the invention preferably comprise from 1 to 40%, particularly preferably from 5 to 30%, of the compounds according to the invention. Further preferred media are those which comprise more than 40%, in particular from 45 to 90%, of compounds according to the invention.

The media preferably comprise three, four or five compounds according to the invention.

The media according to the invention are prepared in a manner which is customary per se. In general, the components are dissolved in one another, advantageously at elevated temperature. By means of suitable additives, the liquid-crystalline phases can be modified in accordance with the invention in such a manner that they can be used in all types of liquid-crystal display elements which have been disclosed hitherto. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight. m.p. denotes melting point, cl.p.=clearing point, and Tg=glass transition temperature. Furthermore, C=crystalline state, N=nematic phase, Sm=smectic phase and I=isotropic phase. The numbers between these symbols indicate the conversion temperatures. Δn denotes the optical anisotropy (589 nm, 20° C.) and Δε the dielectric anisotropy (1 kHz, 20° C.)

The Δn and Δε values of the compounds according to the invention were obtained by extrapolation from liquid-crystalline mixtures consisting of 10% of the particular compound according to the invention and 90% of the commercially available liquid crystal ZLI 4792 (Merck, Darmstadt).

The viscosity ($mm^2$/sec) was determined at 20° C.

"Conventional work-up" means that water is added if necessary, the mixture is extracted with methylene chloride, diethyl ether or toluene, the phases are separated, the organic phase is dried and evaporated, and the product is purified by distillation under reduced pressure or crystallization and/or chromatography.

The following abbreviations are used:
THF tetrahydrofuran
KOtBu potassium tert-butoxide
RT room temperature
MTB ether methyl tert-butyl ether

EXAMPLE 1

4-[4-(4,4'-Dipentylbicyclohexyl-4-yl)buta-1,3-diynyl]-4,4'-dipentylbicyclohexyl a) 4,4'-Dipentylbicyclohexyl-4-carbaldehyde 61.00 g of 4,4'-dipentylbicyclohexyl-4-carbonitrile (for example obtainable in accordance with EP 0 107 759), dissolved in 225 ml of toluene, are slowly added dropwise to a 16.5% solution of diisobutylaluminium hydride in hexane. The reaction mixture is stirred at RT for 2 hours and subsequently poured into a mixture of ice and dilute hydrochloric acid. The resultant mixture is stirred for 1 hour, extracted with toluene and subjected to conventional work-up, giving 4,4'-dipentylbicyclohexyl-4-carbaldehyde.

b) 4,4'-Dipentyl-4-vinylbicyclohexyl

A solution of 17.84 g of KOtBu in 100 ml of THF is added dropwise at 0° C. to a suspension of 53.20 g of 4,4'-dipentylbicyclohexyl-4-carbaldehyde and 56.80 g of methyltriphenylphosphonium bromide in 300 ml of THF. The mixture is stirred at RT overnight, water is added, and the mixture is extracted with MTB ether. The combined organic phases are subjected to conventional work-up, giving 4,4'-dipentyl-4-vinylbicyclohexyl.

c) 4-(1,2-Dibromoethyl)-4,4'-dipentylbicyclohexyl 4.754 ml of bromine are added dropwise at from 0° C. to −10° C. to 36.40 g of 4,4'-dipentyl-4-vinylbicyclohexyl in 120 ml of diethyl ether. After 1 hour without cooling, water is added to the reaction mixture, which is subjected to conventional work-up, giving 4-(1,2-dibromoethyl)-4,4'-dipentylbicyclohexyl.

d) 4-Ethynyl-4,4'-dipentylbicyclohexyl 32.48 g of KOtBu are added at RT to 47.50 g of 4-(1,2-dibromoethyl)-4,4'-dipentylbicyclohexyl in 150 ml of tert-butanol. The mixture is heated to 60° C. and stirred at this temperature overnight. Water is subsequently added to the reaction mixture, which is acidified with dilute hydrochloric acid and subjected to conventional work-up, giving 4-ethynyl-4,4'-dipentylbicyclohexyl.

e) 4-[4-(4,4'-Dipentylbicyclohexyl-4-yl)buta-1,3-diynyl]-4,4'-dipentylbicyclohexyl A mixture of 5.00 g of 4-ethynyl-4,4'-dipentylbicyclohexyl, 12.5 ml of pyridine, 12.5 ml of methanol and 3.635 g of copper(II) acetate monohydrate is stirred at RT for 1.5 hours and subsequently heated at the boil. The mixture is stirred for 10 hours and subjected to conventional work-up, giving 4-[4-(4,4'-dipentylbicyclohexyl-4-yl)buta-1,3-diynyl]-4,4'-dipentylbicyclohexyl (C 77 SmB 198 I, $\Delta n=0.013$, $\Delta\epsilon=-0.27$).

EXAMPLE 2

4-[4-(4,4'-Dipentylbicyclohexyl-4-yl)buta-1,3-diynyl]-4-methoxy-4'-propylbicyclohexyl and 4-[4-(4-methoxy-4'-propylbicyclohexyl-4-yl)buta-1,3-diynyl]-4-methoxy-4'-propylbicyclohexyl a) 4-Ethynyl-4'-propylbicyclohexyl-4-ol 24.32 ml of (trimethylsilyl)acetylene are added dropwise at −30° C. to a solution of 30.0 g of 4'-propylbicyclohexyl-4-one and 3.41 g of tetrabutylammonium fluoride trihydrate in 300 ml of THF. The cooling bath is removed after 5 minutes, and the reaction mixture is stirred at RT for 2 hours. A suspension of 39.2 g of potassium fluoride in methanol is subsequently added, and the mixture is stirred at RT for 3 days. Conventional work-up gives 4-ethynyl-4'-propylbicyclohexyl-4-ol.

b) 4-Ethynyl-4-methoxy-4'-propylbicyclohexyl 28.85 ml of a 15% solution of butyllithium in hexane are added dropwise to a solution, cooled to −30° C., of 13.0 g of 4-ethynyl-4'-propylbicyclohexyl-4-ol in 24 ml of THF. A solution of 4.67 ml of iodomethane in 36 ml of dimethyl sulfoxide is subsequently added dropwise to the reaction mixture at −5° C. The mixture is stirred at RT overnight and subjected to conventional work-up, giving 4-ethynyl-4-methoxy-4'-propylbicyclohexyl.

c) 4-[4-(4,4'-Dipentylbicyclohexyl-4-yl)buta-1,3-diynyl]-4-methoxy-4'-propylbicyclohexyl and 4-[4-(4-methoxy-4'-propylbicyclohexyl-4-yl)buta-1,3-diynyl]-4-methoxy-4'-propylbicyclohexyl 4.00 g of 4-ethynyl-4-methoxy-4'-propylbicyclohexyl, 5.04 g of 4-ethynyl-4,4'-dipentylbicyclohexyl, 10.65 g of copper(II) acetate monohydrate and 0.145 g of copper(I) iodide are refluxed overnight in a mixture of 25 ml of pyridine and 25 ml of methanol. Conventional work-up gives a mixture of the three coupling products 4-[4-(4,4'-dipentylbicyclohexyl-4-yl)buta-1,3-diynyl]-4-methoxy-4'-propylbicyclohexyl (C 76 N 136 I, $\Delta\epsilon=0.95$, $\Delta n=0.006$), 4-[4-(4,4'-dipentylbicyclohexyl-4-yl)buta-1,3-diynyl]-4,4'-dipentylbicyclohexyl and 4-[4-(4-methoxy-4'-propylbicyclohexyl-4-yl)buta-1,3-diynyl]-4-methoxy-4'-propylbicyclohexyl (C 121 N (80) I, $\Delta\epsilon=-1.77$, $\Delta n=-0.002$), which can easily be separated by chromatography.

The following compounds according to the invention are obtained analogously from the corresponding precursors:

EXAMPLES 3–24, 24a), 24b)

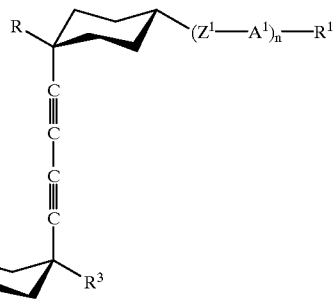

| | R | $(Z^1{-}A^1)_n{-}R^1$ | $R^2{-}(A^2{-}Z^2)_r$ | $R^3$ |
|---|---|---|---|---|
| 3) | n-Propyl | ⌬—n-Pentyl | n-Pentyl—⌬ | n-Propyl |
| 4) | n-Propyl | ⌬—CF$_3$ | CF$_3$—⌬ | CF$_3$ |
| 5) | —CH=CF$_2$ | ⌬—n-Pentyl | CF$_3$—⌬—CH$_2$CH$_2$— | —CH=CF$_2$ |
| 6) | —CH$_2$CH=CH$_2$ | ⌬—n-Propyl | n-Pentyl—[dioxane]— | n-Pentyl |
| 7) | n-Propyl | ⌬—⌬—n-Propyl | n-Propyl—⌬ | Methoxy |
| 8) | Methoxy   n-Propyl (C 47 I, Δε-6.93, Δn-0.126) | | n-Propyl | Methoxy |
| 9) | Ethyl | ⌬(F)—n-Propyl | n-Pentyl—[dioxane]— | Methyl |
| 10) | n-Heptyl | ⌬—n-Butyl | n-Butyl—⌬ | n-Heptyl |
| | (C 81 SmB 208 I, Δε = 0.53, Δn = 0.008) | | | |
| 11) | n-Pentyl | ⌬—n-Pentyl | n-Propyl | Methoxy |
| | (Tg = 41 C 47 N 52 I, Δε = −2.51, Δn = −0.027) | | | |
| 12) | n-Propyl | ⌬—n-Propyl | n-Propyl—⌬ | n-Propyl |
| | (C 151 SmB 168 I)) | | | |

-continued

| | R | $(Z^1-A^1)_n-R^1$ | $R^2-(A^2-Z^2)_r$ | $R^3$ |
|---|---|---|---|---|
| 13) | n-Heptyl | —⬡—n-Butyl | n-Pentyl—⬡— | Methoxy |
| | (C 90 N 129 I, Δε = −1.27, Δn = 0.001) | | | |
| 14) | n-Heptyl | —⬡—n-Butyl | n-Propyl—⬡— | Methoxy |
| 15) | n-Heptyl | —⬡—n-Butyl | n-Pentyl—⬡— | Ethoxy |
| | (C 68 SmB 135 N 144 I, Δε = −1.21, Δn = 0.010) | | | |
| 16) | n-Heptyl | —⬡—n-Butyl | n-Propyl—⬡— | Ethoxy |
| | (C 78 SmB 134 N 145 I, Δε = −1.27, Δn = 0.004) | | | |
| 17) | n-Propyl | —⬡—n-Propyl | n-Pentyl—⬡— | Methoxy |
| | (C 105 N 125 I, Δε = −1.56, Δn = −0.005) | | | |
| 18) | n-Propyl | —⬡—n-Propyl | n-Pentyl—⬡— | Ethoxy |
| | (C 99 SmB 117 N 142 I, Δε = −0.86, Δn = 0) | | | |
| 19) | Ethoxy | —⬡—n-Propyl | n-Propyl—⬡— | Ethoxy |
| | (143 N (117) I, Δε = −1.07, Δn = 0.002) | | | |
| 20) | n-Heptyl | —⬡—n-Butyl | n-Propyl—⬡— | n-Pentyl |
| | (100 Sm (63) N 128 I, Δε = −1.31, Δn = 0.003) | | | |
| 21) | Methoxy | —⬡—n-Propyl | n-Pentyl—⬡— | n-Pentyl |
| | (C 104 SmB (103) N 130 I) | | | |

-continued
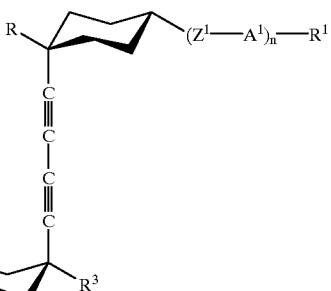
| | R | $(Z^1-A^1)_n-R^1$ | | $R^2-(A^2-Z^2)_r$ | $R^3$ |
|---|---|---|---|---|---|
| 22) | n-Propyl | 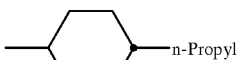 n-Propyl | n-Propyl | 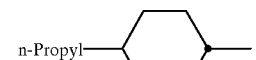 | Ethoxy |
| | | (C 149 N (143) I, Δε = −0.91, Δn = −0.004) | | | |
| 23) | Methoxy | 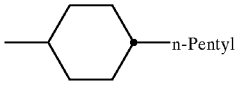 n-Pentyl | n-Pentyl | 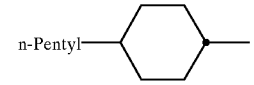 | Methoxy |
| | | (C 117 N (87) I) | | | |
| 24) | Ethoxy | 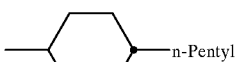 n-Pentyl | n-Pentyl | 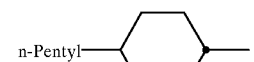 | Ethoxy |
| | | (C 126 N (120) I) | | | |
| 24a) | n-Pentyl | n-Propyl | | n-Propyl | Methoxy |
| 24b) | n-Pentyl | n-Propy | | n-Propyl | n-Pentyl |
EXAMPLES 25–31
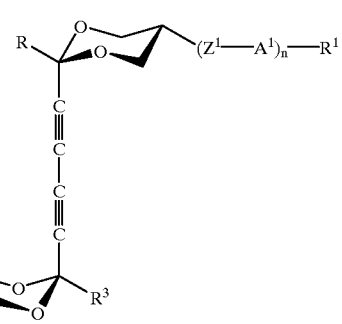
| | R | $(Z^1-A^1)_n-R^1$ | | $R^2-(A^2-Z^2)_r$ | $R^3$ |
|---|---|---|---|---|---|
| 25) | n-Propyl | 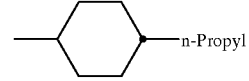 n-Propyl | n-Propyloxy | 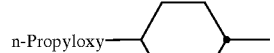 | n-Pentyl |
| 26) | n-Pentyl | 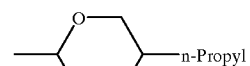 n-Propyl | n-Pentyl | 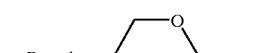 | n-Pentyl |

-continued
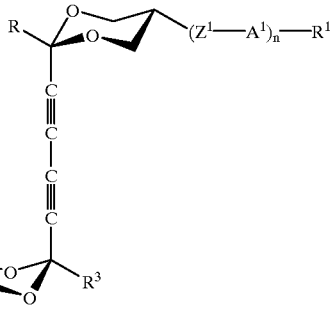
| | R | $(Z^1-A^1)_n-R^1$ | $R^2-(A^2-Z^2)_r$ | $R^3$ |
|---|---|---|---|---|
| 27) | n-Pentyloxy | 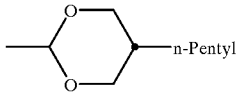 n-Pentyl | n-Pentyl 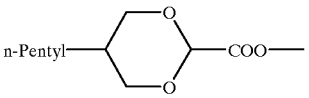 COO— | n-Propyloxy |
| 28) | —CH=CH$_2$ | —OOC 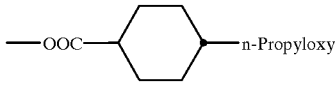 n-Propyloxy | n-Propyl  COO— | —CH=CH$_2$ |
| 29) | n-Propyl | 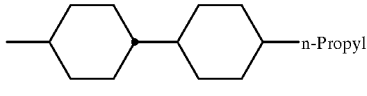 n-Propyl | n-Propyl 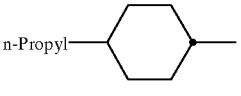 | n-Pentyloxy |
| 30) | Methyl | 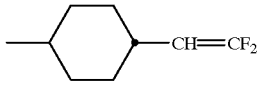 CH=CF$_2$ | n-Pentyl 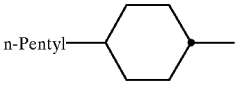 | Ethyl |
| 31) | Ethyl | 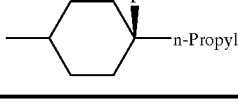 n-Propyl | n-Pentyl 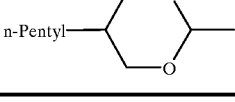 | Methyl |
EXAMPLES 32–39
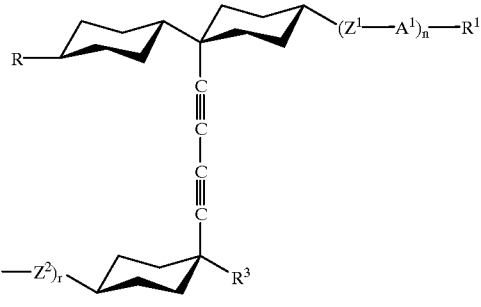
| | R | $(Z^1-A^1)_n-R^1$ | $R^2-(A^2-Z^2)_r$ | $R^3$ |
|---|---|---|---|---|
| 32) | n-Propyl | 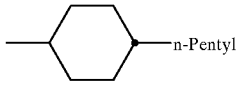 n-Pentyl | n-Pentyl 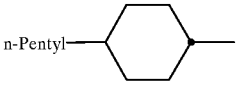 | n-Propyl |

-continued
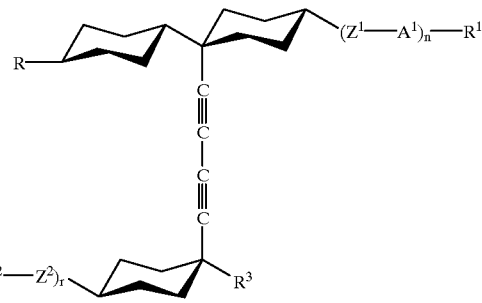
| R | $(Z^1-A^1)_n-R^1$ | $R^2-(A^2-Z^2)_r$ | $R^3$ |
|---|---|---|---|
| 33) n-Propyl | 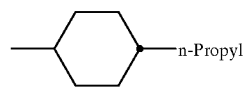 | 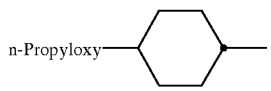 | n-Pentyl |
| 34) n-Pentyl | 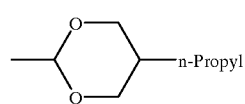 | 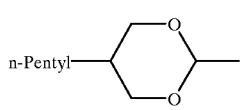 | n-Pentyl |
| 35) n-Butyloxy | 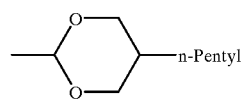 | 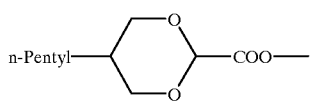 | n-Propyloxy |
| 36) n-Propyl | 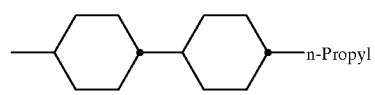 | 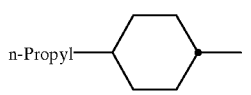 | n-Pentyloxy |
| 37) Ethyl | 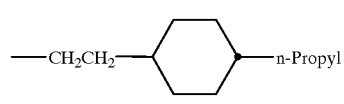 | 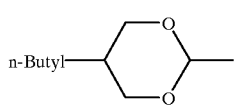 | $OCH_2CH=CH_2$ |
| 38) n-Propyl | — | 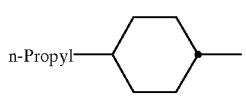 | n-Propyl |
| 39) Ethyl | 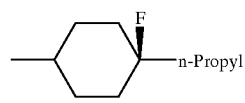 | 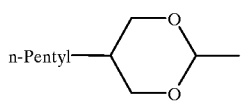 | Methyl |

EXAMPLES 40–45

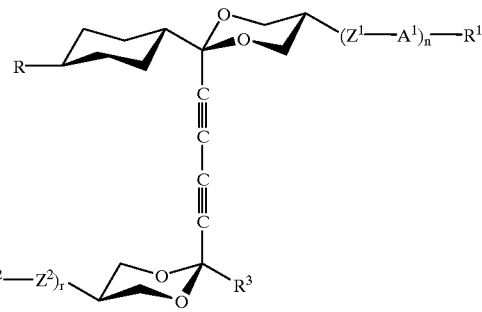

| | R | $(Z^1-A^1)_n-R^1$ | $R^2-(A^2-Z^2)_r$ | $R^3$ |
|---|---|---|---|---|
| 40) | n-Pentyl | [1,3-dioxan-2-yl]-n-Propyl | n-Pentyl-[1,3-dioxan-2-yl] | n-Pentyl |
| 41) | n-Propyloxy | -CH$_2$CH$_2$-[cyclohexyl]-n-Propyl | n-Propyl-[cyclohexyl]-CH$_2$CH$_2$- | n-Propyl |
| 42) | n-Butyloxy | [1,3-dioxan-2-yl]-n-Pentyl | n-Pentyl-[1,3-dioxan-2-yl]-COO- | n-Propyloxy |
| 43) | n-O-Propyl | -CH$_2$CH$_2$-[cyclohexyl]-n-Propyl | n-Propyl-[cyclohexyl]-CH$_2$CH$_2$- | n-O-Propyl |
| 44) | Ethyl | -CH$_2$CH$_2$-[cyclohexyl]-n-Propyl | n-Butyl-[1,3-dioxan-2-yl] | OCH$_2$CH=CH$_2$ |
| 45) | Ethyl | -[F-cyclohexyl]-n-Propyl | n-Pentyl-[1,3-dioxan-2-yl] | Methyl |

EXAMPLES 46–50
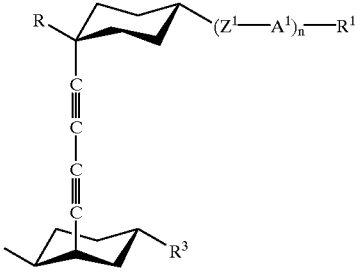
| R | $(Z^1-A^1)_n-R^1$ | $R^2-(A^2-Z^2)_r$ | $R^3$ |
|---|---|---|---|
| 46) n-Propyl |  —n-Pentyl | n-Pentyl—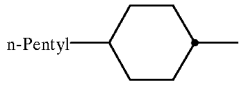 | n-Propyl |
| 47) n-Propyl | 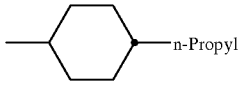 —n-Propyl | n-Propyloxy—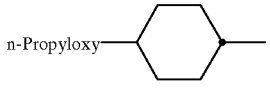 | n-Pentyl |
| 48) n-O-Propyl | —CH$_2$CH$_2$—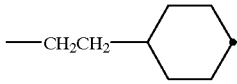—n-Propyl | n-Propyl—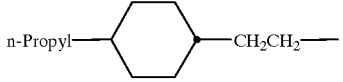—CH$_2$CH$_2$— | n-Propyl |
| 49) —CH=CF$_2$ | 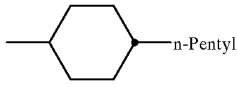—n-Pentyl | n-Pentyloxy——CH$_2$CH$_2$— | —CH=CF$_2$ |
| 50) Methyl | 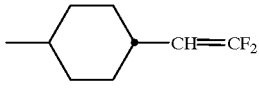—CH=CF$_2$ | n-Pentyl—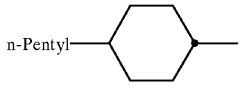 | Ethyl |
EXAMPLES 51–53
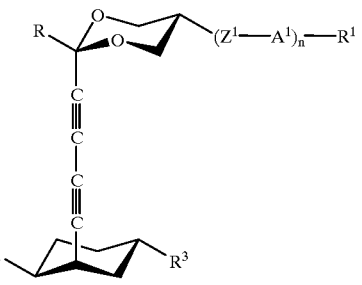
| R | $(Z^1-A^1)_n-R^1$ | $R^2-(A^2-Z^2)_r$ | $R^3$ |
|---|---|---|---|
| 51) n-Propyl | 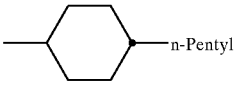—n-Pentyl | n-Pentyl—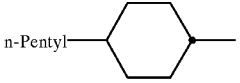 | n-Propyl |

-continued
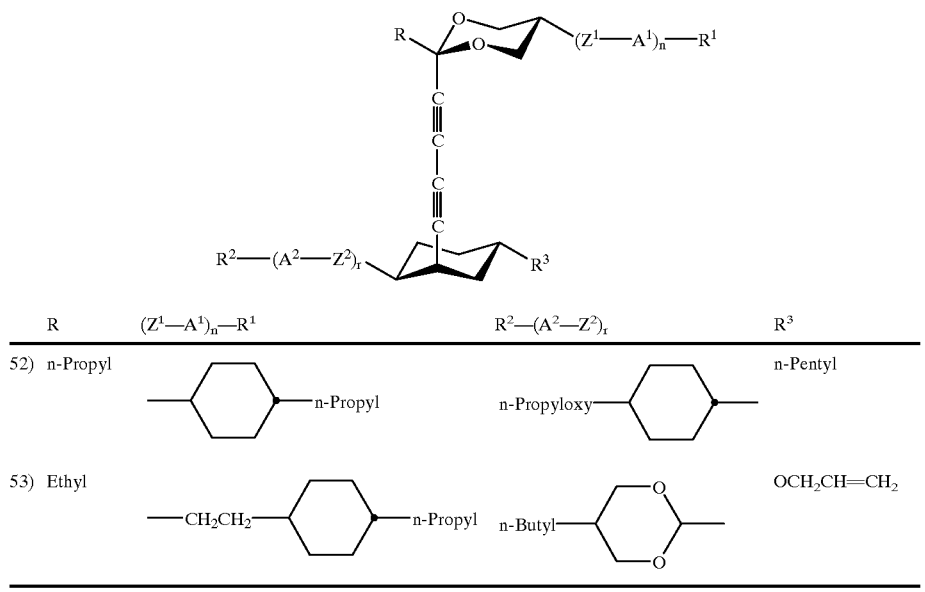
| | R | $(Z^1-A^1)_n-R^1$ | $R^2-(A^2-Z^2)_r$ | $R^3$ |
|---|---|---|---|---|
| 52) | n-Propyl | —⬡—n-Propyl | n-Propyloxy—⬡— | n-Pentyl |
| 53) | Ethyl | —CH₂CH₂—⬡—n-Propyl | n-Butyl—[dioxane]— | $OCH_2CH=CH_2$ |
EXAMPLES 54–56
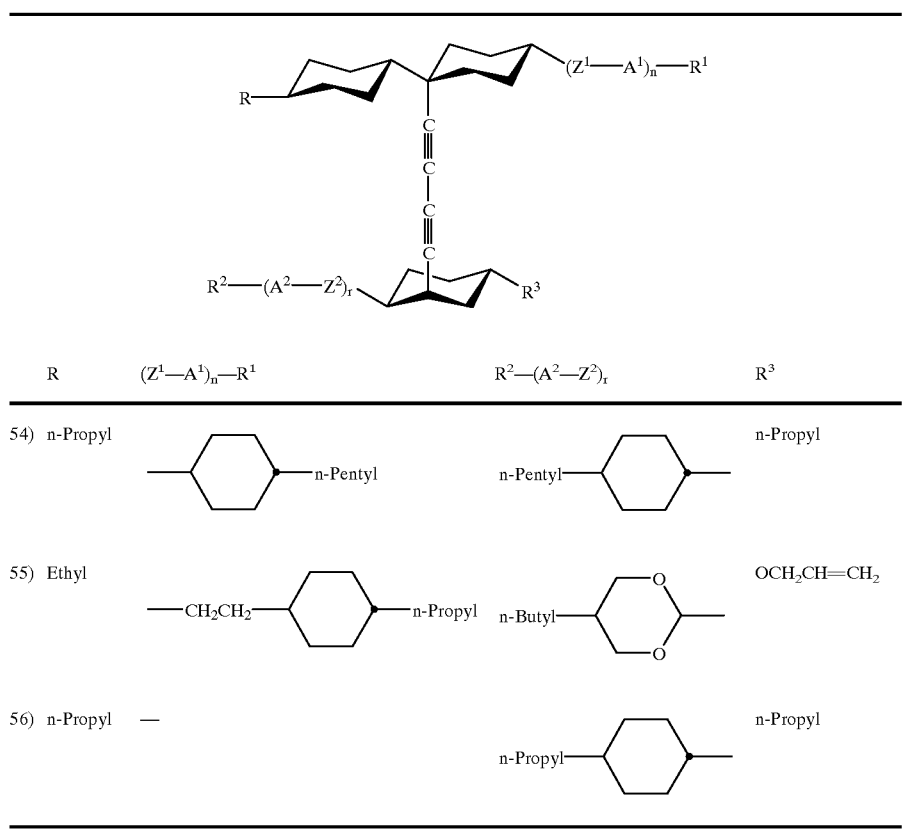
| | R | $(Z^1-A^1)_n-R^1$ | $R^2-(A^2-Z^2)_r$ | $R^3$ |
|---|---|---|---|---|
| 54) | n-Propyl | —⬡—n-Pentyl | n-Pentyl—⬡— | n-Propyl |
| 55) | Ethyl | —CH₂CH₂—⬡—n-Propyl | n-Butyl—[dioxane]— | $OCH_2CH=CH_2$ |
| 56) | n-Propyl | — | n-Propyl—⬡— | n-Propyl |

EXAMPLES 57–62
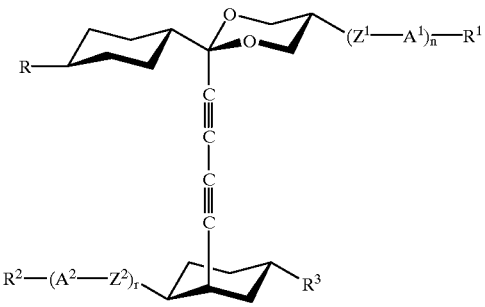
| R | $(Z^1-A^1)_n-R^1$ | $R^2-(A^2-Z^2)_r$ | $R^3$ |
|---|---|---|---|
| 57) n-Propyl | —⬡—n-Pentyl | n-Pentyl—⬡— | n-Propyl |
| 58) n-Propyl | —⬡—n-Propyl | n-Propyloxy—⬡— | n-Pentyl |
| 59) n-Pentyl | —[dioxane]—n-Propyl | n-Pentyl—[dioxane]— | n-Pentyl |
| 60) —CH=CH$_2$ | —OOC—⬡—n-Propyloxy | n-Propyl—⬡—COO— | —CH=CH$_2$ |
| 61) —CH$_2$CH=CH$_2$ | —⬡—n-Propyl | n-Pentyl—[dioxane]— | n-Pentyl |
| 62) Ethyl | —⬡(F)—n-Propyl | n-Pentyl—[dioxane]— | Methyl |

EXAMPLES 62–67

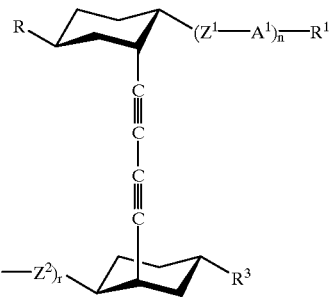

| R | $(Z^1-A^1)_n-R^1$ | $R^2-(A^2-Z^2)_r$ | $R^3$ |
|---|---|---|---|
| 62) n-Propyl | —⟨cyclohexyl⟩—n-Propyl | n-Propyloxy—⟨cyclohexyl⟩— | n-Pentyl |
| 63) n-Butyloxy | —⟨1,3-dioxane⟩—n-Pentyl | n-Pentyl—⟨1,3-dioxane⟩—COO— | n-Propyloxy |
| 64) —CH$_2$CH=CH$_2$ | —⟨cyclohexyl⟩—n-Propyl | n-Pentyl—⟨1,3-dioxane⟩— | n-Pentyl |
| 65) n-Propyl | —⟨cyclohexyl⟩—⟨cyclohexyl⟩—n-Propyl | n-Propyl—⟨cyclohexyl⟩— | n-Pentyloxy |
| 66) n-Propyl | — | n-Propyl—⟨cyclohexyl⟩— | n-Propyl |
| 67) Ethyl | —⟨cyclohexyl-F⟩—n-Propyl | n-Pentyl—⟨1,3-dioxane⟩— | Methyl |

EXAMPLES 68–72
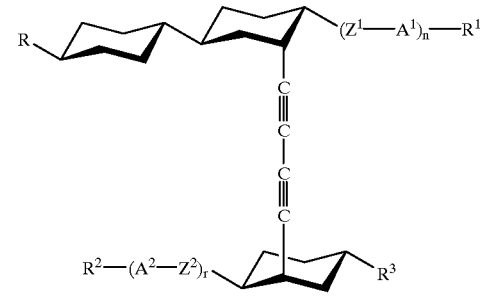
| R | $(Z^1-A^1)_n-R^1$ | $R^2-(A^2-Z^2)_r$ | $R^3$ |
|---|---|---|---|
| 68) n-Propyl | —⬡—n-Pentyl | n-Pentyl—⬡— | n-Propyl |
| 69) n-Propyl | —⬡—n-Propyl | n-Propyloxy—⬡— | n-Pentyl |
| 70) n-Pentyl | —[dioxane]—n-Propyl | n-Pentyl—[dioxane]— | n-Pentyl |
| 71) —CH₂CH=CH₂ | —⬡—n-Propyl | n-Pentyl—[dioxane]— | n-Pentyl |
| 72) Ethyl | —CH₂CH₂—⬡—n-Propyl | n-Butyl—[dioxane]— | OCH₂CH=CH₂ |
EXAMPLES 73–81
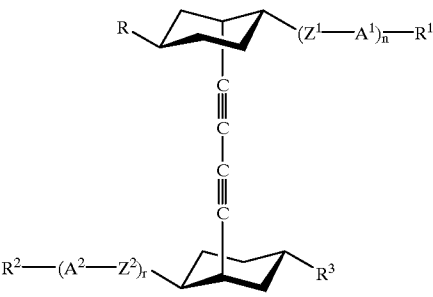
| R | $(Z^1-A^1)_n-R^1$ | $R^2-(A^2-Z^2)_r$ | $R^3$ |
|---|---|---|---|
| 73) n-Propyl | —⬡—n-Pentyl | n-Pentyl—⬡— | n-Propyl |

-continued
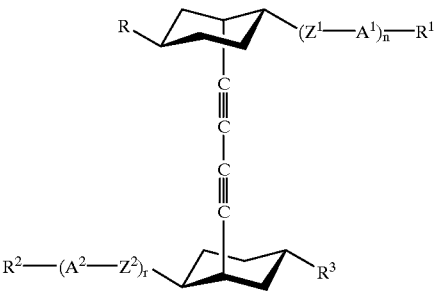
| R | $(Z^1-A^1)_n-R^1$ | $R^2-(A^2-Z^2)_r$ | $R^3$ |
| --- | --- | --- | --- |
| 74) n-Propyl | 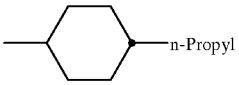 | 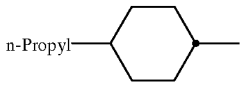 | n-Pentyl |
| 75) n-Pentyl |  |  | n-Pentyl |
| 76) n-Propyloxy | 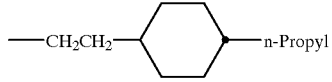 |  | n-Propyl |
| 77) —CH=CF$_2$ | 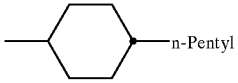 |  | —CH=CF$_2$ |
| 78) —CH$_2$CH=CH$_2$ | 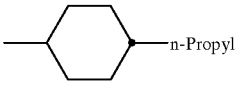 | 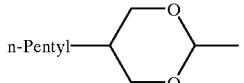 | n-Pentyl |
| 79) n-Propyl | 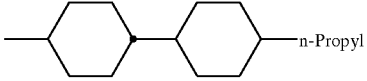 | 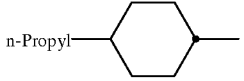 | n-Pentyloxy |
| 80) Methyl | 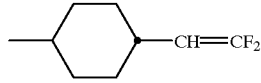 | 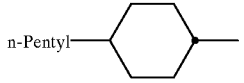 | Ethyl |
| 81) Ethyl | 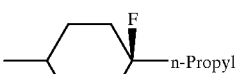 | 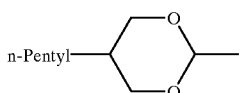 | Methyl |

EXAMPLES 81–85

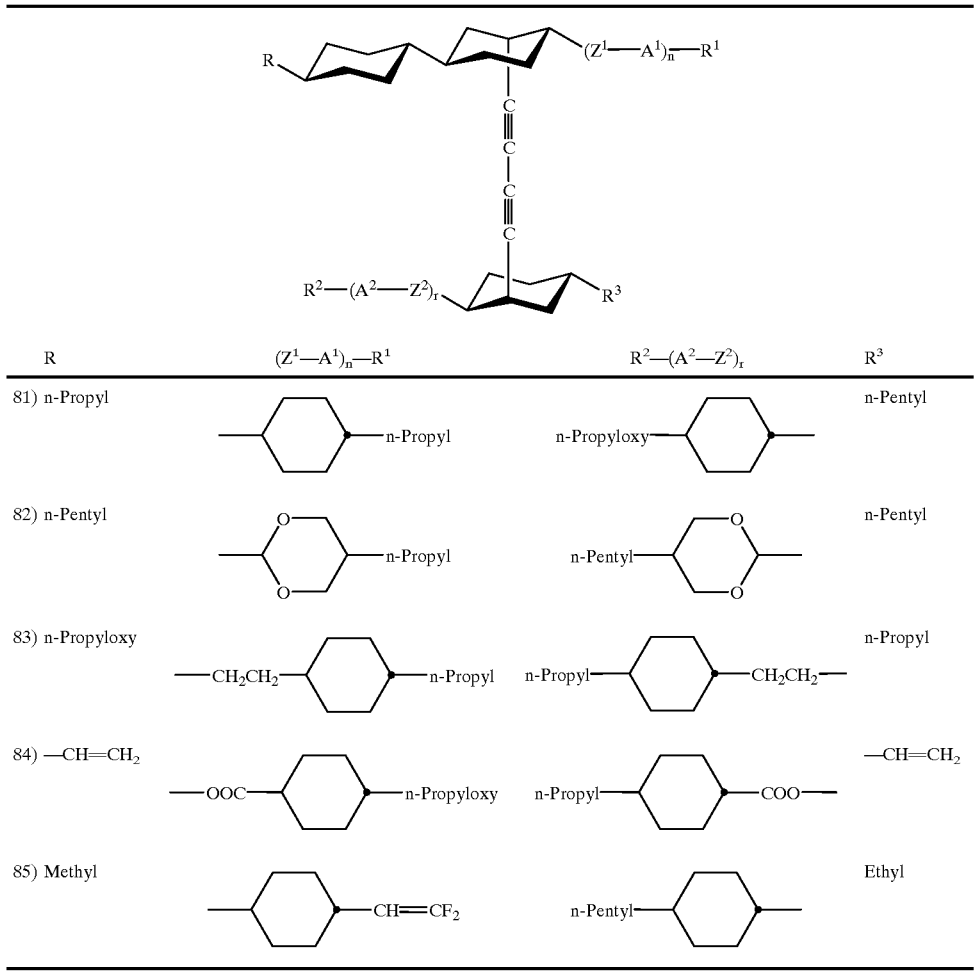

EXAMPLE 86

4-[4-(4,4'-Dipentylbicyclohexyl-4-ylethynyl)-2-fluorophenylethynyl]-4,4'-dipentylbicyclohexyl 0.908 g of 4-(4-bromo-2-fluorophenylethynyl)-4,4'-dipentylbicyclohexyl (obtainable by Wittig reaction of 4,4'-dipentylbicyclohexyl-4-carbaldehyde with 4-bromo-2-fluorobenzyltriphenylphosphonium bromide, addition of bromine onto the resultant alkene and subsequent dehydrobromination using a base), 0.715 g of 4-ethynyl-4,4'-dipentylbicyclohexyl and 0.104 g of tetrakis-(triphenylphosphine)palladium(0) are stirred overnight at 80° C. in 5 ml of pyrrolidine. Conventional work-up gives 4-[4-(4,4'-dipentylbicyclohexyl-4-ylethynyl)-2-fluorophenylethynyl]-4,4'-dipentylbicyclohexyl (C 177 I).

EXAMPLE 87

4-[4-(4,4'-Dipentylbicyclohexyl-4-ylethynyl)-3-fluorophenylethynyl]-4-methoxy-4'-propylbicyclohexyl Analogously to Example 4, 1.913 g of 4-(4-bromo-2-fluorophenylethynyl)-4,4'-dipentylbicyclohexyl are reacted with 0.997 g of 4-ethynyl-4-methoxy-4'-propylbicyclohexyl in the presence of 0.219 g of tetrakis(triphenylphosphine) palladium(0) and 5 ml of pyrrolidine, giving 4-[4-(4,4'-dipentylbicyclohexyl-4-ylethynyl)-3-fluorophenylethynyl]-4-methoxy-4'-propyl-bicyclohexyl (C 177 N (36) I, Δε −0.26, Δn −0.015).

The following compounds according to the invention are obtained analogously from the corresponding precursors:

EXAMPLE 88

4-[4-(4,4'-Dipentylbicyclohexyl-4-ylethynyl)fluorophenylethynyl]-4-methoxy-4'-propylbicyclohexyl The title compound is obtained analogously to Example 87 using 4-(4-bromo-3-fluorophenylethynyl)-4,4'-dipentylbicyclohexyl (C 120 N (34) I, Δε=−1.22, Δn=−0.015).

EXAMPLES 89–92
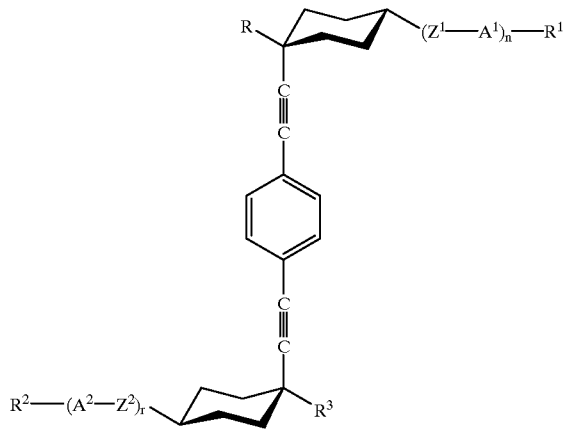
| R | $(Z^1-A^1)_n-R^1$ | $R^2-(A^2-Z^2)_r$ | $R^3$ |
|---|---|---|---|
| 89) Methoxy | 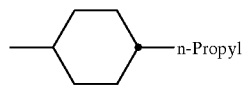 n-Propyl | n-Pentyl 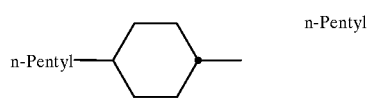 | n-Pentyl |
| (C 121 N (32) I, $\Delta\epsilon = -1.29$, $\Delta n = -0.019$) | | | |
| 90) n-Pentyl | 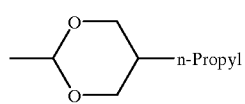 n-Propyl | n-Pentyl 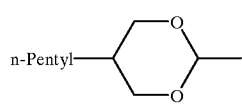 | n-Pentyl |
| 91) n-Propyloxy | —CH$_2$CH$_2$— 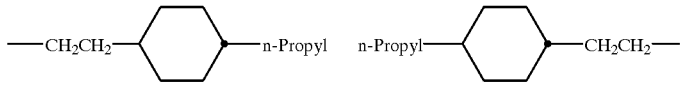 n-Propyl | n-Propyl— ... —CH$_2$CH$_2$— | n-Propyl |
| 92) n-Propyl |  n-Pentyl | n-Pentyl— ... — | n-Propyl |

EXAMPLES 93–94

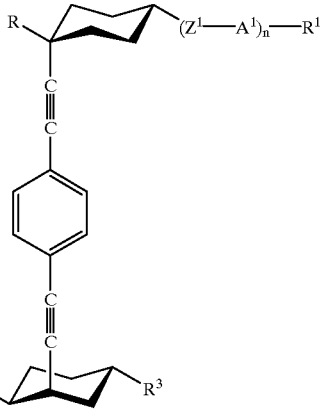

| | R | $(Z^1-A^1)_n-R^1$ | $R^2-(A^2-Z^2)_r$ | $R^3$ |
|---|---|---|---|---|
| 93) | n-Propyl | —⟨cyclohexyl⟩—n-Pentyl | n-Pentyl—⟨cyclohexyl⟩— | n-Propyl |
| 94) | n-Propyl | —⟨cyclohexyl⟩—n-Propyl | n-Propyloxy—⟨cyclohexyl⟩— | n-Pentyl |

EXAMPLE 95

1-(4,4'-Dipentylbicyclohexyl-4-ylethynyl)-4-pentylcyclohexyl 4-propylcyclohexanecarboxylate a) 1-(4,4'-Dipentylbicyclohexyl-4-ylethynyl)-4-pentylcyclohexanol 6.00 g of 4-ethynyl-4,4'-dipentylcyclohexyl are introduced in 50 ml of THF, and 9.66 ml of a 15% solution of butyllithium in hexane are added dropwise at −20° C. After 10 minutes, 2.66 g of 4-pentylcyclohexanone in 10 ml of THF are added dropwise to the reaction mixture. The mixture is allowed to warm to RT, acidified using dilute hydrochloric acid and subjected to conventional work-up, giving 1-(4,4'-dipentylbicyclohexyl-4-ylethynyl)-4-pentylcyclohexanol.

b) 1-(4,4'-Dipentylbicyclohexyl-4-ylethynyl)-4-pentylcyclohexyl 4-propylcyclohexanecarboxylate 1.10 g of 1-(4,4'-dipentylbicyclohexyl-4-ylethynyl)-4-pentylcyclohexanol and 0.394 g of 4-propylcyclohexanecarboxylic acid are dissolved in 4 ml of dichloromethane, and 0.283 g of 4-(dimethylamino)pyridine is added. 5.569 g of N,N-dicyclohexylcarbodiimide dissolved in 3 ml of dichloromethane are then added dropwise to the reaction mixture. The mixture is stirred overnight and subjected to conventional work-up, giving 1-(4,4'-dipentylbicyclohexyl-4-ylethynyl)-4-pentylcyclohexyl 4-propylcyclohexanecarboxylate (C 66 SmB 171 I, Δε −0.02).

The following compounds according to the invention are obtained analogously from the corresponding precursors:

EXAMPLES 96–102

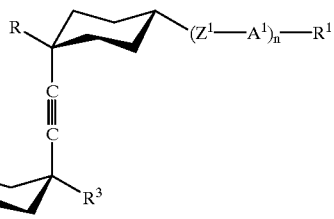

| # | R | (Z¹—A¹)ₙ—R¹ | R²—(A²—Z²)ᵣ | R³ |
|---|---|---|---|---|
| 96) | n-Pentyl-[Cy]-C(=O)-O— | —[Cy]-n-Pentyl | n-Pentyl-[Cy]— | n-Propyl |
| | (C 139 SmB 232 I, $\Delta\epsilon = 0.37$, $\Delta n = 0.057$) | | | |
| 97) | n-Propyl | —[Cy]-n-Propyl | n-Propyloxy-[Cy]— | n-Pentyl |
| 98) | n-Pentyl | —[Dioxane]-n-Propyl | n-Pentyl-[Dioxane]— | n-Pentyl |
| 99) | n-Propyloxy | —CH₂CH₂-[Cy]-n-Propyl | n-Propyl-[Cy]-CH₂CH₂— | n-Propyl |
| 100) | CH=CHF₂ | —[Cy]-n-Pentyl | n-Pentyloxy-[Cy]-CH₂CH₂— | n-Pentyl |
| 101) | n-Pentyloxy | —[Cy]-n-Propyl | n-Pentyl-[Dioxane]— | n-Propyl |
| 102) | Ethyl | —[Cy(F)]-n-Propyl | n-Pentyl-[Dioxane]— | Methyl |

EXAMPLES 103–108
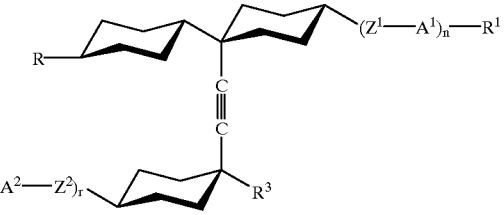
| | R | $(Z^1-A^1)_n-R^1$ | $R^2-(A^2-Z^2)_r$ | $R^3$ |
|---|---|---|---|---|
| 103) | n-Propyl |  -n-Pentyl | n-Pentyl- 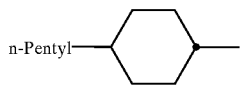 | n-Propyl |
| 104) | n-Pentyl | 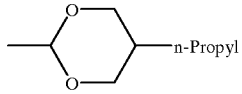 -n-Propyl | n-Pentyl- 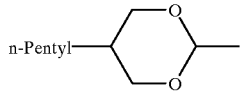 | n-Pentyl |
| 105) | —CH=CF$_2$ | 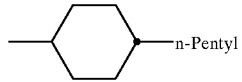 -n-Pentyl | n-Pentyloxy-  -CH$_2$CH$_2$— | —CH=CF$_2$ |
| 106) | —CH=CH$_2$ | —OOC- 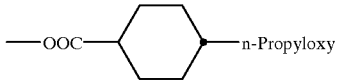 -n-Propyloxy | n-Propyl- 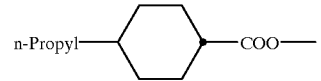 -COO— | —CH=CH$_2$ |
| 107) | Ethyl | —CH$_2$CH$_2$- 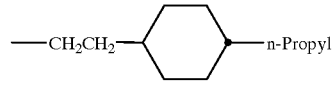 -n-Propyl | n-Butyl- 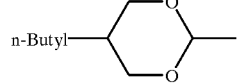 | OCH$_2$CH=CH$_2$ |
| 108) | Methyl | 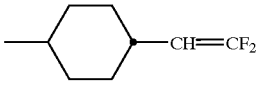 -CH=CF$_2$ | n-Pentyl- 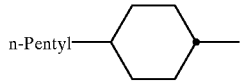 | Ethyl |
EXAMPLES 109–114
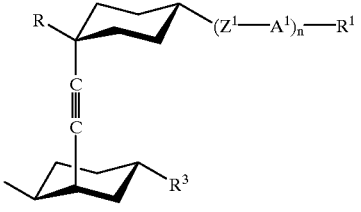
| | R | $(Z^1-A^1)_n-R^1$ | $R^2-(A^2-Z^2)_r$ | $R^3$ |
|---|---|---|---|---|
| 109) | n-Propyl | 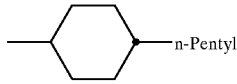 -n-Pentyl | n-Pentyl- 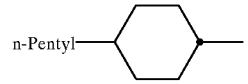 | n-Propyl |

-continued

| R | $(Z^1-A^1)_n-R^1$ | $R^2-(A^2-Z^2)_r$ | $R^3$ |
|---|---|---|---|
| 110) n-Propyl | —⟨cyclohexyl⟩—n-Propyl | n-Propyl—⟨cyclohexyl⟩— | n-Pentyl |
| 111) n-Pentyl | —⟨1,3-dioxane⟩—n-Propyl | n-Pentyl—⟨1,3-dioxane⟩— | n-Pentyl |
| 112) n-Propyl | —⟨cyclohexyl⟩—⟨cyclohexyl⟩—n-Propyl | n-Propyl—⟨cyclohexyl⟩— | n-Pentyloxy |
| 113) Methyl | —⟨cyclohexyl⟩—CH=CF$_2$ | n-Pentyl—⟨cyclohexyl⟩— | Ethyl |
| 114) Ethyl | —⟨cyclohexyl(F)⟩—n-Propyl | n-Pentyl—⟨1,3-dioxane⟩— | Methyl |

EXAMPLES 115–118

| R | $(Z^1-A^1)_n-R^1$ | $R^2-(A^2-Z^2)_r$ | $R^3$ |
|---|---|---|---|
| 115) n-Propyl | —⟨cyclohexyl⟩—n-Pentyl | n-Pentyl—⟨cyclohexyl⟩— | n-Propyl |
| 116) n-Pentyl | —⟨1,3-dioxane⟩—n-Propyl | n-Pentyl—⟨1,3-dioxane⟩— | n-Pentyl |
| 117) n-Propyloxy | —CH$_2$CH$_2$—⟨cyclohexyl⟩—n-Propyl | n-Propyl—⟨cyclohexyl⟩—CH$_2$CH$_2$— | n-Propyl |

-continued

| R | $(Z^1-A^1)_n-R^1$ | $R^2-(A^2-Z^2)_r$ | $R^3$ |
|---|---|---|---|
| 118) Ethyl | cyclohexyl(F)(n-Propyl) | n-Pentyl-dioxane | Methyl |

EXAMPLES 119–125

| R | $(Z^1-A^1)_n-R^1$ | $R^2-(A^2-Z^2)_r$ | $R^3$ |
|---|---|---|---|
| 119) n-Propyl | cyclohexyl-n-Pentyl | n-Pentyl-cyclohexyl | n-Propyl |
| 120) n-Propyl | cyclohexyl-n-Propyl | n-Propyloxy-cyclohexyl | n-Pentyl |
| 121) —CH=CF$_2$ | cyclohexyl-n-Pentyl | n-Pentyloxy-cyclohexyl-CH$_2$CH$_2$— | —CH=CF$_2$ |
| 122) n-O-Pentyl | dioxane-n-Pentyl | n-Pentyl-dioxane-COO— | n-Propyl |
| 123) —CH=CH$_2$ | —OOC-cyclohexyl-n-Propyloxy | n-Propyl-cyclohexyl-COO— | —CH=CH$_2$ |
| 124) n-Propyl | bicyclohexyl-n-Propyl | n-Propyl-cyclohexyl | n-Pentyloxy |

-continued

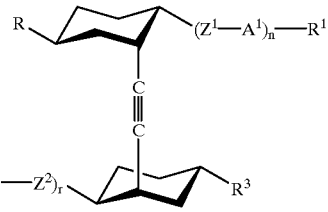

| R | $(Z^1-A^1)_n-R^1$ | $R^2-(A^2-Z^2)_r$ | $R^3$ |
|---|---|---|---|
| 125) Methyl | —⬡—CH=CF$_2$ | n-Pentyl—⬡— | Ethyl |

EXAMPLES 126–131

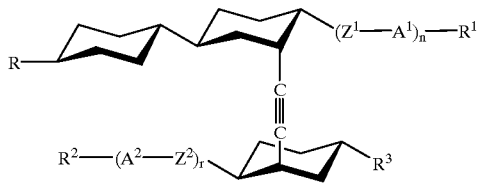

| R | $(Z^1-A^1)_n-R^1$ | $R^2-(A^2-Z^2)_r$ | $R^3$ |
|---|---|---|---|
| 126) n-Propyl | —⬡—n-Pentyl | n-Pentyl—⬡— | n-Propyl |
| 127) n-Propyl | —⬡—n-Propyl | n-Propyloxy—⬡— | n-Pentyl |
| 128) n-Pentyl | —⟨dioxane⟩—n-Propyl | n-Pentyl—⟨dioxane⟩— | n-Pentyl |
| 129) —CH$_2$CH=CH$_2$ | —⬡—n-Propyl | n-Pentyl—⟨dioxane⟩— | n-Pentyl |
| 130) n-Propyl | —⬡—⬡—n-Propyl | n-Propyl—⬡— | n-Pentyloxy |
| 131) Ethyl | —⬡(F)—n-Propyl | n-Pentyl—⟨dioxane⟩— | Methyl |

EXAMPLES 132–135

![Structure: cyclohexane-C≡C-cyclohexane with R, (Z¹—A¹)ₙ—R¹, R²—(A²—Z²)ᵣ, R³ substituents]

| | R | $(Z^1-A^1)_n-R^1$ | $R^2-(A^2-Z^2)_r$ | $R^3$ |
|---|---|---|---|---|
| 132) | n-Propyl | —⟨cyclohexane⟩—n-Pentyl | n-Pentyl—⟨cyclohexane⟩— | n-Propyl |
| 133) | n-Propyl | —⟨cyclohexane⟩—n-Propyl | n-Propyloxy—⟨cyclohexane⟩— | n-Pentyl |
| 134) | Ethyl | —CH₂CH₂—⟨cyclohexane⟩—n-Propyl | n-Butyl—⟨1,3-dioxane⟩— | OCH₂CH=CH₂ |
| 135) | n-Propyl | — | n-Propyl—⟨cyclohexane⟩— | n-Propyl |

EXAMPLES 136–140

![Structure: bicyclohexyl-C≡C-cyclohexane with R, (Z¹—A¹)ₙ—R¹, R²—(A²—Z²)ᵣ, R³ substituents]

| | R | $(Z^1-A^1)_n-R^1$ | $R^2-(A^2-Z^2)_r$ | $R^3$ |
|---|---|---|---|---|
| 136) | n-Propyl | —⟨cyclohexane⟩—n-Pentyl | n-Pentyl—⟨cyclohexane⟩— | n-Propyl |
| 137) | n-Propyl | —⟨cyclohexane⟩—n-Propyl | n-Propyloxy—⟨cyclohexane⟩— | n-Pentyl |
| 138) | n-Pentyl | —⟨1,3-dioxane⟩—n-Propyl | n-Pentyl—⟨1,3-dioxane⟩— | n-Pentyl |
| 139) | n-Pentyloxy | —⟨1,3-dioxane⟩—n-Pentyl | n-Pentyl—⟨1,3-dioxane⟩—COO— | n-Propyloxy |

-continued

| R | $(Z^1-A^1)_n-R^1$ | $R^2-(A^2-Z^2)_r$ | $R^3$ |
|---|---|---|---|
| 140) Methyl | —⟨cyclohexyl⟩—CH=CF$_2$ | n-Pentyl—⟨cyclohexyl⟩— | Ethyl |

EXAMPLES 141–146

| R | $(Z^1-A^1)_n-R^1$ | $R^2-(A^2-Z^2)_r$ | $R^3$ |
|---|---|---|---|
| 141) n-Propyl | —⟨cyclohexyl⟩—n-Pentyl | n-Pentyl—⟨cyclohexyl⟩— | n-Propyl |
| 142) n-Pentyl | —⟨dioxanyl⟩—n-Propyl | n-Pentyl—⟨dioxanyl⟩— | n-Pentyl |
| 143) —CH=CF$_2$ | —⟨cyclohexyl⟩—n-Pentyl | n-Pentyloxy—⟨cyclohexyl⟩—CH$_2$CH$_2$— | —CH=CF$_2$ |
| 144) —CH=CH$_2$ | —OOC—⟨cyclohexyl⟩—n-Propyloxy | n-Propyloxy—⟨cyclohexyl⟩—COO— | —CH=CH$_2$ |
| 145) Ethyl | —CH$_2$CH$_2$—⟨cyclohexyl⟩—n-Propyl | n-Butyl—⟨dioxanyl⟩— | OCH$_2$CH=CH$_2$ |
| 146) n-Propyl | — | n-Propyl—⟨cyclohexyl⟩— | n-Propyl |

EXAMPLES 147–152
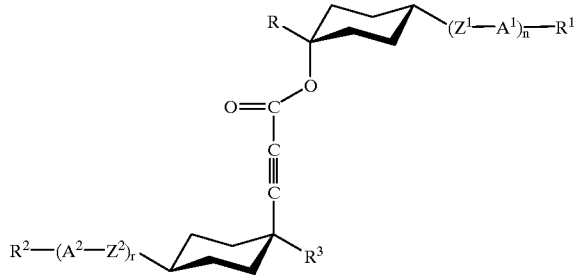
| | R | $(Z^1-A^1)_n-R^1$ | $R^2-(A^2-Z^2)_r$ | $R^3$ |
|---|---|---|---|---|
| 147) | n-Propyl | 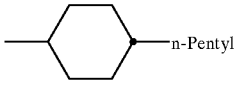—n-Pentyl | n-Pentyl—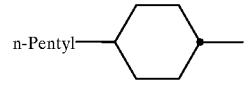 | n-Propyl |
| 148) | n-Propyl | 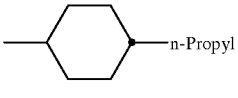—n-Propyl | n-Propyloxy—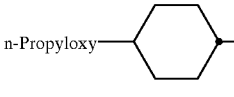 | n-Pentyl |
| 149) | n-Pentyl | 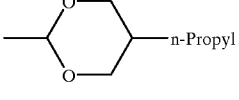—n-Propyl | n-Pentyl—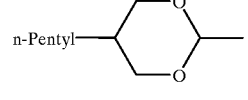 | n-Pentyl |
| 150) | n-Propylene | —CH$_2$CH$_2$—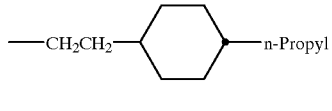—n-Propyl | n-Propyl—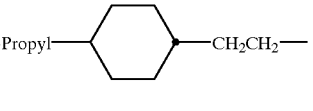—CH$_2$CH$_2$— | n-Propyl |
| 151) | n-Pentyloxy | 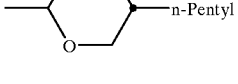—n-Pentyl | n-Pentyl—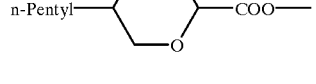—COO— | n-Propyloxy |
| 152) | —CH$_2$CH=CH$_2$ | —n-Propyl | n-Pentyl—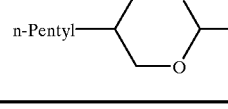 | n-Pentyl |

EXAMPLES 153–157
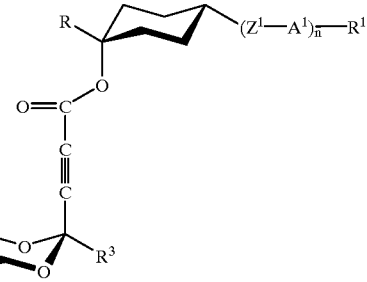
| R | $(Z^1-A^1)_n-R^1$ | $R^2-(A^2-Z^2)_r$ | $R^3$ |
|---|---|---|---|
| 153) n-Propyl | 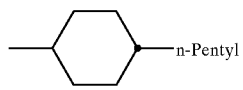 —n-Pentyl | n-Pentyl—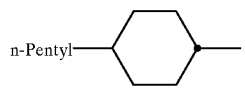 | n-Propyl |
| 154) n-Propyloxy | —CH$_2$CH$_2$—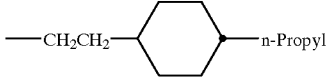—n-Propyl | n-Propyl—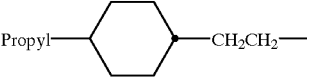—CH$_2$CH$_2$— | n-Propyl |
| 155) —CH=CH$_2$ | —OOC—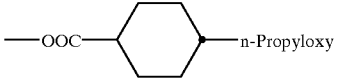—n-Propyloxy | n-Propyl—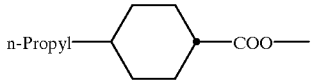—COO— | —CH=CH$_2$ |
| 156) CH$_2$CH=CH$_2$ | —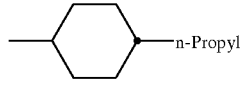—n-Propyl | n-Pentyl—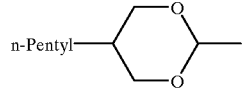 | n-Pentyl |
| 157) n-Propyl | — | n-Propyl—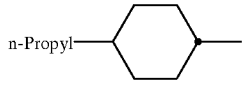 | n-Propyl |
EXAMPLES 157–164
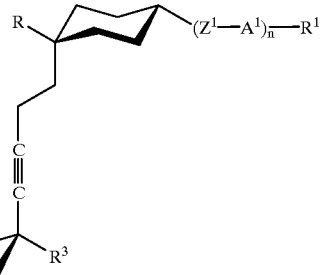
| R | $(Z^1-A^1)_n-R^1$ | $R^2-(A^2-Z^2)_r$ | $R^3$ |
|---|---|---|---|
| 157) n-Propyl | —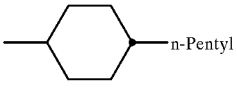—n-Pentyl | n-Pentyl—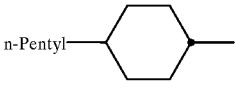 | n-Propyl |

-continued
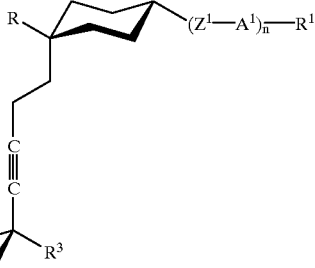
| R | $(Z^1-A^1)_n-R^1$ | $R^2-(A^2-Z^2)_r$ | $R^3$ |
|---|---|---|---|
| 158) n-Propyl | 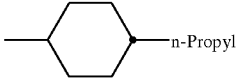 | 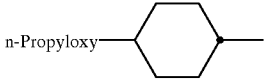 | n-Pentyl |
| 159) n-Pentyl | 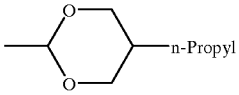 | 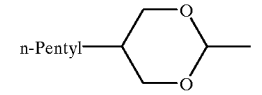 | n-Pentyl |
| 160) n-Propyloxy | 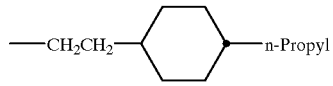 | 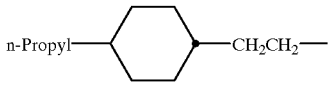 | n-Propyl |
| 161) n-Pentyloxy | 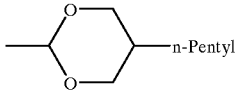 | 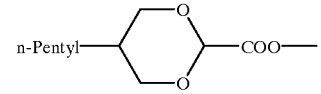 | n-Propyloxy |
| 162) —CH$_2$CH=CH$_2$ | 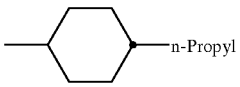 | 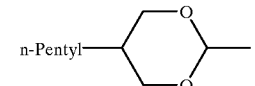 | n-Pentyl |
| 163) Ethyl | 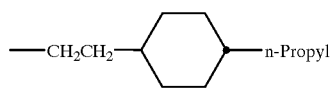 | 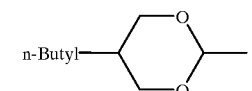 | OCH$_2$CH=CH$_2$ |
| 164) Ethyl |  | 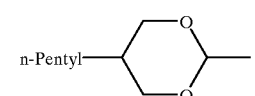 | Methyl |

EXAMPLES 165–168
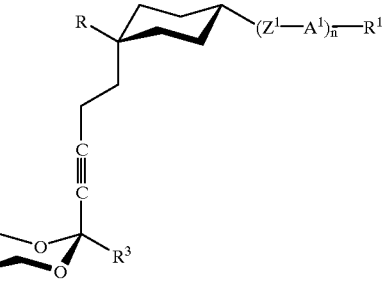
| | R | $(Z^1-A^1)_n-R^1$ | $R^2-(A^2-Z^2)_r$ | $R^3$ |
|---|---|---|---|---|
| 165) | n-Propyl | 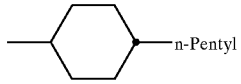—n-Pentyl | n-Pentyl— | n-Propyl |
| 166) | n-Pentyl | 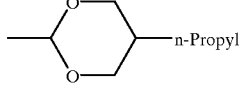—n-Propyl | n-Pentyl—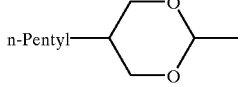 | n-Pentyl |
| 167) | —CH=CH$_2$ | —OOC—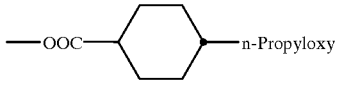—n-Propyloxy | n-Propyl—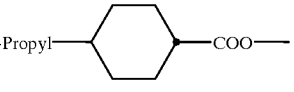—COO— | —CH=CH$_2$ |
| 168) | Ethyl | —CH$_2$CH$_2$—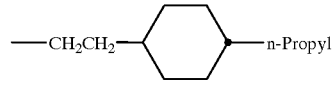—n-Propyl | n-Butyl—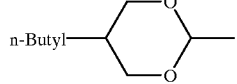 | OCH$_2$CH=CH$_2$ |
EXAMPLES 169–173
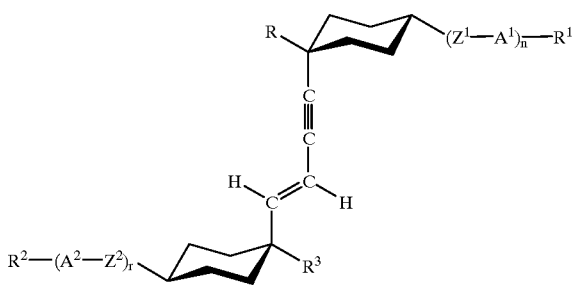
| | R | $(Z^1-A^1)_n-R^1$ | $R^2-(A^2-Z^2)_r$ | $R^3$ |
|---|---|---|---|---|
| 169) | n-Propyl | 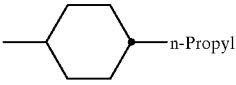—n-Propyl | n-Propyloxy—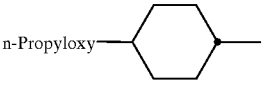 | n-Pentyl |
| 170) | n-Propyloxy | —CH$_2$CH$_2$—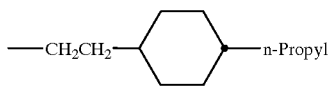—n-Propyl | n-Propyl—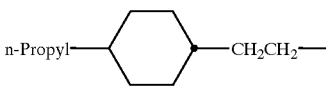—CH$_2$CH$_2$— | n-Propyl |

-continued
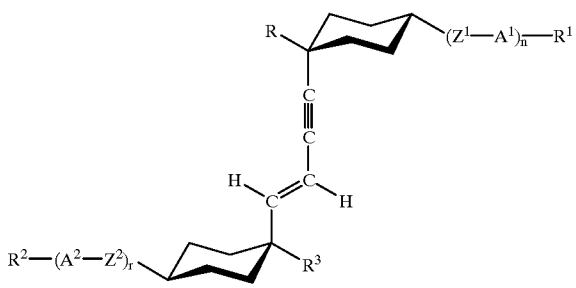
| | R | (Z¹—A¹)ₙ—R¹ | R²—(A²—Z²)ᵣ | R³ |
|---|---|---|---|---|
| 171) | —CH₂CH=CH₂ | 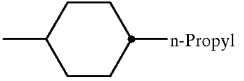—n-Propyl | n-Pentyl—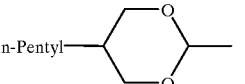 | n-Pentyl |
| 172) | n-Propyl | 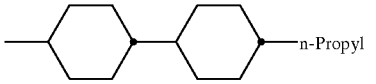—n-Propyl | n-Propyl—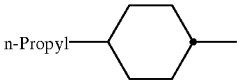 | n-Pentyloxy |
| 173) | Ethyl | —CH₂CH₂—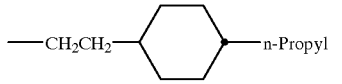—n-Propyl | n-Butyl—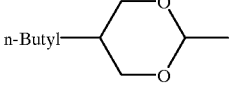 | OCH₂CH=CH₂ |
EXAMPLES 174–176
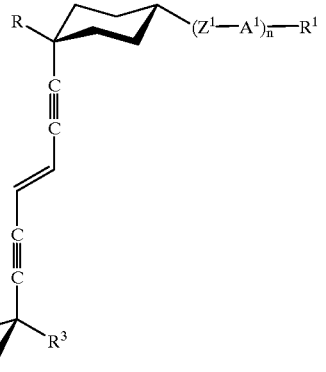
| | R | (Z¹—A¹)ₙ—R¹ | R²—(A²—Z²)ᵣ | R³ |
|---|---|---|---|---|
| 174) | n-Heptyl | 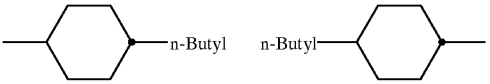—n-Butyl | n-Butyl— | n-Heptyl |
| 175) | n-Heptyl | 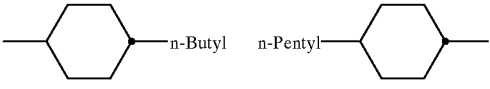—n-Butyl | n-Pentyl— | Methoxy |
| 176) | n-Pentyl | 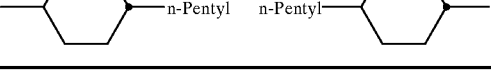—n-Pentyl | n-Pentyl— | Methoxy |

EXAMPLES 177–184

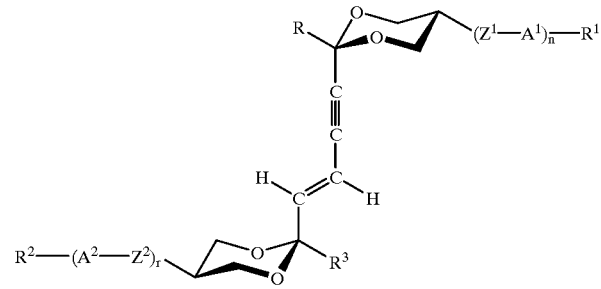

| | R | $(Z^1-A^1)_n-R^1$ | $R^2-(A^2-Z^2)_r$ | $R^3$ |
|---|---|---|---|---|
| 177) | n-Propyl | —⬡—n-Pentyl | n-Pentyl—⬡— | n-Propyl |
| 178) | n-Pentyl | —[dioxane]—n-Propyl | n-Pentyl—[dioxane]— | n-Pentyl |
| 179) | n-Propyloxy | —CH$_2$CH$_2$—⬡—n-Propyl | n-Propyl—⬡—CH$_2$CH$_2$— | n-Propyl |
| 180) | —CH=CF$_2$ | —⬡—n-Pentyl | n-Pentyloxy—⬡—CH$_2$CH$_2$— | —CH=CF$_2$ |
| 181) | n-Pentyloxy | —[dioxane]—n-Pentyl | n-Pentyl—[dioxane]—COO— | n-Propyloxy |
| 182) | —CH$_2$CH=CH$_2$ | —⬡—n-Propyl | n-Pentyl—[dioxane]— | n-Pentyl |
| 183) | Methyl | —⬡—CH=CF$_2$ | n-Pentyl—⬡— | Ethyl |
| 184) | Ethyl | —⬡(F)—n-Propyl | n-Pentyl—[dioxane]— | Methyl |

EXAMPLES 185–190
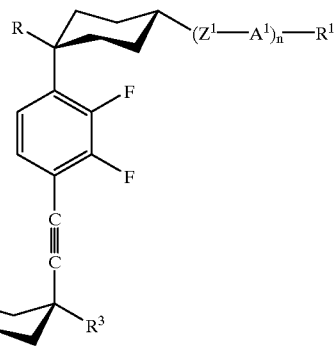
| | R | $(Z^1-A^1)_n-R^1$ | $R^2-(A^2-Z^2)_r$ | $R^3$ |
|---|---|---|---|---|
| 185) | n-Propyl | —[Cy]—n-Pentyl | n-Pentyl—[Cy]— | n-Propyl |
| 186) | Methoxy (C 106 I) | —[Cy]—n-Pentyl | n-Butyl—[Cy]— | n-Heptyl |
| 187) | n-Pentyl | —[Diox]—n-Propyl | n-Pentyl—[Diox]— | n-Pentyl |
| 188) | —CH=CF$_2$ | —[Cy]—n-Pentyl | n-Pentyloxy—[Cy]—CH$_2$CH$_2$— | —CH=CF$_2$ |
| 189) | —CH=CH$_2$ | —OOC—[Cy]—n-Propyloxy | n-Propyl—[Cy]—COO— | —CH=CH$_2$ |
| 190) | Ethyl | —CH$_2$CH$_2$—[Cy]—n-Propyl | n-Butyl—[Diox]— | OCH$_2$CH=CH$_2$ |

EXAMPLES 191–193

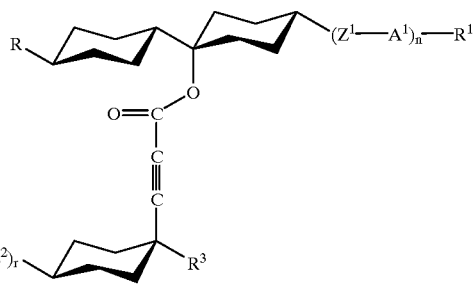

| | R | (Z$^1$—A$^1$)$_n$—R$^1$ | R$^2$—(A$^2$—Z$^2$)$_r$ | R$^3$ |
|---|---|---|---|---|
| 191) | n-Propyl | —⟨cyclohexyl⟩—n-Pentyl | n-Pentyl—⟨cyclohexyl⟩— | n-Propyl |
| 192) | n-Propyl | —⟨cyclohexyl⟩—n-Propyl | n-Propyloxy—⟨cyclohexyl⟩— | n-Pentyl |
| 193) | n-Pentyl | —⟨dioxanyl⟩—n-Propyl | n-Pentyl—⟨dioxanyl⟩— | n-Pentyl |

EXAMPLES 194–198

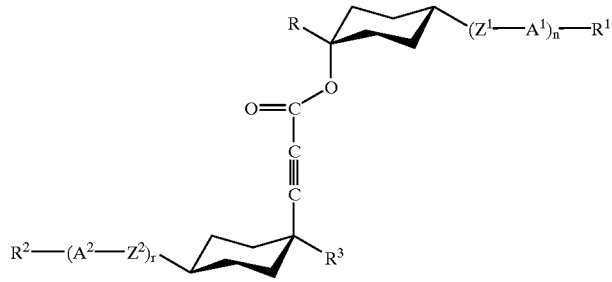

| | R | (Z$^1$—A$^1$)$_n$—R$^1$ | R$^2$—(A$^2$—Z$^2$)$_r$ | R$^3$ |
|---|---|---|---|---|
| 194) | n-Propyl | —⟨cyclohexyl⟩—n-Pentyl | n-Pentyl—⟨cyclohexyl⟩— | n-Propyl |
| 195) | n-Pentyl | —⟨dioxanyl⟩—n-Propyl | n-Pentyl—⟨dioxanyl⟩— | n-Pentyl |
| 196) | n-Propyloxy | —CH$_2$CH$_2$—⟨cyclohexyl⟩—n-Propyl | n-Propyl—⟨cyclohexyl⟩—CH$_2$CH$_2$— | n-Propyl |

-continued

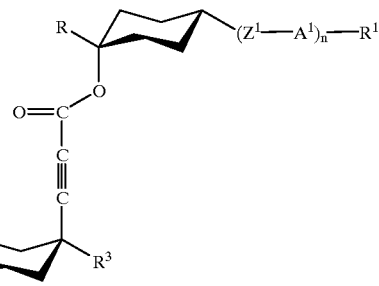

| | R | $(Z^1—A^1)_n—R^1$ | $R^2—(A^2—Z^2)_r$ | $R^3$ |
|---|---|---|---|---|
| 197) | Ethyl | —CH₂CH₂—⟨cyclohexyl⟩—n-Propyl | n-Butyl—⟨1,3-dioxane⟩— | OCH₂CH=CH₂ |
| 198) | n-Propyl | — | n-Propyl—⟨cyclohexyl⟩— | n-Propyl |

EXAMPLES 199–203

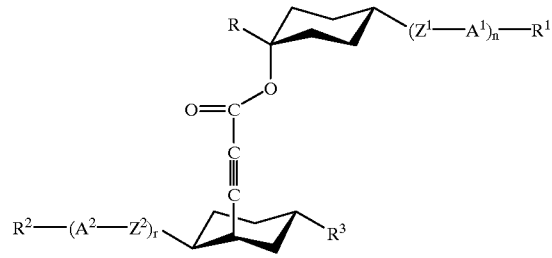

| | R | $(Z^1—A^1)_n—R^1$ | $R^2—(A^2—Z^2)_r$ | $R^3$ |
|---|---|---|---|---|
| 199) | n-Propyl | —⟨cyclohexyl⟩—n-Pentyl | n-Pentyl—⟨cyclohexyl⟩— | n-Propyl |
| 200) | n-Propyl | —⟨cyclohexyl⟩—n-Propyl | n-Propyloxy—⟨cyclohexyl⟩— | n-Pentyl |
| 201) | n-Pentyl | —⟨1,3-dioxane⟩—n-Propyl | n-Pentyl—⟨1,3-dioxane⟩— | n-Pentyl |
| 202) | —CH₂CH=CH₂ | —⟨cyclohexyl⟩—n-Propyl | n-Pentyl—⟨1,3-dioxane⟩— | n-Pentyl |
| 203) | n-Propyl | —⟨cyclohexyl⟩—⟨cyclohexyl⟩—n-Propyl | n-Propyl—⟨cyclohexyl⟩— | n-Pentyloxy |

EXAMPLES 204–208

| | R | $(Z^1-A^1)_n-R^1$ | $R^2-(A^2-Z^2)_r$ | $R^3$ |
|---|---|---|---|---|
| 204) | n-Propyl | —⟨cyclohexyl⟩—n-Pentyl | n-Pentyl—⟨cyclohexyl⟩— | n-Propyl |
| 205) | n-Propyl | —⟨cyclohexyl⟩—n-Propyl | n-Propyloxy—⟨cyclohexyl⟩— | n-Pentyl |
| 206) | n-Propyloxy | —CH₂CH₂—⟨cyclohexyl⟩—n-Propyl | n-Propyl—⟨cyclohexyl⟩—CH₂CH₂— | n-Propyl |
| 207) | —CH=CF₂ | —⟨cyclohexyl⟩—n-Pentyl | n-Pentyloxy—⟨cyclohexyl⟩—CH₂CH₂— | —CH=CF₂ |
| 208) | Ethyl | —⟨cyclohexyl-F⟩—n-Propyl | n-Pentyl—⟨dioxane⟩— | Methyl |

EXAMPLES 209–212

| | R | $(Z^1-A^1)_n-R^1$ | $R^2-(A^2-Z^2)_r$ | $R^3$ |
|---|---|---|---|---|
| 209) | n-Pentyl | —⟨dioxane⟩—n-Propyl | n-Pentyl—⟨dioxane⟩— | n-Pentyl |
| 210) | n-Propyloxy | —CH₂CH₂—⟨cyclohexyl⟩—n-Propyl | n-Propyl—⟨cyclohexyl⟩—CH₂CH₂— | n-Propyl |

-continued

| | R | $(Z^1-A^1)_n-R^1$ | $R^2-(A^2-Z^2)_r$ | $R^3$ |
|---|---|---|---|---|
| 211) | —CH₂CH=CH₂ | —⌬—n-Propyl | n-Pentyl—[1,3-dioxane]— | n-Pentyl |
| 212) | Ethyl | —⌬(F)—n-Propyl | n-Pentyl—[1,3-dioxane]— | Methyl |

EXAMPLES 213–218

| | R | $(Z^1-A^1)_n-R^1$ | $R^2-(A^2-Z^2)_r$ | $R^3$ |
|---|---|---|---|---|
| 213) | n-Propyl | —⌬—n-Pentyl | n-Pentyl—⌬— | n-Propyl |
| 214) | n-Propyl | —⌬—n-Propyl | n-Propyloxy—⌬— | n-Pentyl |
| 215) | n-Pentyl | —[1,3-dioxane]—n-Propyl | n-Pentyl—[1,3-dioxane]— | n-Pentyl |
| 216) | n-O-Propyl | —CH₂CH₂—⌬—n-Propyl | n-Propyl—⌬—CH₂CH₂— | n-Propyl |
| 217) | —CH=CH₂ | —OOC—⌬—n-Propyloxy | n-Propyl—⌬—COO— | —CH=CH₂ |

-continued

| | R | (Z¹—A¹)ₙ—R¹ | R²—(A²—Z²)ᵣ | R³ |
|---|---|---|---|---|
| 218) | —CH₂CH=CH₂ | —⟨cyclohexyl⟩—n-Propyl | n-Pentyl—⟨1,3-dioxane⟩— | n-Pentyl |

EXAMPLES 219–221

| | R | (Z¹—A¹)ₙ—R¹ | R²—(A²—Z²)ᵣ | R³ |
|---|---|---|---|---|
| 219) | n-Propyl | —⟨cyclohexyl⟩—n-Pentyl | n-Pentyl—⟨cyclohexyl⟩— | n-Propyl |
| 220) | n-Pentyl | —⟨1,3-dioxane⟩—n-Propyl | n-Pentyl—⟨1,3-dioxane⟩— | n-Pentyl |
| 221) | —CH=CH₂ | —OOC—⟨cyclohexyl⟩—n-Propyloxy | n-Propyl—⟨cyclohexyl⟩—COO— | —CH=CH₂ |

EXAMPLES 222–226

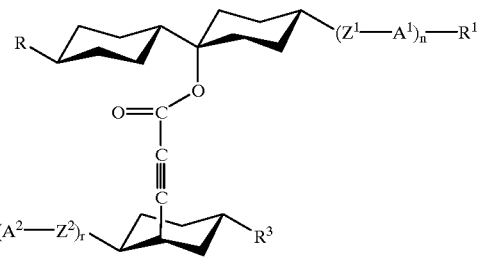

| | R | (Z¹—A¹)ₙ—R¹ | R²—(A²—Z²)ᵣ | R³ |
|---|---|---|---|---|
| 222) | n-Pentyl | —[1,3-dioxane]—n-Propyl | n-Pentyl—[1,3-dioxane]— | n-Pentyl |
| 223) | n-Propyloxy | —CH₂CH₂—[cyclohexyl]—n-Propyl | n-Propyl—[cyclohexyl]—CH₂CH₂— | n-Propyl |
| 224) | —CH=CH₂ | —OOC—[cyclohexyl]—n-Propyloxy | n-Propyl—[cyclohexyl]—COO— | —CH=CH₂ |
| 225) | —CH₂CH=CH₂ | —[cyclohexyl]—n-Propyl | n-Pentyl—[1,3-dioxane]— | n-Pentyl |
| 226) | Methyl | —[cyclohexyl]—CH=CF₂ | n-Pentyl—[cyclohexyl]— | Ethyl |

EXAMPLES 227–230

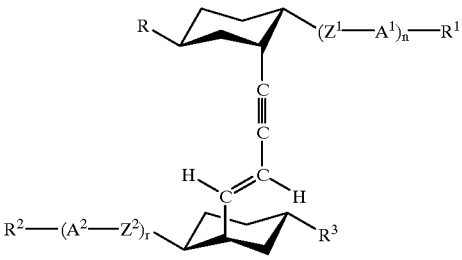

| | R | (Z¹—A¹)ₙ—R¹ | R²—(A²—Z²)ᵣ | R³ |
|---|---|---|---|---|
| 227) | n-Propyl | —[cyclohexyl]—n-Propyl | n-Propyloxy—[cyclohexyl]— | n-Pentyl |
| 228) | n-Propyloxy | —CH₂CH₂—[cyclohexyl]—n-Propyl | n-Propyl—[cyclohexyl]—CH₂CH₂— | n-Propyl |

-continued

[Structure: cyclohexane with R and (Z¹—A¹)ₙ—R¹ substituents, connected via C≡C-CH=CH to another cyclohexane with R²—(A²—Z²)ᵣ and R³ substituents]

| | R | (Z¹—A¹)ₙ—R¹ | R²—(A²—Z²)ᵣ | R³ |
|---|---|---|---|---|
| 229) | —CH₂CH=CH₂ | cyclohexyl-n-Propyl | n-Pentyl-(1,3-dioxane) | n-Pentyl |
| 230) | n-Propyl | — | n-Propyl-cyclohexyl | n-Propyl |

EXAMPLES 231–234

[Structure: cyclohexane with R and (Z¹—A¹)ₙ—R¹ substituents, connected via phenyl ring and C≡C to another cyclohexane with R²—(A²—Z²)ᵣ and R³ substituents]

| | R | (Z¹—A¹)ₙ—R¹ | R²—(A²—Z²)ᵣ | R³ |
|---|---|---|---|---|
| 231) | n-Propyl | cyclohexyl-n-Propyl | n-Propyloxy-cyclohexyl | n-Pentyl |
| 232) | n-Propyloxy | —CH₂CH₂-cyclohexyl-n-Propyl | n-Propyl-cyclohexyl-CH₂CH₂— | n-Propyl |
| 233) | —CH₂CH=CH₂ | cyclohexyl-n-Propyl | n-Pentyl-(1,3-dioxane) | n-Pentyl |
| 234) | n-Propyl | — | n-Propyl-cyclohexyl | n-Propyl |

EXAMPLES 235–238

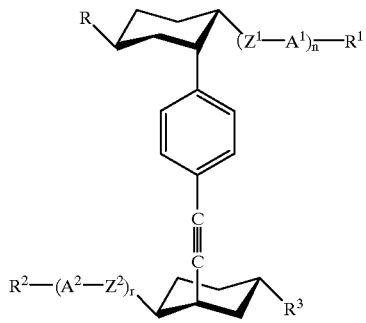

| | R | $(Z^1-A^1)_n-R^1$ | $R^2-(A^2-Z^2)_r$ | $R^3$ |
|---|---|---|---|---|
| 235) | n-Propyl | —⬡—n-Pentyl | n-Pentyl—⬡— | n-Propyl |
| 236) | n-Pentyl | —(dioxane)—n-Propyl | n-Pentyl—(dioxane)— | n-Pentyl |
| 237) | —CH=CF$_2$ | —⬡—n-Pentyl | n-Pentyloxy—⬡—CH$_2$CH$_2$— | —CH=CF$_2$ |
| 238) | Ethyl | —CH$_2$CH$_2$—⬡—n-Propyl | n-Butyl—(dioxane)— | OCH$_2$CH=CH$_2$ |

EXAMPLES 239–241

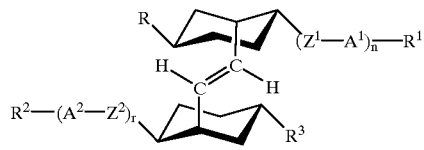

| | R | $(Z^1-A^1)_n-R^1$ | $R^2-(A^2-Z^2)_r$ | $R^3$ |
|---|---|---|---|---|
| 239) | n-Propyloxy | —CH$_2$CH$_2$—⬡—n-Propyl | n-Propyl—⬡—CH$_2$CH$_2$— | n-Propyl |
| 240) | —CH=CH$_2$ | —OOC—⬡—n-Propyl | n-Propyl—⬡—COO— | —CH=CH$_2$ |
| 241) | Ethyl | —CH$_2$CH$_2$—⬡—n-Propyl | n-Butyl—(dioxane)— | OCH$_2$CH=CH$_2$ |

EXAMPLES 242–245

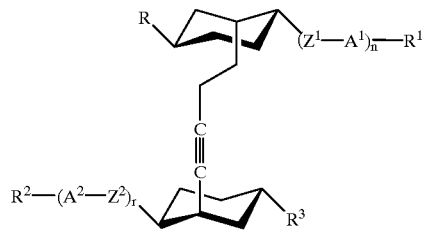

| R | $(Z^1-A^1)_n-R^1$ | $R^2-(A^2-Z^2)_r$ | $R^3$ |
|---|---|---|---|
| 242) n-Propyl | —⬡—n-Pentyl | n-Pentyl—⬡— | n-Propyl |
| 243) n-Propyloxy | —CH₂CH₂—⬡—n-Propyl | n-Propyl—⬡—CH₂CH₂— | n-Propyl |
| 244) n-Pentyloxy | —[dioxane]—n-Pentyl | n-Pentyl—[dioxane]—COO— | n-Propyloxy |
| 245) —CH₂CH=CH₂ | —⬡—n-Propyl | n-Pentyl—[dioxane]— | n-Pentyl |

EXAMPLE 246

1,6-Bis(4,4'-dipentylbicyclohexyl-4-yl)hexa-1,3,5-triyne a) 1,6-Bis(4,4'-dipentylbicyclohexyl-4-yl)hexa-2,4-diyne-1,6-diol 12.3 g of dichlorobutyne in 20 ml of diethyl ether are added dropwise to a solution of sodium amide in liquid ammonia (prepared from 9.2 g of sodium). After 5 minutes, 58.55 g of 4,4'-dipentylbicyclohexyl-4-carbaldehyde in 10 ml of diethyl ether are added to the solution, and after 1 hour, the reaction mixture is decomposed using ammonium chloride. After the ammonia has been evaporated, the residue is taken up in diethyl ether and subjected to customary work-up, giving 1,6-bis(4,4'-dipentylbicyclohexyl-4-yl)hexa-2,4-diyne-1,6-diol.

b) 1,6-Bis(4,4'-dipentylbicyclohexyl-4-yl)-1,6-dichlorohexa-2,4-diyne 5 ml of thionyl chloride are added with cooling to 19.42 g of 1,6-bis(4,4'-dipentylbicyclohexyl-4-yl)hexa-2,4-diyne-1,6-diol. After 2 hours at RT, the mixture is warmed at 50° C. for 1 hour, then decomposed using ice and subjected to conventional work-up, giving the product.

c) 1,6-Bis(4,4'-dipentylbicyclohexyl-4-yl)hexa-1,3,5-triyne 8.32 g of 1,6-bis(4,4'-dipentylbicyclohexyl-4-yl)-1,6-dichlorohexa-2,4-diyne are dissolved in 30 ml of diethyl ether and added dropwise to a solution of sodium amide in liquid ammonia (prepared from 1 g of sodium). After 30 minutes, the excess amide is decomposed using ammonium chloride, the ammonia is evaporated, and the residue is subjected to conventional work-up, giving 1,6-bis(4,4'-dipentylbicyclohexyl-4-yl) hexa-1,3,5-triyne (C 90 N (63) I, $\Delta\epsilon=-1.56$, $\Delta n=-0.028$).

The following compounds according to the invention can be obtained analogously using the corresponding precursors:

EXAMPLES 247–252

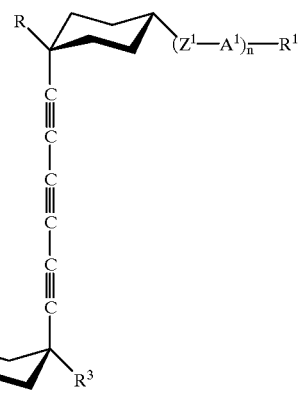

| | R | $(Z^1-A^1)_n-R^1$ | $R^2-(A^2-Z^2)_r$ | $R^3$ |
|---|---|---|---|---|
| 247) | n-Propyl | —⟨cyclohexyl⟩—n-Pentyl | n-Pentyl—⟨cyclohexyl⟩— | n-Propyl |
| 248) | n-Propyl | —⟨cyclohexyl⟩—n-Propyl | n-Propyloxy—⟨cyclohexyl⟩— | n-Pentyl |
| 249) | n-Pentyl | —⟨dioxanyl⟩—n-Propyl | n-Pentyl—⟨dioxanyl⟩— | n-Pentyl |
| 250) | n-Propyloxy | —$CH_2CH_2$—⟨cyclohexyl⟩—n-Propyl | n-Propyl—⟨cyclohexyl⟩—$CH_2CH_2$— | n-Propyl |
| 251) | n-Propyl | —⟨cyclohexyl⟩—⟨cyclohexyl⟩—n-Propyl | n-Propyl—⟨cyclohexyl⟩— | n-Propyloxy |
| 252) | Ethyl | —$CH_2CH_2$—⟨cyclohexyl⟩—n-Propyl | n-Butyl—⟨dioxanyl⟩— | $OCH_2CH=CH_2$ |

EXAMPLES 253–255
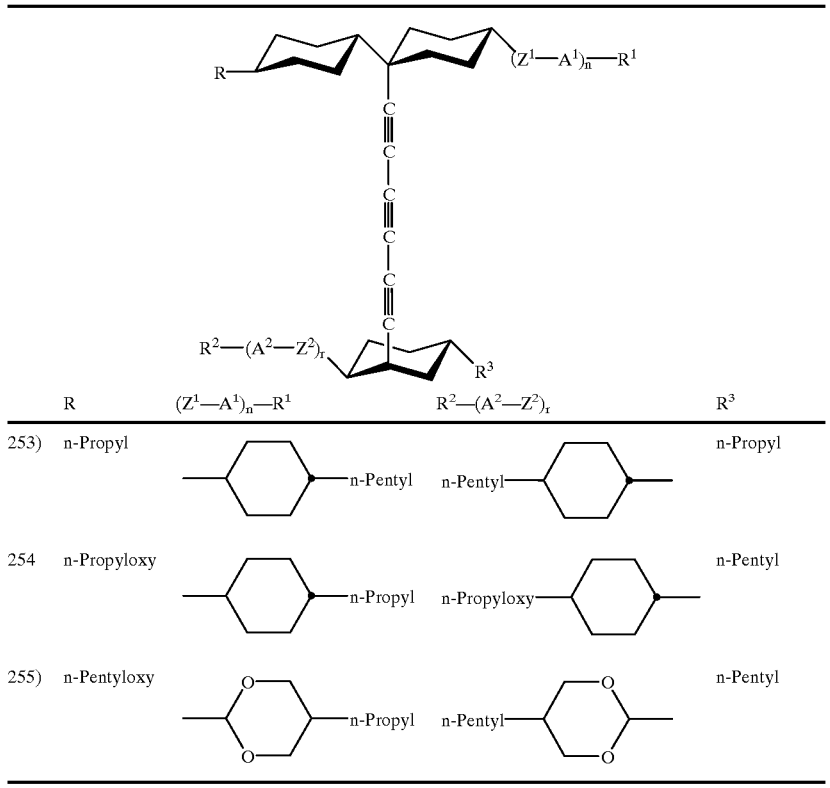
| | R | $(Z^1-A^1)_n-R^1$ | $R^2-(A^2-Z^2)_r$ | $R^3$ |
|---|---|---|---|---|
| 253) | n-Propyl | —⬡—n-Pentyl | n-Pentyl—⬡— | n-Propyl |
| 254 | n-Propyloxy | —⬡—n-Propyl | n-Propyloxy—⬡— | n-Pentyl |
| 255) | n-Pentyloxy | —(dioxane)—n-Propyl | n-Pentyl—(dioxane)— | n-Pentyl |
EXAMPLES 256–259
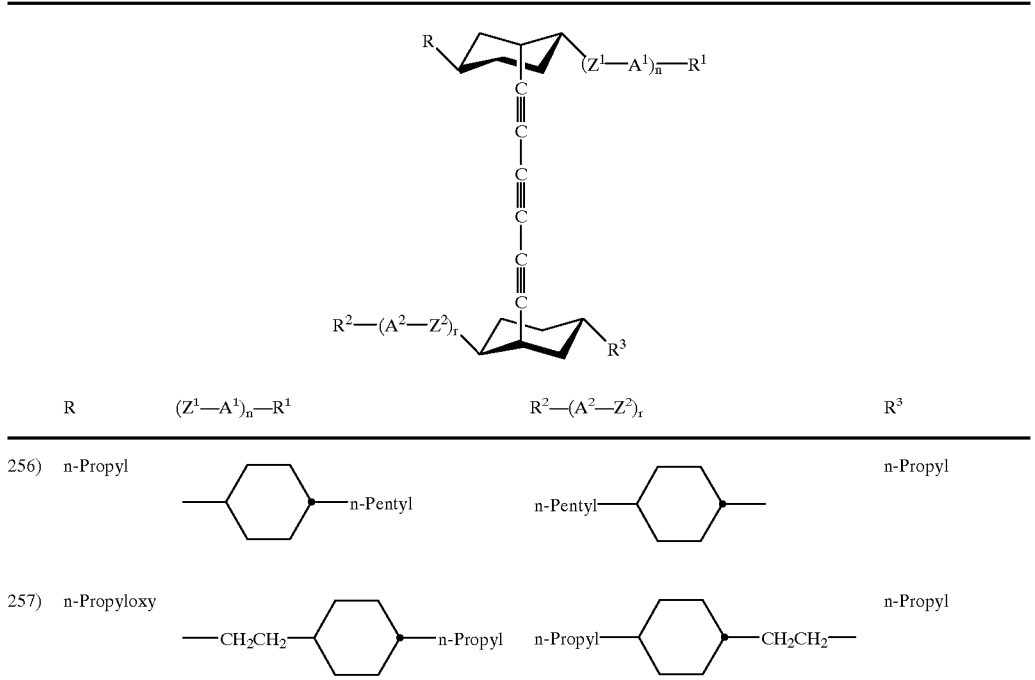
| | R | $(Z^1-A^1)_n-R^1$ | $R^2-(A^2-Z^2)_r$ | $R^3$ |
|---|---|---|---|---|
| 256) | n-Propyl | —⬡—n-Pentyl | n-Pentyl—⬡— | n-Propyl |
| 257) | n-Propyloxy | —CH₂CH₂—⬡—n-Propyl | n-Propyl—⬡—CH₂CH₂— | n-Propyl |

-continued
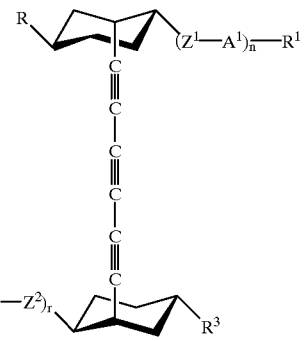
| | | | | |
|---|---|---|---|---|
| 258) | n-Pentyloxy | 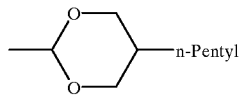 | 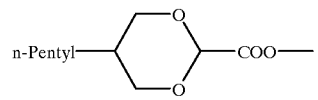 | n-Propyloxy |
| 259) | Ethyl | 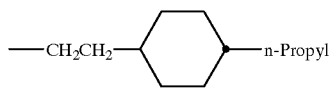 | 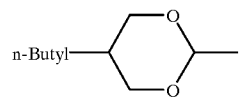 | $OCH_2CH=CH_2$ |
The following compounds according to the invention can be obtained analogously using the corresponding precursors:
EXAMPLES 260–265
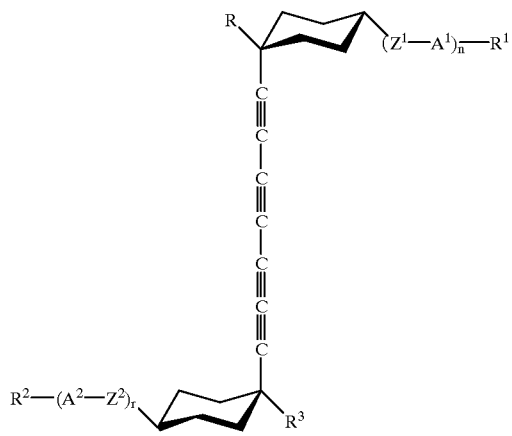
| | R | $(Z^1-A^1)_n-R^1$ | $R^2-(A^2-Z^2)_r$ | $R^3$ |
|---|---|---|---|---|
| 260) | n-Pentyl (C 164 I) | 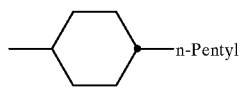 | 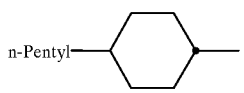 | n-Pentyl |
| 261) | n-Propyl | 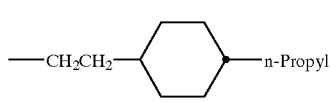 | 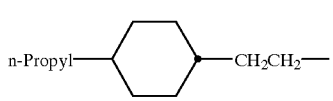 | n-Pentyl |

-continued

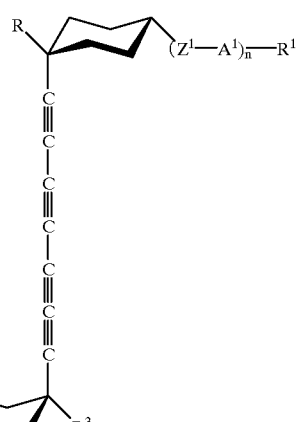

| | R | $(Z^1-A^1)_n-R^1$ | $R^2-(A^2-Z^2)_r$ | $R^3$ |
|---|---|---|---|---|
| 262) | n-Pentyl | 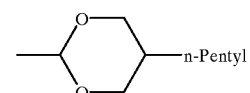 | 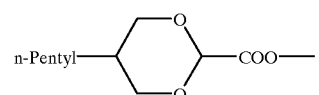 | n-Pentyl |
| 263) | n-Propyloxy | 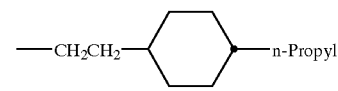 | 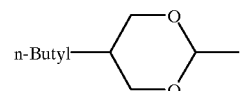 | n-Propyl |
| 264 | n-Propyl | 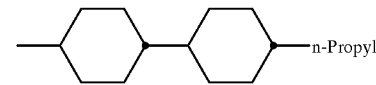 | 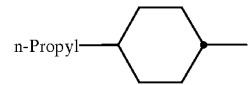 | n-Propyloxy |
| 265) | Ethyl | 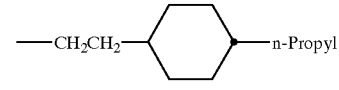 | 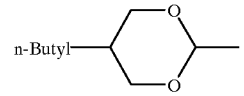 | $OCH_2CH=CH_2$ |

EXAMPLE 266

The compound from Example 11 has the following values of $n_\|$, $n_\perp$ and $\Delta n$ at a measurement temperature of 49.4° C. as a function of the wavelength λ of the light used:

| λ | n‖ | n⊥ | Δn |
|---|---|---|---|
| 436 | 1.5188 | 1.5188 | 0 |
| 509 | 1.5121 | 1.5107 | 0.0014 |
| 546 | 1.5096 | 1.5077 | 0.0019 |
| 589 | 1.5073 | 1.5052 | 0.0021 |
| 632 | 1.5054 | 1.5029 | 0.0025 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A cyclohexane compound of formula I $$R-(A-Z)_m-B-(Z^1-A^1)_n-R^1$$
$$|$$
$$(X)_p$$
$$|$$
$$R^2-(A^2-Z^2)_r-B^1-(Z^3-A^3)_s-R^3$$

I wherein

B and $B^1$, are each independently,

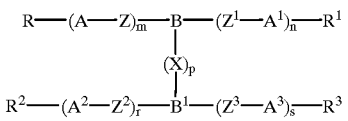

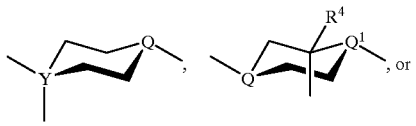, or

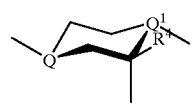

where the rings B and B$^1$ are each bonded to the group (X)$_p$ via the axial bond, and one or two non-adjacent CH$_2$ groups in these rings are optionally replaced by O, Y is each independently C or Si, Q and Q$^1$ are each independently CH or SiH, X is each independently —C≡C—, —CH=CH—, —CF=CF—, —CF=CH—, —CH$_2$—, —COO— or 1,4-phenylene in which one or more CH groups are independently optionally replaced by N or CF, p is 1, 2, 3 or 4, R, R$^1$, R$^2$, R$^3$ and R$^4$ are each independently an alkyl radical having 1–12 carbon atoms which is unsubstituted or at least monosubstituted by halogen and in which one or more CH$_2$ groups are independently optionally replaced by —O—, —S—, —CO—,

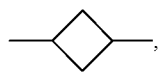

—CO—O—, —O—CO—, —O—CO—O— or —CH=CH— in such a way that heteroatoms are not connected directly, or are CN, F, —CF$_3$, —OCHF$_2$, —OCF$_3$, —OCHFCF$_3$, —OCH$_2$CF$_3$, —OCF$_2$—CF$_3$ or —CH=CF$_2$; and R$^4$ can be H;

A, A$^1$, A$^2$ and A$^3$ are each independently

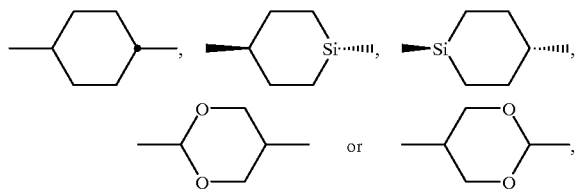

or 1,4-phenylene in which one or more CH groups are replaced by N, where the rings A, A$^1$, A$^2$ and A$^3$, are independently optionally substituted by at least one F atom, —NCS, —CN, —CF$_3$ or —OCF$_3$, Z, Z$^1$, Z$^2$ and Z$^3$ are each independently —CO—O—, —O—CO—, —CH$_2$O—, —CH=CH—, —O—, —O—CH$_2$—, —CH$_2$CH$_2$—, —(CH$_2$)$_3$—, —(CH$_2$)$_4$—, —CF$_2$—CF$_2$—, —OCF$_2$— or a single bond, and n, m, r and s are each independently 0, 1 or 2.

2. A cyclohexane compound of formula I according to claim 1, having an optical anisotropy Δn of <0.05 at a reduced temperature of 0.9 and a wavelength of 589 nm.

3. A cyclohexane compound of formula I according to claim 1, wherein B and B$^1$ are each independently

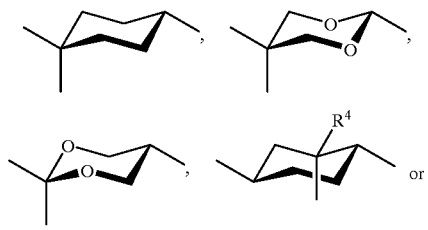

4. A cyclohexane compound of formula I according to claim 1, wherein Y is C, and Q and Q$^1$ are CH.

5. A cyclohexane compound of formula I according to claim 1, wherein Z, Z$^1$, Z$^2$ and Z$^3$ are each —CH$_2$CH$_2$—, —COO—, —OOC— or a single bond.

6. A cyclohexane compound of formula I according to claim 1, wherein R, R$^1$, R$^2$ and R$^3$ are each independently —CN, —F, —OCF$_3$, CF$_3$, —OCF$_2$CF$_3$, —CH=CF$_2$, straight-chain alkyl or alkoxy having 1 to 10 carbon atoms or alkenyl or alkenyloxy having 2 to 10 carbon atoms.

7. A cyclohexane compound of formula I according to claims 1, wherein (X)$_p$ is: —C≡C—, —C≡C—C≡C—, —C≡C—C≡C—C≡C—, —C≡C—C≡C—C≡C—C≡C—, —CH=CH—, —CH=CH—CH=CH—, —C≡C—CH=CH—, —C≡C—CH=CH—C≡C, —CH=CH—C≡C—CH=CH—, —C≡C—COO—, —CH=CH—COO—, —CH$_2$—CH$_2$—C≡C—, —CH$_2$—CH$_2$—C≡C—C≡C—, —CH$_2$—CH$_2$—C≡C—CH=CH—,

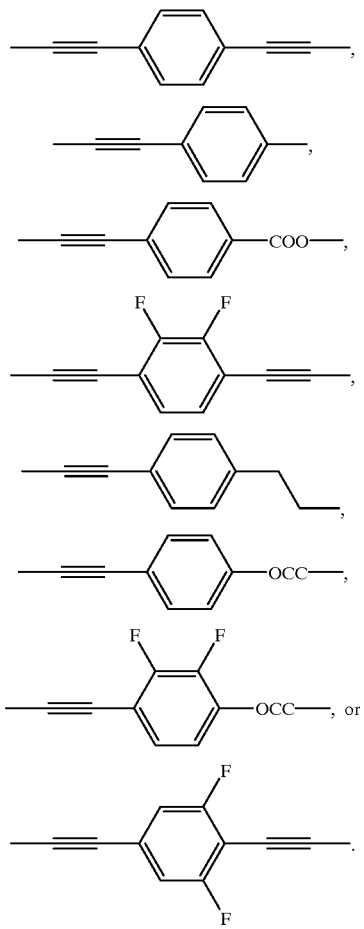

8. A cyclohexane compound according to claim 1, wherein A, A$^1$, A$^2$ and/or A$^3$ are each independently:

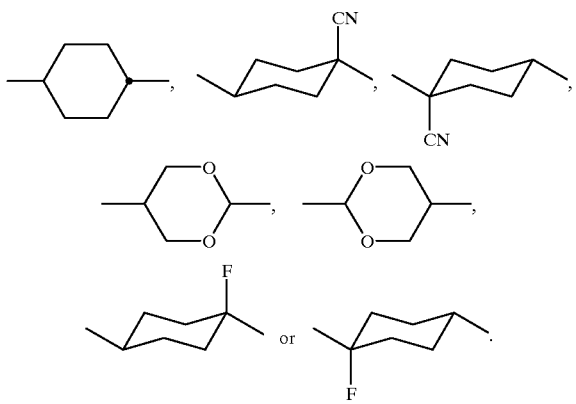

9. A cyclohexane compound according to claim 1, wherein m, n, r and s, are each independently 0 or 1.

10. A compound of the formula I according to claim 1, which exhibits a wavelength-dependent inversion of Δn.

11. A liquid-crystalline medium having at least two liquid-crystalline components, wherein at least one component is a compound of formula I.

12. A liquid-crystal display element containing a liquid-crystalline medium according to claim 11.

13. A liquid-crystal display comprising a reflective or transflective element, containing a dielectric which is a liquid-crystalline medium according to claim 11.

14. An electro-optical display element containing a dielectric which is a liquid-crystalline medium according to claim 11.

15. A liquid-crystalline polymer produced by polymerizing a compound according to claim 1.

16. An optical switch or optical filter comprising a compound according to claim 1.

* * * * *